United States Patent
Scarselli et al.

(10) Patent No.: US 11,708,394 B2
(45) Date of Patent: Jul. 25, 2023

(54) MODIFIED MENINGOCOCCAL FHBP POLYPEPTIDES

(71) Applicant: GLAXOSMITHKLINE BIOLOGICALS SA, Rixensart (BE)

(72) Inventors: Maria Scarselli, Siena (IT); Daniele Veggi, Siena (IT)

(73) Assignee: GlaxoSmithKline Biologicals SA, Rixensart (BE)

( * ) Notice: Subject to any disclaimer, the term of this patent is extended or adjusted under 35 U.S.C. 154(b) by 0 days.

(21) Appl. No.: 17/265,610

(22) PCT Filed: Aug. 9, 2019

(86) PCT No.: PCT/EP2019/071410
§ 371 (c)(1),
(2) Date: Feb. 3, 2021

(87) PCT Pub. No.: WO2020/030782
PCT Pub. Date: Feb. 13, 2020

(65) Prior Publication Data
US 2021/0277069 A1 Sep. 9, 2021

(30) Foreign Application Priority Data
Aug. 9, 2018 (EP) .................................. 18188321

(51) Int. Cl.
*C07K 14/22* (2006.01)
*A61P 31/04* (2006.01)
*A61K 39/095* (2006.01)

(52) U.S. Cl.
CPC ............ *C07K 14/22* (2013.01); *A61K 39/095* (2013.01); *A61P 31/04* (2018.01); *C07K 2319/00* (2013.01)

(58) Field of Classification Search
CPC ..... C07K 14/22; C07K 2319/00; A61P 31/04; A61K 39/095
See application file for complete search history.

(56) References Cited

FOREIGN PATENT DOCUMENTS

| WO | 2006081259 A2 | 8/2006 |
|---|---|---|
| WO | 2010046715 A1 | 4/2010 |
| WO | 2011051893 A | 5/2011 |
| WO | 2011126863 A1 | 10/2011 |
| WO | 2015128480 A1 | 9/2015 |
| WO | 2016008960 A1 | 1/2016 |
| WO | 2016008961 A1 | 1/2016 |
| WO | 2016014719 A1 | 1/2016 |

OTHER PUBLICATIONS

European Patent Office as International Searching Authority, International Search Report and Written Opinion for corresponding International Application No. PCT/EP2019/071410, dated Dec. 5, 2019 (19 pages).

Johnson et al., "Design and Evaluation of Meningococcal Vaccines through Structure-Based Modification of Host and Pathogen Molecules", PLOS Pathogens, Oct. 25, 2012, p. e1002981, vol. 8, No. 10 (13 pages).

*Primary Examiner* — Robert A Zeman

(57) ABSTRACT

The present invention provides mutated fHbp polypeptides and fusion proteins comprising said mutated fHbp polypeptides that are useful as components of immunogenic compositions for immunizing against *Neisseria meningitidis* infection.

3 Claims, 25 Drawing Sheets
Specification includes a Sequence Listing.

C

D

C

D

A

B

MODIFIED MENINGOCOCCAL FHBP POLYPEPTIDES

TECHNICAL FIELD

This invention is in the field of protein engineering, relating in particular to the meningococcal factor H binding protein (fHbp), which is a useful vaccine immunogen.

BACKGROUND

Invasive meningococcal disease (IMD) is caused by the bacterial pathogen *Neisseria meningitidis*. Of the five serogroups mainly associated with IMD globally (MenA, B, C, W and Y), MenB is the predominant serogroup causing IMD in a number of regions, including Canada, the United States, Australia, New Zealand and Europe. MenB is a serious and often deadly disease, affecting mainly infants and young adults. It is easily mis-diagnosed, can kill within 24 hours of onset and can cause serious, life-long disabilities despite the administration of treatment.

There are currently two licensed vaccines that have been designed to immunize against serogroup B meningococcus: GSK's BEXSERO and Pfizer's TRUMENBA.

BEXSERO (also known generically as 4CMenB) contains a preparation of outer membrane vesicles (OMVs) from the epidemic strain of group B Meningococcal NZ98/254 together with five meningococcal antigens: Neisserial Heparin Binding protein A (NHBA), factor H binding protein (fHbp) variant 1.1, Neisserial adhesion protein A (NadA), and accessory proteins GNA1030 and GNA2091. Four of these antigens are present as fusion proteins (an NHBA-GNA1030 fusion protein and a GNA2091-fHbp fusion protein). 4CMenB is described in literature (for example, see Bai et al. (2011) *Expert Opin Biol Ther.* 11:969-85, Su & Snape (2011) *Expert Rev Vaccines* 10:575-88). The terms "BEXSERO" and "4CMenB" are used interchangeably herein.

TRUMENBA contains two lipidated MenB fHbp antigens (v1.55 and v3.45) adsorbed on aluminium phosphate.

fHbp (also known interchangeably in the art as genome-derived *Neisseria* antigen (GNA) 1870, LP2086 and protein '741') binds to human factor H (hfH), which is a large (180 kDa) multi-domain soluble glycoprotein, consisting of 20 complement control protein (CCP) modules connected by short linker sequences. hfH circulates in human plasma and regulates the Alternative Pathway of the complement system. Functional binding of fHbp to hfH relies predominantly on CCP modules (or domains) 6-7 of hfH, and enhances the ability of the bacterium to resist complement-mediated killing. Therefore, expression of fHbp enables survival in ex vivo human blood and serum.

As different fHbp classification schemes have been proposed, a dedicated database is available with a unified fHbp nomenclature for the assignment of new sub-variants: neisseria(dot)org/nm/typing/fhbp (also as pubmlst(dot)org/*neisseria*/fHbp/).

fHbp has been classified into three (main) variants 1, 2 and 3, which were further divided into sub-variants fHbp-1.x, fHbp-2.x and fHbp-3.x, where x denotes the specific peptide sub-variant. In contrast to v2 and v3, fHbp v1 is highly heterogeneous and contains several subvariants. In a different nomenclature scheme, the sub/variants are grouped into subfamily A (corresponding to variants 2 and 3) and subfamily B (corresponding to variant 1) based on sequence diversity.

BEXSERO is predicted to provide broad coverage against MenB strains circulating worldwide (Medini D et al., *Vaccine* 2015; 33:2629-2636; Vogel U et al. *Lancet Infect Dis* 2013; 13:416-425; Křížová et al., *Epidemiol Mikrobiol Imunol* 2014; 63:103-106; Tzanakaki G et al. *BMC Microbiol* 2014; 14:111; Wasko I et al. *Vaccine* 2016; 34:510-515; 6. Simões M J et al. *PLoS ONE* 12(5): e0176177; and Parikh S R et al. *Lancet Infect Dis* 2017; 17:754-62). Furthermore, following the introduction of BEXSERO into the UK national infant immunization programme in September 2015, data at 10 months showed 83% vaccine efficacy on all MenB strains after two doses (Parikh S R et al., *Lancet* 2016; 388:2775-82).

However, bactericidal activity is variant specific; antibodies raised against one variant are not necessarily cross-protective against other variants, although some cross-reactivity has been described between fHbp v2 and v3 (Masignani V et al., *J Exp Med* 2003; 197:789-799). Antibodies raised against sub-variant fHbpv1.1, included in the 4CMenB vaccine, are highly cross-reactive with the most frequently occurring fHbp v1 sub-variants but are less cross-reactive with v1 sub-variants that are most distantly related to v1.1. Furthermore, antibodies raised against sub-variant fHbpv1.1 included in the 4CMenB vaccine are poorly cross-reactive with fHbp v2 and v3 (Brunelli B et al., *Vaccine* 2011; 29:1072-1081). This means that 4CMenB coverage is not able to extend to some meningococcal strains carrying fHbp v2, v3, or strains carrying some v1 sub-variants.

Therefore, despite the efficacy of licensed serogroup B meningococcus vaccines such as BEXSERO, there remains a need to develop meningococcal vaccines that retain the efficacy of, and are non-inferior to, existing licensed vaccines, such as 4CMenB, but with the added value of improved coverage against meningococcal strains carrying fHbp variants that are not well covered by existing vaccines.

SUMMARY OF THE INVENTION

A first aspect of the invention provides a mutant v1.13 meningococcal fHbp polypeptide comprising an amino acid sequence having at least 80% sequence identity to SEQ ID NO: 2, wherein the amino acid sequence of said mutant v1.13 meningococcal fHbp polypeptide includes a substitution mutation at E211, S216, E232, or combinations thereof, of SEQ ID NO: 2.

A second aspect of the invention provides a mutant v1.15 meningococcal fHbp polypeptide comprising an amino acid sequence having at least 80% sequence identity to SEQ ID NO:6, wherein the amino acid sequence of said mutant v1.15 meningococcal fHbp polypeptide includes a substitution mutation at E214, S219, E235, or combinations thereof, of SEQ ID NO: 6.

A third aspect of the invention provides a fusion polypeptide comprising all three of v1, v2 and v3 meningococcal fHbp polypeptides, wherein the variant fHbp sequences are in the order v2-v3-v1 from N- to C-terminus, and wherein the v1 polypeptide is a mutant v1.13 fHbp polypeptide according to the first aspect of the invention or a mutant v1.15 fHbp polypeptide according to the second aspect of the invention.

A fourth aspect of the invention provides an isolated nucleic acid molecule, optionally a plasmid, comprising a nucleotide sequence encoding a mutant v1.13 fHbp polypeptide according to the first aspect of the invention, a mutant v1.15 fHbp polypeptide according to the second aspect of the invention, or a fusion polypeptide according to the third aspect of the invention.

A fifth aspect of the invention provides a recombinant host cell transformed with a nucleic acid molecule according to the fourth aspect of the invention.

A sixth aspect of the invention provides outer membrane vesicles obtained or prepared from the recombinant host cell according to the fifth aspect of the invention.

A seventh aspect of the invention provides an immunogenic composition comprising a mutant v1.13 fHbp polypeptide according to the first aspect of the invention, a mutant v1.15 fHbp polypeptide according to the second aspect of the invention, a fusion polypeptide according to the third aspect of the invention, or an outer membrane vesicle according to the sixth aspect of the invention. Said immunogenic composition is useful for immunizing a mammal, preferably a human, against *Neisseria meningitidis* infection.

Figure 17:
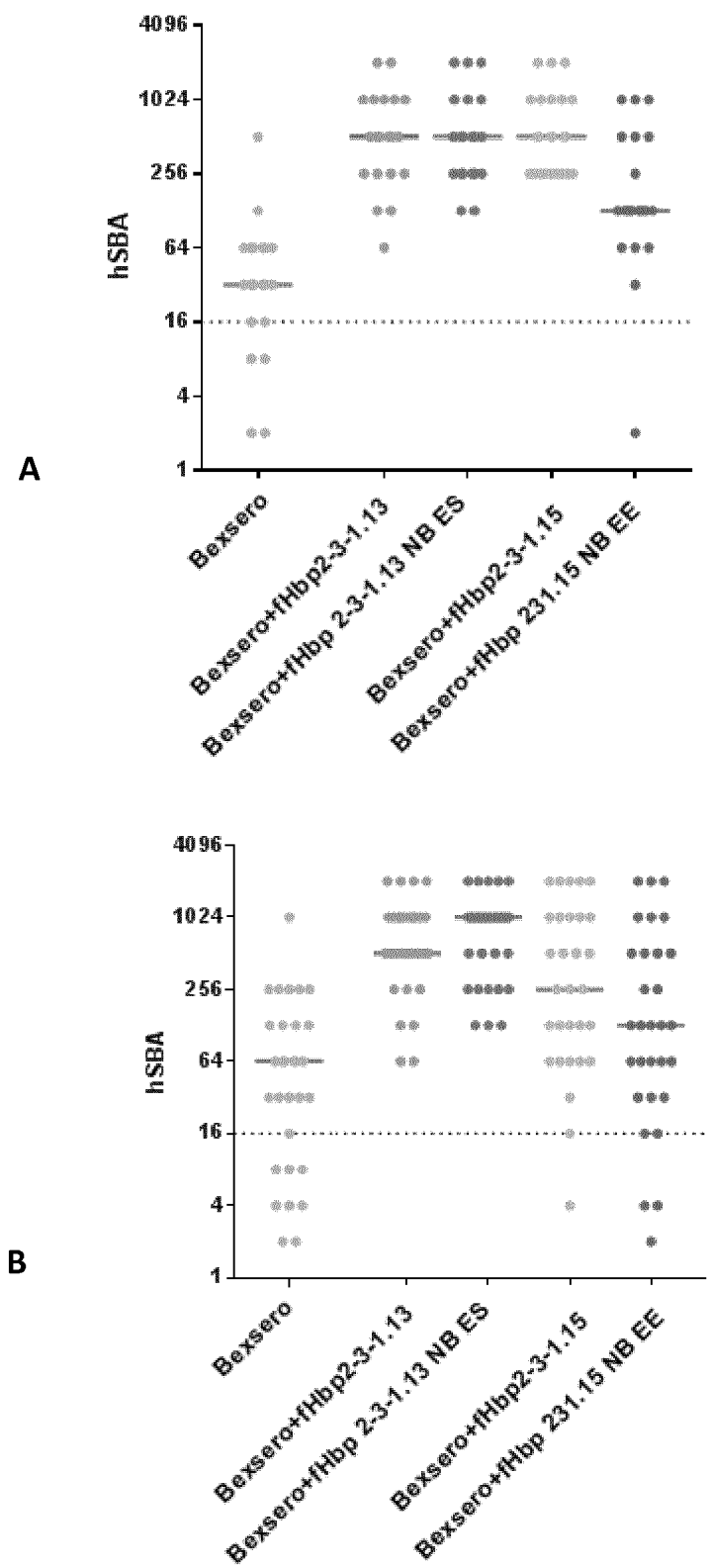

FIG. 17 shows pooled hSBA data by formulation for var2/3 (FIG. 17A) and v1.x (FIG. 17B) strain types. Sera collected from vaccinated rabbits were tested as pool against MenB strains, divided into var and var2/3 strains. In this figure, fHbp 2-3-1.13 refers to the fusion comprising wt v1.13, fHbp 2-3-1.13 NB ES refers to the 231.13_E211A/S216R fusion, fHbp 2-3-1.15 refers to the fusion comprising wt v1.15, and fHbp 2-3-1.15 NB EE refers to the 231.15_E214A/E235A fusion.

Figure 18:
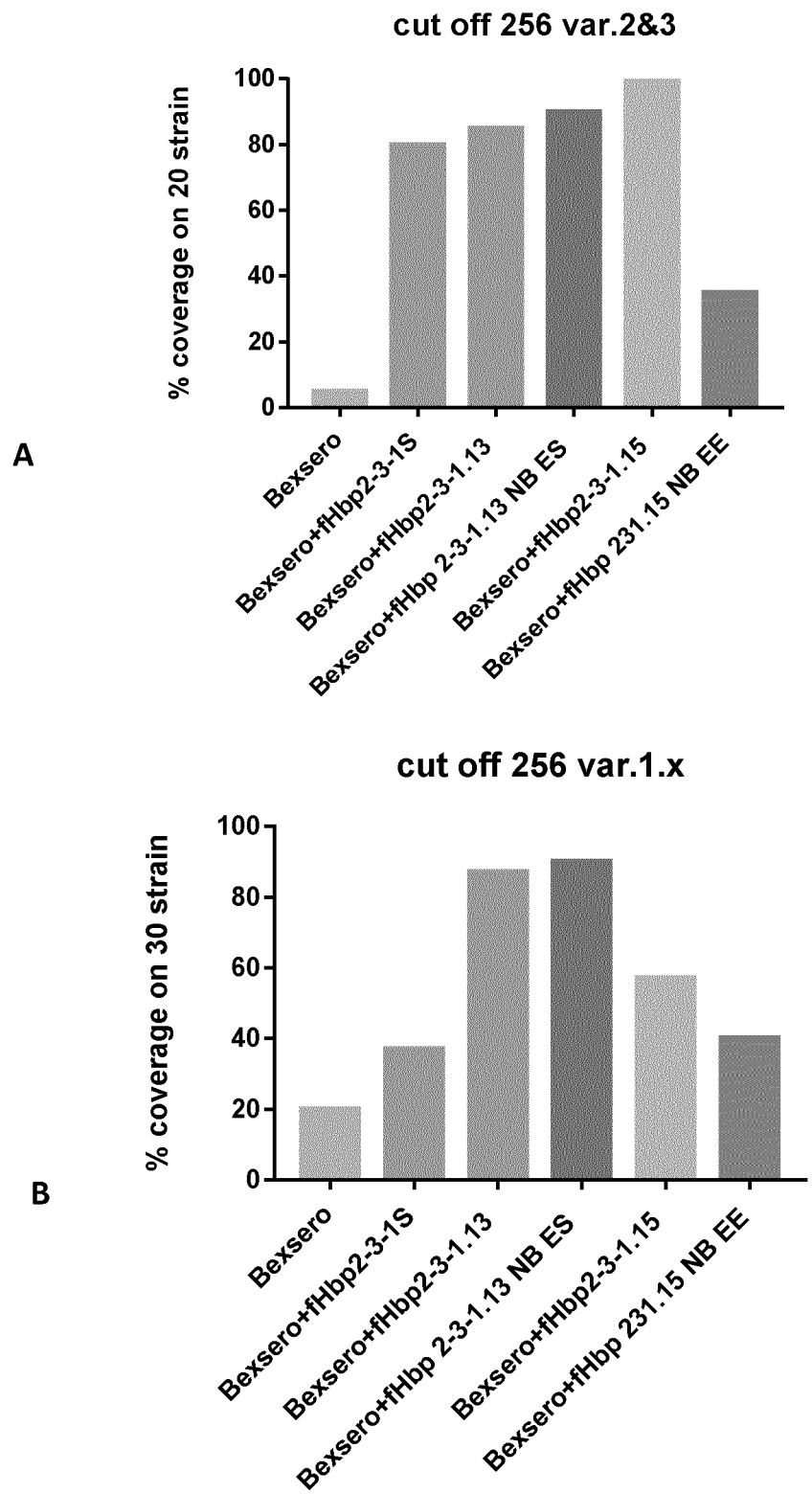

FIG. 18 shows the percentage of coverage provided by the vaccine formulations tested in rabbits against strains expressing fHbp var2/3 (A) and fHbp var (B). In this figure, fHbp 2-3-1S refers to the prior art fusion 231.1_R41S, fHbp 2-3-1.13 refers to the fusion comprising wt v1.13, fHbp 2-3-1.13 NB ES refers to the 231.13_E211A/S216R fusion, fHbp 2-3-1.13 NB EE refers to the 231.13_E211A/E232A fusion, fHbp 2-3-1.15 refers to the fusion comprising wt v1.15, and fHbp 2-3-1.15 NB EE refers to the 231.15_E214A/E235A fusion.

Figure 19:
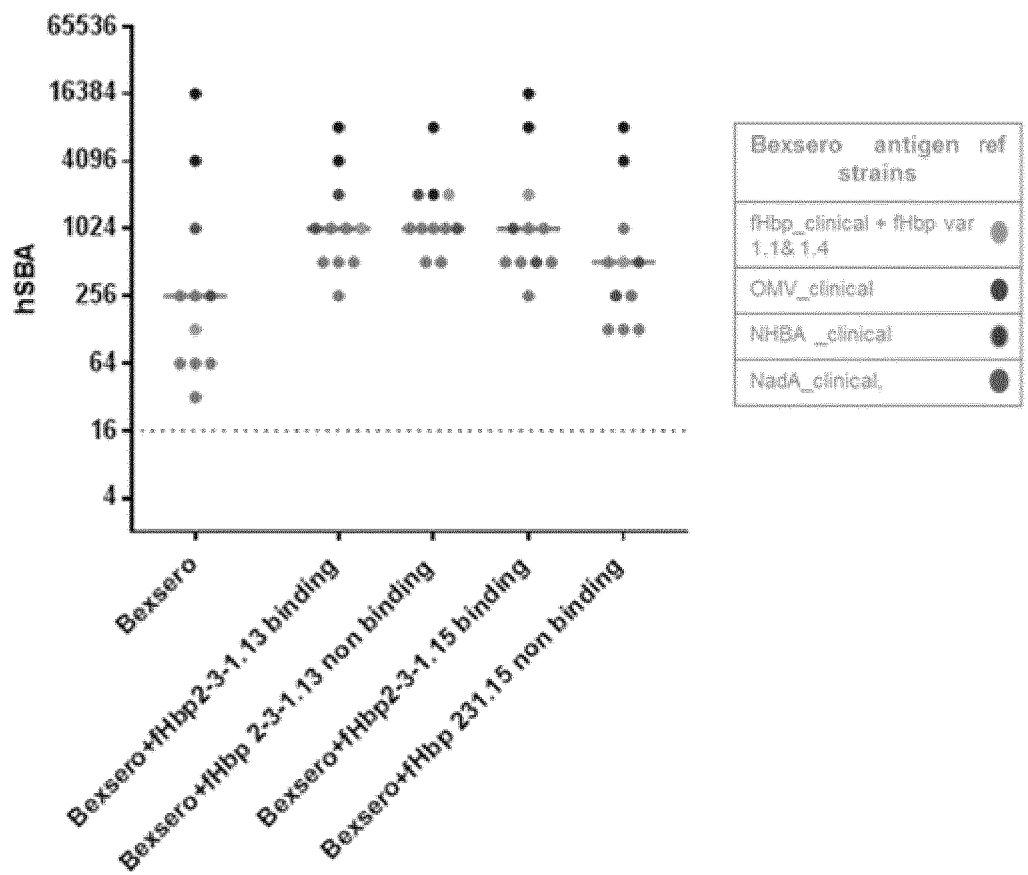

FIG. 19 shows hSBA titers from rabbit sera against 11 strains including BEXSERO reference stains and fHbp var1.1 and 1.4 strains. In this figure, fHbp 2-3-1.13 binding refers to the fusion comprising wt v1.13, fHbp 2-3-1.13 non-binding refers to the 231.13_E211A/S216R fusion, fHbp 2-3-1.15 binding refers to the fusion comprising wt v1.15, and fHbp 2-3-1.15 non-binding refers to the 231.15_E214A/E235A fusion.

Figure 20:
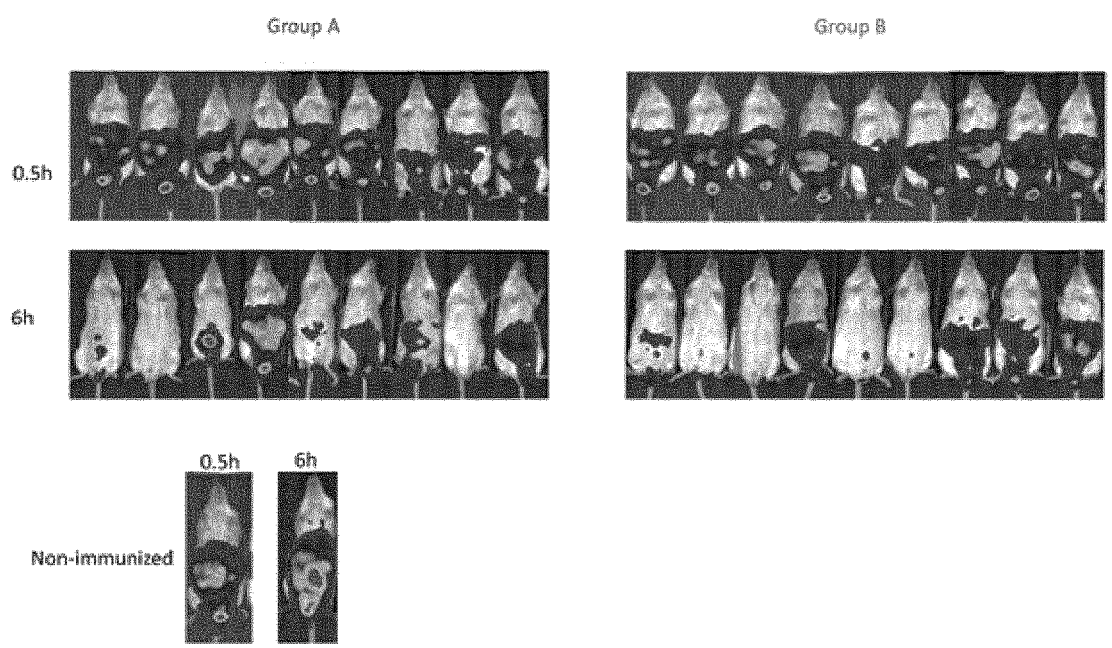

FIG. 20 shows dynamic imaging of bacterial challenge (bioluminescent MC58 cc32/var.1) in immunized and non-immunized mice. Mice in group A were immunized with 4CMenB+fHbp 23(S)1.13 wild type, whereas mice in group B were immunized with 4CMenB+fHbp 23(S)1.13_E211A/S216R. Non-immunized mice received only phosphate-buffered saline (PBS) as a control.

Figure 21:
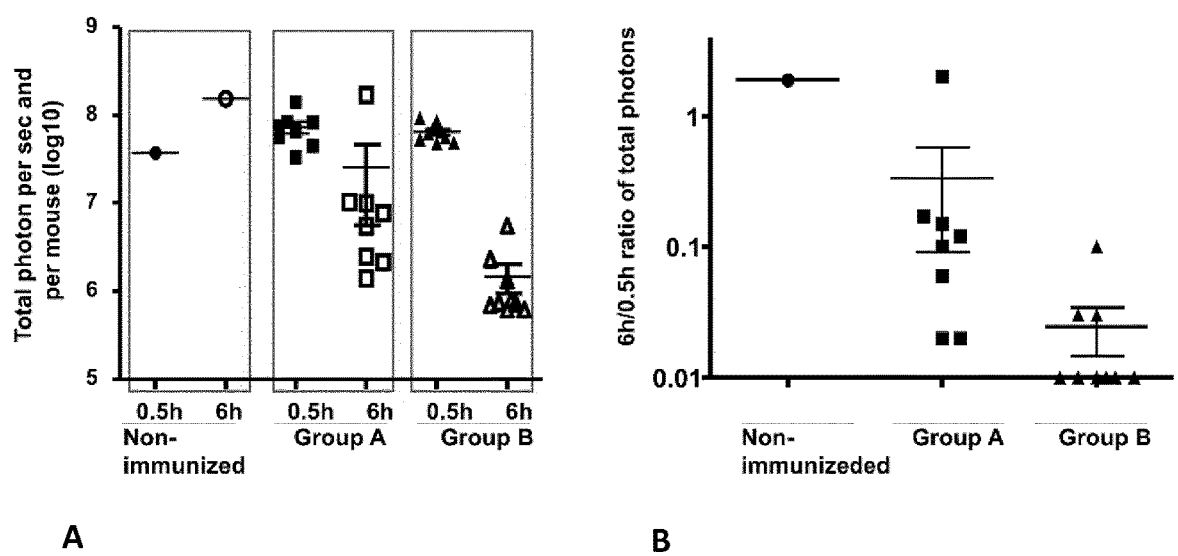

FIG. 21 (A and B) shows quantification and comparison of dynamic imaging signals of bacterial challenge (bioluminescent MC58 cc32/var.1) in immunized and non-immunized mice. The comparisons were performed using crude total signals (photons per sec and per mouse at each time point) (FIG. 21A) or per ratio of signals after 30 min and 6 h of bacterial challenge (FIG. 21B).

DETAILED DESCRIPTION OF THE INVENTION

Figure 1:
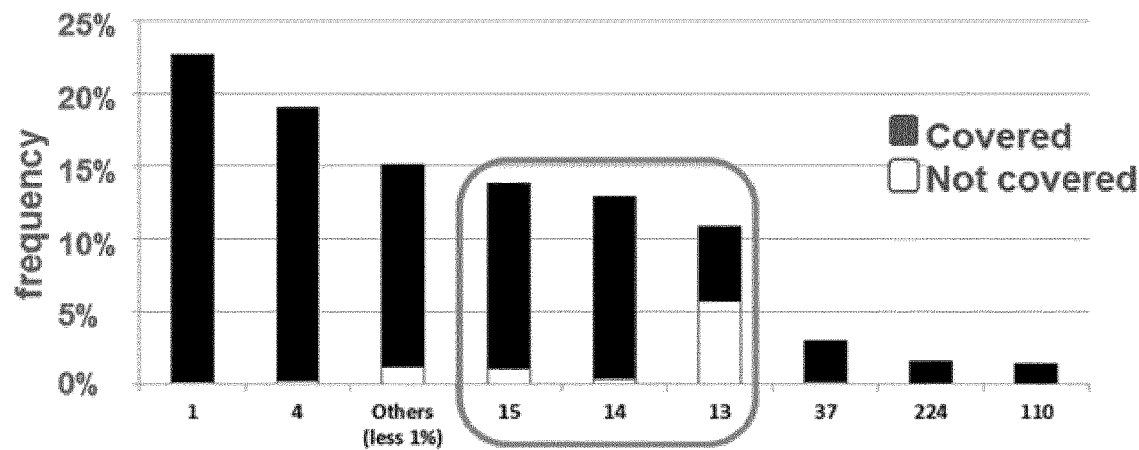
FIG. 1A is a graph showing the frequency of meningococcal B strains expressing fHbp v1.x sub-variants and indicates which of these v1.x sub-variants are covered (black) or not covered (white) by the 4CMenB vaccine.
FIG. 1B is a graph showing the frequency of meningococcal B strains carrying fHbp v2 and indicates which of these strains are covered (black) or not covered (white) by the 4 fHbp var1.1 (FIG. 16A); NZ98/254 for PorA P1.4 (FIG. 16B); M4407 for NHBA (FIG. 16C); and 96217 for NadA (FIG. 16D).
Figure 1:
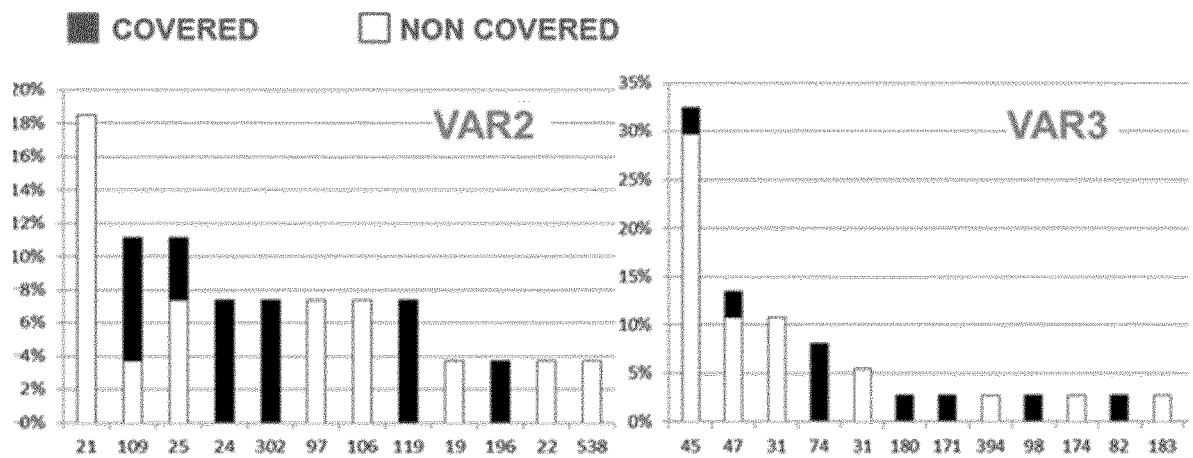

The lipoprotein factor H binding protein (fHbp) is expressed on the surface of all MenB strains. fHbp binds to the human complement regulatory protein factor H (hfH), forming a complex that protects the bacteria from complement-mediated killing and providing a survival mechanism for *N. meningitidis* in the human bloodstream. Antibodies against fHbp have a dual role: they are bactericidal per se, and by preventing binding to hfH they render strains more susceptible to bacterial killing. Reducing or abolishing the ability of fHbp to bind to hfH increases the immunogenicity of the fHbp antigen by preventing the formation of protective complexes between fHbp and hfH which have potential to mask fHbp epitopes and prevent antibody binding.

fHbp exists in three different genetic and immunogenic variants (v1, v2 and v3), with many subvariants. The majority of MenB strains that are not covered by 4CMenB express v2 or v3 fHbp, or v1 subvariants distantly related to var1.1. As shown in FIG. 1A, current epidemiology using the MATS approach (as described, for example by Medini et al. *Vaccine* 2015; 33(23); 2629-36) shows that strains with v1.1 and v1.4 are the most frequently occurring, followed by v1.15, v1.14 and v1.13. Antibodies raised against sub-variant fHbpv1.1, included in the 4CMenB vaccine, are highly cross-reactive with these most frequently occurring fHbp v1 sub-variants (v1.1 and v1.4) but are less cross-reactive with v1 sub-variants that are most distantly related to v1.1 (e.g. v1.15 and v1.13). This is illustrated in FIG. 1, as meningococcal B strain expressing fHbp v1.15 and v1.13 are the most frequently occurring strains that are not covered by the 4CMenB vaccine.

Furthermore, antibodies raised against sub-variant fHbpv1.1 included in the 4CMenB vaccine are poorly cross-reactive with fHbp v2 and v3 (Brunelli B et al., *Vaccine* 2011; 29:1072-1081). FIGS. 1B and 1C show gaps in the coverage of 4CMenB against some of the most frequently occurring strains expressing fHbp v2 or v3.

This means that 4CMenB coverage is not able to extend to some meningococcal strains carrying fHbp v2, v3, or strains carrying some v1 sub-variants.

The present invention provides mutated fHbp variant 1.13 or variant 1.15 (v1.13 or v1.15) polypeptides that are immunogenic and can be combined with existing meningococcal vaccines to provide improved *N. meningitidis* strain coverage.

In particular, the v1 polypeptides of the invention are subvariants of fHbp variant 1 that are genetically diverse compared with the fHbp v1.1 antigen included in 4CMenB.

Furthermore, the v1 polypeptides of the invention are mutated in order to reduce binding to hfH compared with the corresponding wildtype v1 polypeptide. In contrast, the fHbpv1.1 antigen included in BEXSERO, and the fHp v1.55 and v3.45 antigens included in TRUMENBA, do bind to hfH.

V1 polypeptides of the invention can be provided alone or as a component of a fusion protein, together with mutant forms of fHbp variants 2 and 3, which have been modified to improve stability and also to reduce fHbp binding. By providing a single fusion protein comprising these v2 and v3 antigens, together with a v1 antigen of the invention, the inventors have improved strain coverage relative to the existing licensed meningococcal B vaccines. For clarity, neither of the v2 and v3 antigens are present in, e.g., 4CMenB. The presence of v2 and v3 antigens within the fusion proteins of the present invention improves strain coverage as compared to, e.g., 4CMenB.

The v1 polypeptides and fusion proteins of the invention can be used alone or in combination with a meningococcal NHBA antigen, a meningococcal NadA antigen, a meningococcal fHbp antigen, and a meningococcal outer membrane vesicle (e.g., in combination with the BEXSERO composition), to provide a combined immunogenic composition having increased immunogenicity (due to the addition/inclusion of non-binding forms of fHbp variants) and increased *N. meningitidis* strain coverage (due to the addition of new fHbp variants/subvariants), compared with BEXSERO alone.

Mutant v1.13 Meningococcal fHbp Polypeptides

The present inventors have identified residues within the fHbp v1.13 sequence that can be modified to reduce binding to hfH. Such mutants are referred to herein as non-binding (NB) mutants. The inventors have also identified combinations of mutations in the v1.13 sequence that are particularly useful to reduce binding to hfH. fHbp v1.13 is also known in the art as fHbp variant B09.

The mature wild-type fHbp v1.13 lipoprotein from strain M982 (GenBank Accession No. AAR84475.1) has the following amino acid sequence, with an N-terminal poly-glycine signal sequence being underlined:

(SEQ ID NO: 1)
CSSGGGGVAADIGAGLADALTAPLDHKDKGLQSLTLDQSVRKNEKLKLA

AQGAEKTYGNGDSLNTGKLKNDKVSREDEIRQIEVDGKLITLESGEFQV

YKQSHSALTALQTEQVQDSEDSGKMVAKRQFRIGDIAGEHTSFDKLPKG

GSATYRGTAFGSDDAGGKLTYTIDFAAKQGHGKIEHLKSPELNVELATA

YIKPDEKRHAVISGSVLYNQDEKGSYSLGIFGGQAQEVAGSAEVETANG

IHHIGLAAKQ

The mature v1.13 lipoprotein differs from the full-length wild-type sequence in that the full-length polypeptide has an additional 19 residue N-terminal leader sequence, which is cleaved from the mature polypeptide. Thus, full-length wild-type fHbp v1.13 has the following amino acid sequence (with the N-terminal leader sequence shown in bold font):

(SEQ ID NO: 31)
MNRTAFCCFSLTAALILTACSSGGGGVAADIGAGLADALTAPLDHKDKG

LQSLTLDQSVRKNEKLKLAAQGAEKTYGNGDSLNTGKLKNDKVSRFDFI

RQIEVDGKLITLESGEFQVYKQSHSALTALQTEQVQDSEDSGKMVAKRQ

FRIGDIAGEHTSFDKLPKGGSATYRGTAFGSDDAGGKLTYTIDFAAKQG

HGKIEHLKSPELNVELATAYIKPDEKRHAVISGSVLYNQDEKGSYSLGI

FGGQAQEVAGSAEVETANGIHHIGLAAKQ

The ΔG form of the mature v1.13 lipoprotein lacks the N-terminal poly-glycine sequence of the mature polypeptide, i.e. it lacks the first 7 amino acids of SEQ ID NO: 1, and it lacks the first 26 amino acids of SEQ ID NO: 31:

(SEQ ID NO: 2)
VAADIGAGLADALTAPLDHKDKGLQSLTLDQSVRKNEKLKLAAQGAEKT

YGNGDSLNTGKLKNDKVSRFDFIRQIEVDGKLITLESGEFQVYKQSHSA

LTALQTEQVQDSEDSGKMVAKRQFRIGDIAGEHTSFDKLPKGGSATYRG

TAFGSDDAGGKLTYTIDFAAKQGHGKIEHLKSPELNVELATAYIKPDEK

RHAVISGSVLYNQDEKGSYSLGIFGGQAQEVAGSAEVETANGIHHIGLA

AKQ

Therefore, a first aspect of the invention provides a mutant v1.13 meningococcal fHbp polypeptide comprising an amino acid sequence having at least k % sequence identity to SEQ ID NO: 2, with the proviso that the amino acid sequence of said mutant v1.13 meningococcal fHbp polypeptide includes a substitution mutation at one or more of residues E211, S216 or E232 of SEQ ID NO: 2.

The value of k may be selected from 80, 85, 86, 87, 88, 89, 90, 91, 92, 93, 94, 95, 96, 97, 98, 99 or 100. It is preferably 80 (i.e. the mutant fHbp v1.13 amino acid sequence has at least 80% identity to SEQ ID NO: 2) and is more preferably 85, more preferably 90 and more preferably 95. Most preferably, the mutant fHbp v1.13 amino acid sequence has at least 97%, at least 98% or at least 99% identity to SEQ ID NO: 2.

Preferably, the amino acid sequence differs from SEQ ID NO: 2 by at least one or more of the substitutions E211A, S216R or E232A. More preferably, the amino acid sequence comprises substitutions at multiple residues selected from the following (i) E211A and E232A, or (ii) E211A and S216R. More preferably, the amino acid sequence comprises substitutions at residues E211A and S216R, relative to SEQ ID NO: 2.

Without wishing to be bound by theory, the substitution of glutamic acid (E) for alanine (A) at residue 211 of SEQ ID NO. 2 removes a negatively charged residue that is involved in hfH recruitment, thus contributing to the abrogation of fH binding. The substitution of arginine (R) for serine (S) at residue 216 of SEQ ID NO. 2 replaces the wildtype amino acid with a corresponding residue from *N. gonorrhoeae*, which does not bind hfH.

In preferred embodiments, a mutant v1.13 polypeptide of the invention has the amino acid sequence of SEQ ID NO: 3 (v1.13 AG E211A/E232A) or SEQ ID NO: 4 (v1.13 AG (E211A/S216R). More preferably, mutant v1.13 polypeptide of the invention has the amino acid sequence of SEQ ID NO: 4.

The mutant v1.13 polypeptide of the invention can, after administration to a host animal, preferably a mammal and more preferably a human, elicit antibodies which can recognise wild-type meningococcal fHbp polypeptides of SEQ ID NO: 1. These antibodies are ideally bactericidal (see below).

Mutant v1.15 Meningococcal fHbp Polypeptides

The present inventors have also identified residues within the fHbp v1.15 sequence that can be modified to prevent binding to hfH. Such mutants are referred to herein as non-binding (NB) mutants. The inventors have also identified combinations of mutations in the v1.15 sequence that are particularly useful to prevent binding to hfH. fHbp v1.15 is also known in the art as fHbp variant B44.

The mature wild-type fHbp v1.15 lipoprotein from strain NM452 (GenBank Accession No. ABL14232.1) has the following amino acid sequence, with an N-terminal poly-glycine signal sequence being underlined:

(SEQ ID NO: 5)
CSSGGGGSGGGGVAADIGAGLADALTAPLDHKDKGLKSLTLEDSISQNG

TLTLSAQGAERTFKAGDKDNSLNTGKLKNDKISRFDFIRQIEVDGQLIT

LESGEFQVYKQSHSALTALQTEQVQDSEHSGKMVAKRQFRIGDIVGEHT

SFGKLPKDVMATYRGTAFGSDDAGGKLTYTIDFAAKQGHGKIEHLKSPE

LNVDLAAADIKPDEKHHAVISGSVLYNQAEKGSYSLGIFGGQAQEVAGS

AEVETANGIRHIGLAAKQ

The mature v1.15 lipoprotein differs from the full-length wild-type sequence in that the full-length polypeptide has an additional 19 residue N-terminal leader sequence, which is cleaved from the mature polypeptide. Thus, full-length wild-type fHbp v1.15 has the following amino acid sequence (with the N-terminal leader sequence shown in bold font):

(SEQ ID NO: 32)
MNRTTFCCLSLTAALILTACSSGGGGSGGGGVAADIGAGLADALTAPLD

HKDKGLKSLTLEDSISQNGTLTLSAQGAERTFKAGDKDNSLNTGKLKND

KISRFDFIRQIEVDGQLITLESGEFQVYKQSHSALTALQTEQVQDSEHS

GKMVAKRQERIGDIVGEHTSFGKLPKDVMATYRGTAFGSDDAGGKLTYT

-continued

```
IDFAAKQGHGKIEHLKSPELNVDLAAADIKPDEKHHAVISGSVLYNQAE

KGSYSLGIFGGQAQEVAGSAEVETANGIRHIGLAAKQ
```

The ΔG form of the mature v1.15 lipoprotein lacks the N-terminal poly-glycine sequence, i.e. it lacks the first 12 amino acids of SEQ ID NO: 5, and it lacks the first 31 amino acids of SEQ ID NO: 32:

```
                                         (SEQ ID NO: 6)
VAADIGAGLADALTAPLDHKDKGLKSLTLEDSISQNGTLTLSAQGAERT

FKAGDKDNSLNTGKLKNDKISRFDFIRQIEVDGQLITLESGEFQVYKQS

HSALTALQTEQVQDSEHSGKMVAKRQFRIGDIVGEHTSFGKLPKDVMAT

YRGTAFGSDDAGGKLTYTIDFAAKQGHGKIEHLKSPELNVDLAAADIKP

DEKHHAVISGSVLYNQAEKGSYSLGIFGGQAQEVAGSAEVETANGIRHI

GLAAKQ
```

Therefore, a second aspect of the invention provides a mutant v1.15 meningococcal fHbp polypeptide comprising an amino acid sequence having at least k % sequence identity to SEQ ID NO: 6, with the proviso that the amino acid sequence of said mutant v1.15 meningococcal fHbp polypeptide includes a substitution mutation at one or more of residues E214, S219 or E235 of SEQ ID NO: 6

The value of k may be selected from 80, 85, 86, 87, 88, 89, 90, 91, 92, 93, 94, 95, 96, 97, 98, 99 or 100. It is preferably 80 (i.e. the mutant fHbp v1.15 amino acid sequence has at least 80% identity to SEQ ID NO: 6) and is more preferably 85, more preferably 90 and more preferably 95. Most preferably, the mutant fHbp v1.15 amino acid sequence has at least 97%, at least 98% or at least 99% identity to SEQ ID NO: 6.

Preferably, the amino acid sequence differs from SEQ ID NO: 6 by at least one or more of the substitutions E214A, S219R or E235A. More preferably, the amino acid sequence comprises substitutions at residues selected from the following: (i) S219R, (ii) E214A and S219R, and (iii) E214A and E235A.

In preferred embodiments, a mutant v1.15 polypeptide of the invention has the amino acid sequence of SEQ ID NO: 7 (v.1.15_S219R), SEQ ID NO: 8 (v1.15_E214A/S219R) or SEQ ID NO: 9 (v1.15_E214A/E235A).

The mutant v1.15 polypeptide of the invention can, after administration to a host animal, preferably a mammal and more preferably a human, elicit antibodies which can recognise wild-type meningococcal fHbp polypeptides of SEQ ID NO: 5. These antibodies are ideally bactericidal (see below).

Fusion Polypeptide

The invention also provides a fusion polypeptide comprising all three of v1, v2 and v3 meningococcal fHbp polypeptides, wherein the variant fHbp sequences are in the order v2-v3-v1 from N- to C-terminus. In a preferred embodiment the fHbp fusion polypeptide has an amino acid sequence of formula $NH_2$-A-[-X-L]$_3$-B—COOH, wherein each X is a different variant fHbp sequence, L is an optional linker amino acid sequence, A is an optional N terminal amino acid sequence, and B is an optional C terminal amino acid sequence.

The v1 fHbp polypeptide component of the fusion of the invention is either a mutant v1.13 fHbp polypeptide or mutant v1.13 fHbp polypeptide as described above.

The v2 and v3 fHbp polypeptide components of the fusion of the invention are preferably mutant v2 and v3 polypeptides having enhanced stability and reduced ability to bind to hfH, compared to the wild-type v2 and v3 polypeptides. As explained above, reducing fHbp binding to hfH is advantageous because it prevents the formation of protective complexes between fHbp and hfH which can mask fHbp epitopes, and thereby increases the immunogenicity of the polypeptide antigen.

The inventors have previously identified residues within the v2 and v3 sequences which can be modified to increase the stability of the polypeptide and also to reduce binding to hfH. These mutated v2 and v3 sequences are described in detail in WO2015/128480.

Full-length wild-type fHbp v2 from strain 2996 has the following amino acid sequence (leader sequence shown in bold font and poly-glycine sequence being underlined):

```
                                        (SEQ ID NO: 10)
MNRTAFCCLSLTAALILTACSSGGGGVAADIGAGLADALTAPLDHKDKS

LQSLTLDQSVRKNEKLKLAAQGAEKTYGNGDSLNTGKLKNDKVSRFDFI

RQIEVDGQLITLESGEFQIYKQDHSAVVALQIEKINNPDKIDSLINQRS

FLVSGLGGEHTAFNQLPDGKAEYHGKAFSSDDAGGKLTYTIDFAAKQGH

GKIEHLKTPEQNVELAAAELKADEKSHAVILGDTRYGSEEKGTYHLALF

GDRAQEIAGSATVKIGEKVHEIGIAGKQ
```

The mature lipoprotein lacks the first 19 amino acids of SEQ ID NO: 10:

```
                                        (SEQ ID NO: 11)
CSSGGGGVAADIGAGLADALTAPLDHKDKSLQSLTLDQSVRKNEKLKLA

AQGAEKTYGNGDSLNTGKLKNDKVSRFDEIRQIEVDGQLITLESGEFQI

YKQDHSAVVALQIEKINNPDKIDSLINQRSFLVSGLGGEHTAFNQLPDG

KAEYHGKAFSSDDAGGKLTYTIDFAAKQGHGKIEHLKTPEQNVELAAAE

LKADEKSHAVILGDTRYGSEEKGTYHLALFGDRAQEIAGSATVKIGEKV

HEIGIAGKQ
```

The ΔG form of SEQ ID NO: 10 lacks the first 26 amino acids:

```
                                        (SEQ ID NO: 12)
VAADIGAGLADALTAPLDHKDKSLQSLTLDQSVRKNEKLKLAAQGAEKT

YGNGDSLNTGKLKNDKVSRFDFIRQIEVDGQLITLESGEFQIYKQDHSA

VVALQIEKINNPDKIDSLINQRSFLVSGLGGEHTAFNQLPDGKAEYHGK

AFSSDDAGGKLTYTIDFAAKQGHGKIEHLKTPEQNVELAAAELKADEKS

HAVILGDTRYGSEEKGTYHLALFGDRAQEIAGSATVKIGEKVHEIGIAG

KQ
```

In a preferred embodiment, the fusion polypeptide of the invention comprises a mutant v2 fHbp polypeptide comprising an amino acid sequence having at least k % sequence identity to SEQ ID NO: 12, with the proviso that the v2 fHbp amino acid sequence includes a substitution mutation at residues S32 and L123 of SEQ ID NO: 12. Preferably the substitutions are S32V and L123R.

The value of k may be selected from 80, 85, 86, 87, 88, 89, 90, 91, 92, 93, 94, 95, 96, 97, 98, 99 or 100. It is preferably 80 (i.e. the mutant fHbp v2 amino acid sequence has at least 80% identity to SEQ ID NO: 12) and is more preferably 85, more preferably 90 and more preferably 95.

In some embodiments, the fHbp v2 polypeptide included in the fusion protein of the invention is truncated relative to SEQ ID NO: 12. Compared to the wild-type mature sequence, SEQ ID NO: 12 is already truncated at the N-terminus up to and including the poly-glycine sequence (compare SEQ ID NOs: 11 and 12), but SEQ ID NO: 12 can be truncated at the C-terminus and/or further truncated at the N-terminus.

In a preferred embodiment, the v2 fHbp polypeptide included in the fusion protein of the invention comprises or consists of the amino acid sequence of SEQ ID NO: 16.

The v2 fHbp polypeptide included in the fusion protein of the invention has, under the same experimental conditions, a higher stability than the same polypeptide but without the sequence differences at residues S32 and L123 e.g. higher stability than a wild-type meningococcal polypeptide consisting of SEQ ID NO: 10. The S32V mutation stabilizes the structure by introducing favourable hydrophobic interactions. The L123R mutation abrogates fH binding by introducing clashes with fH and unfavorable charges.

The stability enhancement can be assessed using differential scanning calorimetry (DSC) e.g. as discussed in Johnson (2013) *Arch Biochem Biophys* 531:100-9 and Bruylants et al. *Current Medicinal Chemistry* 2005; 12:2011-20. DSC has previously been used to assess the stability of v2 fHbp (Johnson et al. *PLoS Pathogen* 2012; 8: e1002981). Suitable conditions for DSC to assess stability can use 20 µM of polypeptide in a buffered solution (e.g. 25 mM Tris) with a pH between 6 and 8 (e.g. 7-7.5) with 100-200 mM NaCl (e.g. 150 mM).

The increase in stability is evidenced by an at least 5° C., e.g. at least 10° C., 15° C., 20° C., 25° C., 30° C., 35° C. or more, increase in thermal transition midpoint (Tm) of at least one peak as compared to wild-type when assessed by DSC. Wild-type fHbp shows two DSC peaks during unfolding (one for the N-terminal domain and one for the C-terminal domain) and, where a v2 polypeptide included in the fusion protein of the invention includes both such domains, an "increase in stability" refers to an at least 5° C. increase in the Tm of the N-terminal domain. Tm of the N-terminal domain can occur at or even below 40° C. with wild-type v2 sequences (Johnson et al. (2012) *PLoS Pathogen* 8: e1002981), whereas C-terminal domains can have a Tm of 80° C. or more. Thus, the mutant fHbp v2 amino acid sequence included in the fusion protein of the invention preferably has a N-terminal domain with a Tm of at least 45° C. e.g. ≥50° C., ≥55° C., ≥60° C., ≥65° C., ≥70° C., ≥75° C., or even ≥80° C.

Full-length wild-type fHbp v3 from strain M1239 has the following amino acid sequence (leader sequence shown in bold font and poly-glycine sequence being underlined):

(SEQ ID NO: 13)
MNRTAFCCLSLTTALILTA<u>CSSGGGGSGGGG</u>VAADIGTGLADALTAPLD

HKDKGLKSLTLEDSIPQNGTLTLSAQGAEKTFKAGDKDNSLNTGKLKND

KISRFDFVQKIEVDGQTITLASGEFQIYKQNHSAVVALQIEKINNPDKT

DSLINQRSFLVSGLGGEHTAFNQLPGGKAEYHGKAFSSDDPNGRLHYSI

DFTKKQGYGRIEHLKTLEQNVELAAAELKADEKSHAVILGDTRYGSEEK

GTYHLALFGDRAQEIAGSATVKIGEKVHEIGIAGKQ

The mature lipoprotein lacks the first 19 amino acids of SEQ ID NO: 13:

(SEQ ID NO: 14)
CSSGGGGSGGGGVAADIGTGLADALTAPLDHKDKGLKSLTLEDSIPQNG

TLTLSAQGAEKTFKAGDKDNSLNTGKLKNDKISRFDFVQKIEVDGQTIT

LASGEFQIYKQNHSAVVALQIEKINNPDKTDSLINQRSFLVSGLGGEHT

AFNQLPGGKAEYHGKAFSSDDPNGRLHYSIDFTKKQGYGRIEHLKTLEQ

NVELAAAELKADEKSHAVILGDTRYGSEEKGTYHLALFGDRAQEIAGSA

TVKIGEKVHEIGIAGKQ

The ΔG form of SEQ ID NO: 13 lacks the first 31 amino acids (i.e. lacks the signal sequence and the poly-glycine sequence):

(SEQ ID NO: 15)
VAADIGTGLADALTAPLDHKDKGLKSLTLEDSIPQNGTLTLSAQGAEKT

FKAGDKDNSLNTGKLKNDKISRFDFVQKIEVDGQTITLASGEFQIYKQN

HSAVVALQIEKINNPDKTDSLINQRSFLVSGLGGEHTAFNQLPGGKAEY

HGKAFSSDDPNGRLHYSIDFTKKQGYGRIEHLKTLEQNVELAAAELKAD

EKSHAVILGDTRYGSEEKGTYHLALFGDRAQEIAGSATVKIGEKVHEIG

IAGKQ

In a preferred embodiment, the fusion polypeptide of the invention comprises a mutant v3 fHbp polypeptide comprising an amino acid sequence having at least k % sequence identity to SEQ ID NO: 15, with the proviso that the v3 fHbp amino acid sequence includes substitution mutations at residues S32 and L126 of SEQ ID NO: 15. Preferably the substitutions are S32V and L126R. The value of k may be selected from 80, 85, 86, 87, 88, 89, 90, 91, 92, 93, 94, 95, 96, 97, 98, 99 or 100. It is preferably 80 (i.e. the mutant fHbp v2 amino acid sequence has at least 80% identity to SEQ ID NO: 15) and is more preferably 85, more preferably 90 and more preferably 95.

In some embodiments, the fHbp v3 polypeptide included in the fusion protein of the invention is truncated relative to SEQ ID NO: 15. Compared to the wild-type mature sequence, SEQ ID NO: 15 is already truncated at the N-terminus up to and including the poly-glycine sequence (compare SEQ ID NOs: 14 and 15), but SEQ ID NO: 15 can be truncated at the C-terminus and/or further truncated at the N-terminus.

In a preferred embodiment, the v3 fHbp polypeptide included in the fusion protein of the invention comprises or consists of the amino acid sequence of SEQ ID NO: 17.

The v3 fHbp polypeptide included in the fusion protein of the invention has, under the same experimental conditions, a higher stability than the same polypeptide but without the sequence differences at residues S32 and L126 e.g. higher stability than a wild-type meningococcal polypeptide consisting of SEQ ID NO: 13. The S32V mutation stabilizes the structure by introducing favorable hydrophobic interactions. The L126R mutation abrogates fH binding by introducing clashes with fH and unfavorable charges.

The stability enhancement can be assessed using differential scanning calorimetry (DSC) e.g. as discussed in Johnson (2013) *Arch Biochem Biophys* 531:100-9 and Bruylants et al. (2005) *Current Medicinal Chemistry* 12:2011-20. DSC has previously been used to assess the stability of v3 fHbp (van der Veen et al. (2014) *Infect Immun* PMID 24379280). Suitable conditions for DSC to assess stability can use 20 µM of polypeptide in a buffered solution (e.g. 25 mM Tris) with a pH between 6 and 8 (e.g. 7-7.5) with 100-200 mM NaCl (e.g. 150 mM).

The increase in stability is evidenced by an at least 5° C., e.g. at least 10° C., 15° C., 20° C., 25° C., 30° C., 35° C. or more, increase in thermal transition midpoint (Tm) of at least one peak as compared to wild-type when assessed by DSC. Wild-type fHbp shows two DSC peaks during unfolding (one for the N-terminal domain and one for the C-terminal domain) and, where a v3 polypeptide included in the fusion protein of the invention includes both such domains, an "increase in stability" refers to an at least 5° C. increase in the Tm of the N-terminal domain. Tm of the N terminal domain can occur at around 60° C. or less with wild-type v3 sequences (Johnson et al. (2012) *PLoS Pathogen* 8:e1002981), whereas C-terminal domains can have a Tm of 80° C. or more. Thus, the mutant fHbp v3 amino acid sequence of the invention preferably has a N-terminal domain with a Tm of at least 65° C. e.g. ≥70° C., ≥75° C., or even ≥80° C.

As described above, in a preferred embodiment the fHbp fusion polypeptide has an amino acid sequence of formula $NH_2$-A-[-X-L]$_3$-B—COOH, wherein each X is a different variant fHbp sequence and L is an optional linker amino acid sequence. In a preferred embodiment, the linker amino acid sequence "L" is a glycine polymer or glycine-serine polymer linker. Exemplary linkers include, but are not limited to, "GGSG", "GGSGG", "GSGSG", "GSGGG", "GGGSG", "GSSSG" and "GSGGGG". Other suitable glycine or glycine-serine polymer linkers will be apparent to the skilled person. In a preferred fusion polypeptide according to the invention, the v2 and v3 sequences and the v3 and v1 sequences are connected by the glycine-serine polymer linker "GSGGGG".

In a preferred embodiment, the fusion polypeptide of the invention comprises or consists of one of the following amino acid sequences (glycine-serine linker sequences are underlined and mutated residues are indicated in bold font):

fHbp 23S_1.13_E211A/E232A (SEQ ID NO: 18)

VAADIGAGLADALTAPLDHKDKSLQSLTLDQVVRKNEKLKLAAQGAEKTYGNGDSLNTGKLKNDKVSRFDFIR

QIEVDGQLITLESGEFQIYKQDHSAVVALQIEKINNPDKIDSLINQRSFRVSGLGGEHTAFNQLPDGKAEYHG

KAFSSDDAGGKLTYTIDFAAKQGHGKIEHLKTPEQNVELAAAELKADEKSHAVILGDTRYGSEEKGTYHLALE

GDRAQEIAGSATVKIGEKVHEIGIAGKQGSGGGGVAADIGTGLADALTAPLDHKDKGLKSLTLEDVIPQNGTL

TLSAQGAEKTFKAGDKDNSLNTGKLKNDKISRFDFVQKIEVDGQTITLASGEFQIYKQNHSAVVALQIEKINN

PDKTDSLINQRSFRVSGLGGEHTAFNQLPGGKAEYHGKAFSSDDPNGRLHYSIDFTKKQGYGRIEHLKTLEQN

VELAAAELKADEKSHAVILGDTRYGSEEKGTYHLALFGDRAQEIAGSATVKIGEKVHEIGIAGKQGSGGGGVA

ADIGAGLADALTAPLDHKDKGLQSLTLDQSVRKNEKLKLAAQGAEKTYGNGDSLNTGKLKNDKVSRFDFIRQI

EVDGKLITLESGEFQVYKQSHSALTALQTEQVQDSEDSGKMVAKRQFRIGDIAGEHTSFDKLPKGGSATYRGT

AFGSDDAGGKLTYTIDFAAKQGHGKIEHLKSPELNVELATAYIKPDEKRHAVISGSVLYNQDAKGSYSLGIFG

GQAQEVAGSAAVETANGIHHIGLAAKQ fHbp 23S_1.13_E211A/S216R (SEQ ID NO: 19)

VAADIGAGLADALTAPLDHKDKSLQSLTLDQVVRKNEKLKLAAQGAEKTYGNGDSLNTGKLKNDKVSRFDFIR

QIEVDGQLITLESGEFQIYKQDHSAVVALQIEKINNPDKIDSLINQRSFRVSGLGGEHTAFNQLPDGKAEYHG

KAFSSDDAGGKLTYTIDFAAKQGHGKIEHLKTPEQNVELAAAELKADEKSHAVILGDTRYGSEEKGTYHLALE

GDRAQEIAGSATVKIGEKVHEIGIAGKQGSGGGGVAADIGTGLADALTAPLDHKDKGLKSLTLEDVIPQNGTL

TLSAQGAEKTFKAGDKDNSLNTGKLKNDKISRFDFVQKIEVDGQTITLASGEFQIYKQNHSAVVALQIEKINN

PDKTDSLINQRSFRVSGLGGEHTAFNQLPGGKAEYHGKAFSSDDPNGRLHYSIDFTKKQGYGRIEHLKTLEQN

VELAAAELKADEKSHAVILGDTRYGSEEKGTYHLALFGDRAQEIAGSATVKIGEKVHEIGIAGKQGSGGGGVA

ADIGAGLADALTAPLDHKDKGLQSLTLDQSVRKNEKLKLAAQGAEKTYGNGDSLNTGKLKNDKVSRFDFIRQI

EVDGKLITLESGEFQVYKQSHSALTALQTEQVQDSEDSGKMVAKRQFRIGDIAGEHTSFDKLPKGGSATYRGT

AFGSDDAGGKLTYTIDFAAKQGHGKIEHLKSPELNVELATAYIKPDEKRHAVISGSVLYNQDAKGSYRLGIFG

GQAQEVAGSAEVETANGIHHIGLAAKQ fHbp_23S_1.15_S231R (SEQ ID NO: 20)

VAADIGAGLADALTAPLDHKDKSLQSLTLDQVVRKNEKLKLAAQGAEKTYGNGDSLNTGKLKNDKVSRFDFIR

QIEVDGQLITLESGEFQIYKQDHSAVVALQIEKINNPDKIDSLINQRSFRVSGLGGEHTAFNQLPDGKAEYHG

KAFSSDDAGGKLTYTIDFAAKQGHGKIEHLKTPEQNVELAAAELKADEKSHAVILGDTRYGSEEKGTYHLALE

-continued

GDRAQEIAGSATVKIGEKVHEIGIAGKQGSGGGGVAADIGTGLADALTAPLDHKDKGLKSLTLEDVIPQNGTL

TLSAQGAEKTFKAGDKDNSLNTGKLKNDKISRFDFVQKIEVDGQTITLASGEFQIYKQNHSAVVALQIEKINN

PDKTDSLINQRSFRVSGLGGEHTAFNQLPGGKAEYHGKAFSSDDPNGRLHYSIDFTKKQGYGRIEHLKTLEQN

VELAAAELKADEKSHAVILGDTRYGSEEKGTYHLALFGDRAQEIAGSATVKIGEKVHEIGIAGKQGSGGGGVA

ADIGAGLADALTAPLDHKDKGLKSLTLEDSISQNGTLTLSAQGAERTFKAGDKDNSLNTGKLKNDKISRFDFI

RQIEVDGQLITLESGEFQVYKQSHSALTALQTEQVQDSEHSGKMVAKRQFRIGDIVGEHTSFGKLPKDVMATY

RGTAFGSDDAGGKLTYTIDFAAKQGHGKIEHLKSPELNVDLAAADIKPDEKHHAVISGSVLYNQAEKGSYRLG

IFGGQAQEVAGSAEVETANGIRHIGLAAKQ fHbp_23S_1.15_E214A/S219R
(SEQ ID NO: 21)

VAADIGAGLADALTAPL amino acid sequence of SEQ ID NO. 34 at the N-terminal of the fusion polypeptide, i.e. the amino acid sequence of SEQ ID NO. 34 is added to the N-terminal of the fHbp v2 component of the fusion polypeptide.

Bactericidal Responses

Preferred v1.13, v1.15 and/or fusion polypeptides of the invention can elicit antibody responses that are bactericidal against meningococci. Bactericidal antibody responses are conveniently measured in mice and are a standard indicator of vaccine efficacy (e.g. see end-note 14 of Pizza et al. (2000) *Science* 287:1816-1820; also WO2007/028408).

Polypeptides of the first embodiment invention can preferably elicit an antibody response which is bactericidal against a *N. meningitidis* strain which expresses a v1.13 fHbp sequence.

Preferred polypeptides of the first embodiment invention can elicit antibodies in a mouse which are bactericidal against a *N. meningitidis* strain which expresses a v1.13 fHbp sequence in a serum bactericidal assay.

Polypeptides of the second embodiment invention can preferably elicit an antibody response which is bactericidal against a *N. meningitidis* strain which expresses a v1.15 fHbp sequence.

Preferred polypeptides of the second embodiment invention can elicit antibodies in a mouse which are bactericidal against a *N. meningitidis* strain which expresses a v1.15 fHbp sequence in a serum bactericidal assay.

For example, an immunogenic composition comprising these polypeptides can provide a serum bactericidal titer of ≥1:4 using the Goldschneider assay with human complement [Goldschneider et al. (1969) *J. Exp. Med.* 129:1307-26, Santos et al. (2001) *Clinical and Diagnostic Laboratory Immunology* 8:616-23, and Frasch et al. (2009) Vaccine 27S:B112-6], and/or providing a serum bactericidal titer of ≥1:128 using baby rabbit complement.

Polypeptides

Polypeptides of the invention can be prepared by various means e.g. by chemical synthesis (at least in part), by digesting longer polypeptides using proteases, by translation from RNA, by purification from cell culture (e.g. from recombinant expression or from *N. meningitidis* culture), etc. Heterologous expression in an *E. coli* host is a preferred expression route.

Polypeptides of the invention are ideally at least 100 amino acids long e.g. 150aa, 175aa, 200aa, 225aa, or longer. They include a mutant fHbp v1, v2 and/or v3 amino acid sequence, and the mutant fHbp v1, v2 or v3 amino acid sequence should similarly be at least 100 amino acids long e.g. 150aa, 175aa, 200aa, 225aa, or longer.

The fHbp is naturally a lipoprotein in *N. meningitidis*. It has also been found to be lipidated when expressed in *E. coli* with its native leader sequence or with heterologous leader sequences. Polypeptides of the invention may have an N-terminus cysteine residue, which may be lipidated e.g. comprising a palmitoyl group, usually forming tripalmitoyl-S-glyceryl-cysteine. In other embodiments the polypeptides are not lipidated.

Polypeptides are preferably prepared in substantially pure or substantially isolated form (i.e. substantially free from other Neisserial or host cell polypeptides). In general, the polypeptides are provided in a non-naturally occurring environment e.g. they are separated from their naturally-occurring environment. In certain embodiments, the polypeptide is present in a composition that is enriched for the polypeptide as compared to a starting material. Thus, purified polypeptide is provided, whereby purified means that the polypeptide is present in a composition that is substantially free of other expressed polypeptides, whereby substantially free is meant that more than 50% (e.g. ≥75%, ≥80%, ≥90%, ≥95%, or ≥99%) of total polypeptide in the composition is a polypeptide of the invention.

Polypeptides can take various forms (e.g. native, fusions, glycosylated, non-glycosylated, lipidated, disulfide bridges, etc.).

If a polypeptide of the invention is produced by translation in a biological host then a start codon is required, which will provide a N-terminus methionine in most hosts. Thus, a polypeptide of the invention will, at least at a nascent stage, include a methionine residue upstream of said SEQ ID NO sequence.

Cleavage of nascent sequences means that the mutant fHbp v1, v2 or v3 amino acid sequence might itself provide the polypeptide's N-terminus. In other embodiments, however, a polypeptide of the invention can include a N-terminal sequence upstream of the mutant fHbp v1, v2 or v3 amino acid sequence. In some embodiments the polypeptide has a single methionine at the N-terminus immediately followed by the mutant fHbp v1, v2 or v3 amino acid sequence; in other embodiments a longer upstream sequence may be used. Such an upstream sequence may be short (e.g. 40 or fewer amino acids i.e. 39, 38, 37, 36, 35, 34, 33, 32, 31, 30, 29, 28, 27, 26, 25, 24, 23, 22, 21, 20, 19, 18, 17, 16, 15, 14, 13, 12, 11, 10, 9, 8, 7, 6, 5, 4, 3, 2, 1). Examples include leader sequences to direct protein trafficking, or short peptide sequences which facilitate cloning or purification (e.g. a histidine tag i.e. $His_n$ where n=4, 5, 6, 7, 8, 9, 10 or more). Other suitable N-terminal amino acid sequences will be apparent to those skilled in the art.

A polypeptide of the invention may also include amino acids downstream of the final amino acid of the mutant fHbp v1, v2 or v3 amino acid sequence. Such C-terminal extensions may be short (e.g. 40 or fewer amino acids i.e. 39, 38, 37, 36, 35, 34, 33, 32, 31, 30, 29, 28, 27, 26, 25, 24, 23, 22, 21, 20, 19, 18, 17, 16, 15, 14, 13, 12, 11, 10, 9, 8, 7, 6, 5, 4, 3, 2, 1). Examples include sequences to direct protein trafficking, short peptide sequences which facilitate cloning or purification (e.g. comprising a histidine tag i.e. $His_n$ where n=4, 5, 6, 7, 8, 9, 10 or more), or sequences which enhance polypeptide stability. Other suitable C-terminal amino acid sequences will be apparent to those skilled in the art.

In some embodiments, the invention excludes polypeptides which include a histidine tag (cf. Johnson et al. (2012) *PLoS Pathogen* 8:e1002981, and Pajon et al. (2012) *Infect Immun* 80:2667-77), and in particular a hexahistidine tag at the C-terminus.

The term "polypeptide" refers to amino acid polymers of any length. The polymer may be linear or branched, it may comprise modified amino acids, and it may be interrupted by non-amino acids. The terms also encompass an amino acid polymer that has been modified naturally or by intervention; for example, disulfide bond formation, glycosylation, lipidation, acetylation, phosphorylation, or any other manipulation or modification, such as conjugation with a labeling component. Also included within the definition are, for example, polypeptides containing one or more analogs of an amino acid (including, for example, unnatural amino acids, etc.), as well as other modifications known in the art. Polypeptides can occur as single chains or associated chains.

Polypeptides of the invention may be attached or immobilised to a solid support.

Polypeptides of the invention may comprise a detectable label e.g. a radioactive label, a fluorescent label, or a biotin label. This is particularly useful in immunoassay techniques.

Polypeptides of the invention typically consist of an artificial amino acid sequence, namely a sequence which is not present in any naturally-occurring meningococci.

Affinity for factor H can be quantitatively assessed using surface plasmon resonance (e.g. as disclosed in Schneider et al. (2009) *Nature* 458:890-5) with immobilised human fH. Mutations which provide an affinity reduction (i.e. an increase in the dissociation constant, $K_D$) of at least 10-fold, and ideally at least 100-fold, is preferred (when measured under the same experimental conditions relative to the same polypeptide but without the mutation).

Nucleic Acids

A fourth aspect of the invention provides a plasmid or other nucleic acid comprising a nucleotide sequence encoding a mutant v1.13 fHbp polypeptide, a mutant v1.15 fHbp polypeptide, or a fusion polypeptide as defined above.

Nucleic acids of the invention may be prepared in many ways e.g. by chemical synthesis (e.g. phosphoramidite synthesis of DNA) in whole or in part, by digesting longer nucleic acids using nucleases (e.g. restriction enzymes), by joining shorter nucleic acids or nucleotides (e.g. using ligases or polymerases), from genomic or cDNA libraries, etc.

Nucleic acids of the invention can take various forms e.g. single-stranded, double-stranded, vectors, primers, probes, labelled, unlabelled, etc.

Nucleic acids of the invention are preferably in isolated or substantially isolated form.

The term "nucleic acid" includes DNA and RNA, and also their analogues, such as those containing modified backbones, and also peptide nucleic acids (PNA), etc.

Nucleic acid according to the invention may be labelled e.g. with a radioactive or fluorescent label.

The invention also provides vectors (such as plasmids) comprising nucleotide sequences of the invention (e.g. cloning or expression vectors, such as those suitable for nucleic acid immunisation) and host cells transformed with such vectors.

Host Cells

A fifth aspect of the invention provides a host cell transformed with a plasmid comprising nucleotide sequences of the invention as defined above.

The host cell of the invention is preferably a bacterium which expresses a polypeptide of the invention. The bacterium may be, for example, a meningococcus or an *E. coli*. The bacterium may constitutively express the polypeptide, but in some embodiments expression may be under the control of an inducible promoter. The bacterium may hyper-express the polypeptide (cf. WO2006/081259). Expression of the polypeptide is ideally not phase variable.

The cell may be a meningococcal bacterium, such as a meningococcal bacterium having down-regulation or knockout of mltA and also optionally having down-regulation or knockout of: (i) at least one gene involved in rendering the lipid A portion of LPS toxic, particularly of IpxI1; and/or (ii) at least one gene involved in the capsular polysaccharide synthesis or export, particularly of synX and/or ctrA.

Vesicles

A sixth aspect of the invention provides outer membrane vesicles prepared from a host cell of the invention, particularly from a meningococcus host cell.

Vesicles prepared from a host cell of the invention preferably include a polypeptide according to the invention, which should be in an immune-accessible form in the vesicles i.e. an antibody which can bind to purified polypeptide of the invention should also be able to bind to the polypeptide which is present in the vesicles.

These membrane vesicles include any proteoliposomic vesicle obtained by disruption of or blebbing from a meningococcal outer membrane to form vesicles therefrom that include protein components of the outer membrane. Thus, the term includes outer membrane vesicles (OMVs; sometimes referred to as 'blebs'), microvesicles (MVs [WO02/09643]) and 'native OMVs' ('NOMVs' [Katial et al. (2002) *Infect Immun* 70:702-707]).

MVs and NOMVs are naturally-occurring membrane vesicles that form spontaneously during bacterial growth and are released into culture medium. MVs can be obtained by culturing *Neisseria* in broth culture medium, separating whole cells from the smaller MVs in the broth culture medium (e.g. by filtration or by low-speed centrifugation to pellet only the cells and not the smaller vesicles), and then collecting the MVs from the cell-depleted medium (e.g. by filtration, by differential precipitation or aggregation of MVs, by high-speed centrifugation to pellet the MVs). Strains for use in production of MVs can generally be selected on the basis of the amount of MVs produced in culture e.g. U.S. Pat. No. 6,180,111 and WO01/34642 describe *Neisseria* with high MV production.

OMVs are prepared artificially from bacteria, and may be prepared using detergent treatment (e.g. with deoxycholate), or by non-detergent means (e.g. see WO2004/019977). Techniques for forming OMVs include treating bacteria with a bile acid salt detergent (e.g. salts of lithocholic acid, chenodeoxycholic acid, ursodeoxycholic acid, deoxycholic acid, cholic acid, ursocholic acid, etc., with sodium deoxycholate [see EP0011243 and Fredriksen et al. (1991) *NIPH Ann.* 14(2):67-80] being preferred for treating *Neisseria*) at a pH sufficiently high not to precipitate the detergent [WO01/91788]. Other techniques may be performed substantially in the absence of detergent [WO2004/019977] using techniques such as sonication, homogenisation, microfluidisation, cavitation, osmotic shock, grinding, French press, blending, etc. Methods using no or low detergent can retain useful antigens such as NspA and fHbp. Thus, a method may use an OMV extraction buffer with about 0.5% deoxycholate or lower e.g. about 0.2%, about 0.1%, <0.05% or zero.

A useful process for OMV preparation is described in WO2005/004908 and involves ultrafiltration on crude OMVs, rather than instead of high speed centrifugation. The process may involve a step of ultracentrifugation after the ultrafiltration takes place. OMVs can also be purified using the two-stage size filtration process described in WO2011/036562.

Vesicles for use with the invention can be prepared from any meningococcal strain. The vesicles will usually be from a serogroup B strain, but it is possible to prepare them from serogroups other than B (e.g. WO01/91788 discloses a process for serogroup A), such as A, C, W135 or Y. The strain may be of any serotype (e.g. 1, 2a, 2b, 4, 14, 15, 16, etc.), any serosubtype, and any immunotype (e.g. L1; L2; L3; L3,3,7; L10; etc.). The meningococci may be from any suitable lineage, including hyperinvasive and hypervirulent lineages e.g. any of the following seven hypervirulent lineages: subgroup I; subgroup III; subgroup IV-1; ET-5 complex; ET-37 complex; A4 cluster; lineage 3.

Bacteria of the invention may, in addition to encoding a polypeptide of the invention, have one or more further modifications. For instance, they may have a modified fur gene [WO98/56901]. Expression of nspA expression may be up-regulated with concomitant porA and cps knockout. Further knockout mutants of *N. meningitidis* for OMV production are disclosed e.g. in WO2004/014417. Claassen et al. (1996) 14(10):1001-8 discloses the construction of vesicles from strains modified to express six different PorA subtypes. Mutant *Neisseria* with low endotoxin levels, achieved by knockout of enzymes involved in LPS biosynthesis, may also be used. Mutant *Neisseria* engineered to reduce or switch off expression of at least one gene involved in rendering toxic the lipid A portion of LPS, in particular of Ipxl1 gene, can be used with the invention [Fisseha et al. (2005) *Infect Immun* 73:4070-80]. Similarly, mutant *Neisseria* engineered to reduce or switch off expression of at least one gene involved in the capsular polysaccharide synthesis or export, in particular of synX and/or ctrA genes can be used with the invention. These or other mutants can all be used with the invention.

Thus, a strain used with the invention may in some embodiments express more than one PorA subtype. 6-valent and 9-valent PorA strains have previously been constructed. The strain may express 2, 3, 4, 5, 6, 7, 8 or 9 of PorA subtypes: P1.7,16; P1.5-1,2-2; P1.19,15-1; P1.5-2,10; P1.12-1,13; P1.7-2,4; P1.22,14; P1.7-1,1 and/or P1.18-1,3,6. In other embodiments a strain may have been down-regulated for PorA expression e.g. in which the amount of PorA has been reduced by at least 20% (e.g. ≥30%, ≥40%, ≥50%, ≥60%, ≥70%, ≥80%, ≥90%, ≥95%, etc.), or even knocked out, relative to wild-type levels (e.g. relative to strain H44/76).

In some embodiments a strain may hyper-express (relative to the corresponding wild-type strain) certain proteins. For instance, strains may hyper-express NspA, protein 287 [WO01/52885], fHbp [WO2006/081259] (including fHbp of the invention), TbpA and/or TbpB [WO00/25811], Cu,Zn-superoxide dismutase, HmbR, etc.

A gene encoding a polypeptide of the invention may be integrated into the bacterial chromosome or may be present in episomal form e.g. within a plasmid.

Advantageously for vesicle production, a meningococcus may be genetically engineered to ensure that expression of the polypeptide is not subject to phase variation. Methods for reducing or eliminating phase variability of gene expression in meningococcus are disclosed in WO2004/015099. For example, a gene may be placed under the control of a constitutive or inducible promoter, or by removing or replacing the DNA motif which is responsible for its phase variability.

In some embodiments a strain may include one or more of the knockout and/or hyper-expression mutations disclosed in references WO02/09746, WO01/09350, WO02/062378, and WO2004/014417. For instance, following the guidance and nomenclature in these four documents, useful genes for down-regulation and/or knockout include: (a) Cps, CtrA, CtrB, CtrC, CtrD, FrpB, GalE, HtrB/MsbB, LbpA, LbpB, LpxK, Opa, Opc, PilC, PorB, SiaA, SiaB, SiaC, SiaD, TbpA, and/or TbpB; (b) CtrA, CtrB, CtrC, CtrD, FrpB, GalE, HtrB/MsbB, LbpA, LbpB, LpxK, Opa, Opc, PhoP, PilC, PmrE, PmrF, SiaA, SiaB, SiaC, SiaD, TbpA, and/or TbpB; (c) ExbB, ExbD, rmpM, CtrA, CtrB, CtrD, GalE, LbpA, LpbB, Opa, Opc, PilC, PorB, SiaA, SiaB, SiaC, SiaD, TbpA, and/or TbpB; or (d) CtrA, CtrB, CtrD, FrpB, OpA, OpC, PilC, PorB, SiaD, SynA, SynB, SynX and/or SynC.

Where a mutant strain is used, in some embodiments it may have one or more, or all, of the following characteristics: (i) down-regulated or knocked-out LgtB and/or GalE to truncate the meningococcal LOS; (ii) up-regulated TbpA; (iii) up-regulated NhhA; (iv) up-regulated Omp85; (v) up-regulated LbpA; (vi) up-regulated NspA; (vii) knocked-out PorA; (viii) down-regulated or knocked-out FrpB; (ix) down-regulated or knocked-out Opa; (x) down-regulated or knocked-out Opc; (xii) deleted cps gene complex. A truncated LOS can be one that does not include a sialyl-lacto-N-neotetraose epitope e.g. it might be a galactose-deficient LOS. The LOS may have no α chain.

Depending on the meningococcal strain used for preparing the vesicles, they may or may not include the strain's native fHbp antigen (WO2004/046177).

In one preferred embodiment, a meningococcus does not express a functional MltA protein. As discussed in WO2006/046143 and Adu-Bobie et al. (2004) *Infect Immun* 72:1914-19, knockout of MltA (the membrane-bound lytic transglycosylase, also known as GNA33) in meningococcus provides bacteria which spontaneously release large amounts of membrane vesicles into culture medium, from which they can be readily purified. For instance, the vesicles can be purified using the two-stage size filtration process of WO2011/036562 comprising: (i) a first filtration step in which vesicles are separated from the bacteria based on their different sizes, with the vesicles passing into the filtrate; and (ii) a second filtration step in which the vesicles are retained in the retentate. The MltA mutation (down-regulation or knockout) has been used in 'GMMA' vaccines [Koeberling et al. (2014) *Vaccine* 32:2688-95], and can conveniently be combined with further down regulation or knockout of in particular of at least one gene involved in rendering toxic the lipid A portion of LPS, particularly of Ipxl1 and/or of at least one gene involved in the capsular polysaccharide synthesis or export, particularly of synX and/or ctrA genes. GMMA (Generalized Modules for Membrane Antigens) are genetically detoxified OMV that are produced from meningococcal strains that have been engineered to release GMMA with reduced reactogenicity and increased immunogenicity. GMMA induce less proinflammatory cytokines than OMV when tested in the monocyte activation test (MAT).

A preferred meningococcal strain for a 'GMMA' vaccine using this approach expresses a mutant v2 fHbp and/or a mutant v3 fHbp of the invention, and expression can be driven by strong promoters. Vesicles released by this strain include the mutant v2 and/or v3 fHbp proteins in immunogenic form, and administration of the vesicles can provide bactericidal antibody response as discussed in Koeberling et al. (2014) *Vaccine* 32:2688-95. The strain can also express a v1 fHbp, or a v1 fHbp can instead be provided as a separate recombinant protein in soluble form (and the v1 fHbp can be a wild-type or a mutant sequence e.g. mutated to disrupt its ability to bind to fH, as discussed above). The invention provides such strains, and also provides the vesicles which these strains release e.g. as purified from culture media after growth of the strains. A preferred v2 mutant for expression in these strains has a mutation at S32 and/or L123 as discussed herein, and a preferred v3 mutant for expression in these strains has a mutation at S32 and/or L126 as discussed herein. Thus, vesicles prepared from meningococci expressing these v2 and v3 mutant fHbp sequences are particularly preferred immunogens for use in vaccines of the invention.

Useful promoters for use in such strains include those disclosed in WO2013/033398 and WO2013/113917. For instance, the promoter can be: (a) the promoter from a porin gene, preferably porA or porB, particularly from *N. meningitidis*; or (b) a rRNA gene promoter (such as a 16S rRNA gene), particularly from *N. meningitidis*. Where a meningococcal porin promoter is used, it is preferably from porA, and even more particularly a −10 region from a meningococcal porA gene promoter, and/or a −35 region from a meningococcal porA gene promoter (preferably wherein the −10 region and the −35 region are separated by an intervening sequence of 12-20 nucleotides, and wherein the intervening sequence either contains no poly-G sequence or includes a poly-G sequence having no more than eight consecutive G nucleotides). Where a rRNA gene promoter is used, it can comprise more particularly (i) a −10 region from a meningococcal rRNA gene promoter and/or (ii) a −35 region from a meningococcal rRNA gene promoter. It is also possible to use a hybrid of (a) and (b), for instance to have a −10 region from a porA promoter and a −35 region from a rRNA promoter (which can be a consensus −35 region). A useful promoter can thus be a promoter which includes either (i) a −10 region from a (particularly meningococcal) rRNA gene and a −35 region from a (particularly meningococcal) porA gene, or (ii) a −10 region from a (particularly meningococcal) porA gene and a −35 region from a (particularly meningococcal) rRNA gene.

If LOS is present in a vesicle it is possible to treat the vesicle so as to link its LOS and protein components ("intra-bleb" conjugation [WO2004/014417]).

Immunogenic Compositions

Polypeptides of the invention may be used as active ingredient(s) in immunogenic compositions, and so a seventh aspect of the invention provides an immunogenic composition comprising a mutant v1.13 fHbp polypeptide according to the first aspect of the invention, a mutant v1.15 fHbp polypeptide according to the second aspect of the invention, a fusion polypeptide according to the third aspect of the invention, or a vesicle according to the sixth aspect of the invention. Said immunogenic compositions are useful for immunizing a mammal, preferably a human, against *Neisseria meningitidis* infection.

In a preferred embodiment of the invention, in addition to polypeptide antigens of the first, second or third aspects of the invention, the immunogenic composition of the invention further comprises one or more of the antigenic components of 4CMenB.

As described above, the 4CMenB product (BEXSERO) contains a preparation of OMV from the epidemic strain of group B Meningococcal NZ98/254, B:4:P1.7b,4. The same OMVs are found in the MeNZB vaccine and are referred to herein as OMVnz. In addition, 4CMenB comprises five meningococcal antigens: NHBA (287; subvariant 1.2), fHbp (741; subvariant 1.1), NadA (961; subvariant 3.1), GNA1030 (953) and GNA2091 (936). Four of these antigens are present as fusion proteins (an NHBA-GNA1030 fusion protein (287-953) and a GNA2091-fHbp (936-741) fusion protein).

A 0.5 ml dose of the complete 4CMenB product is formulated to contain 50 μg of each of NHBA-GNA1030, NadA and GNA2091-fHbp, adsorbed onto 1.5 mg aluminium hydroxide adjuvant, and with 25 μg OMVs from *N. meningitidis* strain NZ98/254. In addition, each 0.5 ml dose of the formulation incudes 3.125 mg sodium chloride, 0.776 mg histidine and 10 mg sucrose.

In a further preferred embodiment, the immunogenic composition of the invention comprises the complete vaccine product 4CMenB, marketed under the trade name BEXSERO.

In a further preferred embodiment, the immunogenic composition of the invention comprises the fHbp fusion polypeptide of SEQ ID NO. 19 (fHbp 23S_1.13_E211A/S216R) and the complete 4CMenB composition.

Meningococcus Serogroups A. C. W135 and Y

Compositions of the present invention may also include capsular saccharide antigens from one or more of meningococcus serogroups Y, W135, C and A, wherein the antigens are conjugated to carrier protein(s) and/or are oligosaccharides. Capsular saccharides may be used in the form of oligosaccharides. These are conveniently formed by fragmentation of purified capsular polysaccharide (e.g. by hydrolysis), which will usually be followed by purification of the fragments of the desired size.

Current serogroup C vaccines (MENJUGATE [Costantino et al. (1992) *Vaccine* 10:691-698, Jones (2001) *Curr Opin Investig Drugs* 2:47-49], MENINGITEC and NEISVAC-C) include conjugated saccharides. MENJUGATE and MENINGITEC have oligosaccharide antigens conjugated to a $CRM_{197}$ carrier, whereas NEISVAC-C uses the complete polysaccharide (de-O-acetylated) conjugated to a tetanus toxoid carrier.

The vaccine products marketed under the trade names MENVEO, MENACTRA, and NIMENRIX all contain conjugated capsular saccharide antigens from each of serogroups Y, W135, C and A.

In MENVEO (also known generically as Meningococcal (Groups A, C, Y, and W-135) Oligosaccharide Diphtheria CRM197 Conjugate Vaccine) each of the A, C, W135 and Y antigens is conjugated to a $CRM_{197}$ carrier.

In MENACTRA (also known generically as Meningococcal (Groups A, C, Y and W-135) Polysaccharide Diphtheria Toxoid Conjugate Vaccine) each of the A, C, W135 and Y antigens is conjugated to a diptheria toxoid carrier.

In NIMENRIX (also known generically as Meningococcal polysaccharide groups A, C, W-135 and Y conjugate vaccine) each of the A, C, W135 and Y antigens is conjugated to a tetanus toxoid carrier.

In a preferred embodiment of the invention, in addition to polypeptide antigens of the first, second or third aspects of the invention, the immunogenic composition of the invention further comprises one or more conjugated capsular saccharide antigens from *N. meningitidis* serogroup A, C, W135 and/or Y.

In a preferred embodiment of the invention, in addition to polypeptide antigens of the first, second or third aspects of the invention, the immunogenic composition of the invention further comprises the complete 4CMenB product, together with one or more conjugated capsular saccharide antigens from *N. meningitidis* serogroup A, C, W135 and/or Y.

In a preferred embodiment the immunogenic composition of the invention comprises, in addition to polypeptide antigens of the first, second or third aspects of the invention, the complete 4CMenB product, together with conjugated capsular saccharide antigens from each of *N. meningitidis* serogroups A, C, W135 and/or Y, forming a pentavalent immunogenic composition comprising antigens against each of the meningococcal serotypes A, B, C, W135 and Y.

In preferred embodiments, the composition includes the A, C, W135 and Y antigen conjugates which are present in MENVEO, the A, C, W135 and Y antigen conjugates which are present in MENACTRA, or the A, C, W135 and Y antigen conjugates which are present in NIMENRIX.

In a further preferred embodiment, the immunogenic composition of the invention comprises the fHbp fusion polypeptide of SEQ ID NO. 19 (fHbp 23S_1.13_E211A/S216R), the complete 4CMenB product and the A, C, W135 and Y antigen conjugates which are present in MENVEO.

Alternatively, an immunogenic composition of the invention comprising polypeptide antigens of the first, second or third aspects of the invention may be co-administered with one or more of BEXSERO and MENVEO, MENACTRA or NIMENRIX. Preferably an immunogenic composition of the invention is co-administered with BEXSERO and MENVEO.

As used herein "co-administered" means that the different immunogenic compositions/vaccines can be administered either separately or as a combination.

Where the vaccines are administered separately, they will typically be administered at different sites e.g. one vaccine to the left upper arm, and a second vaccine to the right upper arm. Thus, two vaccines may be administered contralaterally (e.g. both arms or both legs, or a contralateral arm and leg) or ipsilaterally (e.g. the arm and leg on the same side of the body). Although the vaccines are administered separately, they are administered at substantially the same time (e.g. during the same medical consultation or visit to a healthcare professional or vaccination centre), such as within 1 hour of each other.

Rather than co-immunising separately, however, administration as a combination may be performed. Thus, co-immunisation may use a combination vaccine i.e. a single composition in which the different immunogens are admixed. Combination vaccines offer subjects the advantage of receiving a reduced number of injections, which can lead to the clinical advantage of increased compliance.

Use of Immunogenic Compositions of the Invention

Immunogenic compositions of the invention are suitable for use in medicine, and in particular can be used to immunize a mammal against infection and/or disease caused by *Neisseria meningitidis*, such that recipients of the immunogenic composition mount an immune response which provides protection against infection by and/or disease due to *Neisseria meningitidis* bacteria.

In a preferred embodiment, immunogenic compositions of the invention are useful for immunizing a mammal against meningococcal B infection or disease. However, in embodiments of the invention wherein meningococcal serogroup B antigens are combined with other meningococcal serogroup antigens (e.g. A, C, W and/or Y antigens), the immunogenic compositions are useful for immunizing a mammal against meningococcal A, B, C, W and/or Y infection or disease.

Therefore, immunogenic compositions according to the invention are used in prophylactic methods for immunizing subjects against infection and/or disease caused by *Neisseria meningitidis*. The immunogenic compositions may also be used in therapeutic methods (i.e. to treat *Neisseria meningitidis* infection).

The invention also provides a method for raising an immune response in vivo against *Neisseria meningitidis* infection in a mammal, comprising administering an immunogenic composition of the invention to the mammal. The invention also provides polypeptides of the invention for use in such methods.

The immune response is preferably protective and preferably involves antibodies and/or cell-mediated immunity. Preferably, the immune response is a bactericidal antibody response. The method may raise a booster response. By raising an in vivo immune response, the mammal can be protected against Neisserial disease (in particular meningococcal infection) The invention also provides a method for protecting a mammal against a Neisserial (e.g. meningococcal) infection, comprising administering to the mammal an immunogenic composition of the invention.

The invention provides polypeptides of the invention for use as medicaments (e.g. as immunogenic compositions or as vaccines) or as diagnostic reagents. It also provides the use of nucleic acids or polypeptides of the invention in the manufacture of a medicament for preventing Neisserial (e.g. meningococcal) infection in a mammal.

The immunological compositions of the invention are preferably formulated as vaccine products, which are suitable for therapeutic (i.e. to treat an infection) or prophylactic (i.e. to prevent an infection) use. Vaccines are typically prophylactic.

The mammal is preferably a human. The human may be an adult, an adolescent or a child (e.g. a toddler or infant). A vaccine intended for children may also be administered to adults e.g. to assess safety, dosage, immunogenicity, etc.

The uses and methods are particularly useful for preventing/treating diseases including, but not limited to, meningitis (particularly bacterial, such as meningococcal, meningitis) and bacteremia. For instance, they are suitable for active immunisation of individuals against invasive meningococcal disease caused by *N. meningitidis* (for example in serogroup B).

Protection against *N. meningitidis* can be measured epidemiologically e.g. in a clinical trial, but it is convenient to use an indirect measure to confirm that an immunogenic composition elicits a serum bactericidal antibody (SBA) response in recipients. In the SBA assay, sera from recipients of the composition are incubated with target bacteria (in the present invention, *N. meningitidis*) in the presence of complement (preferably human complement, although baby rabbit complement is often used instead) and killing of the bacteria is assessed at various dilutions of the sera to determine SBA activity. Results observed in the SBA assay can be reinforced by carrying out a competitive SBA assay to provide further indirect evidence of the immunogenic activity of antigen(s) of interest. In the competitive SBA assay, sera from recipients of the immunogenic composition containing the antigen(s) are pre-incubated with said antigen(s), and subsequently incubated with target bacteria in the presence of human complement. Killing of the bacteria is then assessed, and will be reduced or abolished if bactericidal antibodies in the recipients' sera bind to the antigens of interested during the pre-incubation phase and are therefore not available to bind to surface antigen on the bacteria.

It is not necessary that the composition should protect against each and every strain of *N. meningitidis*, or that each and every recipient of the composition must be protected. Such universal protection is not the normal standard in this field. Rather, protection is normally assessed against a panel of reference laboratory strains, often selected on a country-by-country basis and perhaps varying with time, and is measured across a population of recipients.

Preferred compositions of the invention can confer an antibody titre in a patient that is superior to the criterion for seroprotection for each antigenic component for an acceptable percentage of human subjects. Antigens with an associated antibody titre above which a host is considered to be seroconverted against the antigen are well known, and such titres are published by organisations such as WHO. Preferably more than 80% of a statistically significant sample of subjects is seroconverted, more preferably more than 90%, still more preferably more than 93% and most preferably 96-100%.

Immunogenic compositions comprise an immunologically effective amount of immunogen, as well as any other of other specified components, as needed.

By 'immunologically effective amount', it is meant that the administration of that amount to an individual, either in a single dose or as part of a series, is effective for treatment or prevention.

The term "prevention" means that the progression of the disease is reduced and/or eliminated, or that the onset of the disease is eliminated. For example, the immune system of a subject may be primed (e.g. by vaccination) to trigger an immune response and repel infection such that the onset of the disease is eliminated. A vaccinated subject may thus get infected, but is better able to repel the infection than a control subject. This amount varies depending upon the health and physical condition of the individual to be treated, age, the taxonomic group of the individual to be treated (e.g. non-human primate, primate, etc.), the capacity of the individual's immune system to synthesise antibodies, the degree of protection desired, the formulation of the vaccine, the treating doctor's assessment of the medical situation, and other relevant factors. It is expected that the amount will fall in a relatively broad range that can be determined through routine trials. The composition may be administered in conjunction with other immunoregulatory agents.

Vaccine Efficacy

Immunogenic compositions for use in the present invention preferably have a vaccine efficacy against at least one strain of *N. meningitidis* of at least 10% e.g. ≥20%, ≥30%, ≥40%, ≥50%, ≥60%, ≥70%, ≥80%, ≥85%, ≥90%, or more.

Vaccine efficacy is determined by the reduction in relative risk of developing meningococcal disease in subjects who receive a composition according to the invention compared to subjects who do not receive such a composition (e.g. are non-immunized or who receive a placebo or negative control). Thus, the incidence of meningococcal disease in a population which has been immunized according to the invention is compared to the incidence in a control population who has not been immunized according to the invention to give relative risk and vaccine efficacy is 100% minus this figure.

Vaccine efficacy is determined for a population rather than for an individual. Thus, it is a useful epidemiologic tool but does not predict individual protection. For instance, an individual subject might be exposed to a very large inoculum of the infecting agent, or might have other risk factors which make them more subject to infection, but this does not negate the validity or utility of the efficacy measure. The size of a population which is immunized according to the invention, and for which vaccine efficacy is measured, is ideally at least 100 and may be higher e.g. at least 500 subjects. The size of the control group should also be at least 100 e.g. at least 500.

Administration

Compositions of the invention will generally be administered directly to a patient. Direct delivery may be accomplished by parenteral injection (e.g. subcutaneously, intraperitoneally, intravenously, intramuscularly, or to the interstitial space of a tissue), or by rectal, oral, vaginal, topical, transdermal, intranasal, ocular, aural, pulmonary or other mucosal administration. Intramuscular administration to the thigh or the upper arm is preferred. Injection may be via a needle (e.g. a hypodermic needle), but needle-free injection may alternatively be used. A typical intramuscular dose is about 0.5 ml.

Neisserial infections affect various areas of the body and so the compositions of the invention may be prepared in various forms. For example, the compositions may be prepared as injectables, either as liquid solutions or suspensions. Solid forms suitable for solution in, or suspension in, liquid vehicles prior to injection can also be prepared. The composition may be prepared for topical administration e.g. as an ointment, cream or powder. The composition be prepared for oral administration e.g. as a tablet or capsule, or as a syrup (optionally flavoured). The composition may be prepared for pulmonary administration e.g. as an inhaler, using a fine powder or a spray. The composition may be prepared as a suppository or pessary. The composition may be prepared for nasal, aural or ocular administration e.g. as drops. Compositions suitable for parenteral injection are most preferred.

The invention may be used to elicit systemic and/or mucosal immunity.

As used herein, a 'dose' of the composition is a volume of the composition suitable for administration to a subject as a single immunisation. Human vaccines are typically administered in a dosage volume of about 0.5 ml, although fractional doses may be administered (e.g., to children). The volume of the dose may further vary depending on the concentration of the antigens in the composition.

The composition may further be provided in a 'multidose' kit, i.e., a single container containing sufficient composition for multiple immunisations. Multidoses may include a preservative, or the multidose container may have an aseptic adaptor for removal of individual doses of the composition.

Administration can involve a single dose schedule, but will usually involve a multiple dose schedule. Preferably, a schedule of at least three doses is given. Suitable intervals between priming doses can be routinely determined e.g. between 4-16 weeks, such as one month or two months. For example, BEXSERO can be administered at ages of 2, 4 & 6 months, or at 2, 3 & 4 months, with a fourth optional dose at 12 months.

The subject who is immunized is a human being, who may be any age e.g. 0-12 months old, 1-5 years old, 5-18 years old, 18-55 years old, or more than 55 years old. Preferably, the subject who is immunized is an adolescent (e.g. 12-18 years old) or an adult (18 years or older).

Optionally, the subject is an adolescent or adult who has been immunized against *N. meningitidis* in childhood (e.g. before 12 years of age), and who receives a booster dose of an immunogenic composition according to the invention.

Where the invention refers to co-immunization, the different immunogenic compositions/vaccines can be administered either separately or as a combination.

Where the vaccines are administered separately, they will typically be administered at different sites e.g. one vaccine to the left upper arm, and a second vaccine to the right upper arm. Thus, two vaccines may be administered contralaterally (e.g. both arms or both legs, or a contralateral arm and leg) or ipsilaterally (e.g. the arm and leg on the same side of the body). Although the vaccines are administered separately, they are administered at substantially the same time (e.g. during the same medical consultation or visit to a healthcare professional or vaccination centre), such as within 1 hour of each other.

Rather than co-immunising separately, however, administration as a combination may be performed. Thus, co-immunisation may use a combination vaccine i.e. a single composition in which the different immunogens are admixed. Combination vaccines offer subjects the advantage of receiving a reduced number of injections, which can lead to the clinical advantage of increased compliance.

Non-Antigenic Components

The immunogenic composition of the invention will generally include a pharmaceutically acceptable carrier, which can be any substance that does not itself induce the production of antibodies harmful to the patient receiving the composition, and which can be administered without undue toxicity. Pharmaceutically acceptable carriers can include liquids such as water, saline, glycerol and ethanol. Auxiliary substances, such as wetting or emulsifying agents, pH buffering substances, and the like, can also be present in such vehicles. A thorough discussion of suitable carriers is available in Gennaro (2000) *Remington: The Science and Practice of Pharmacy*. 20th edition, ISBN: 0683306472.

The composition is preferably sterile. It is preferably pyrogen-free. It is preferably buffered e.g. at between pH 6 and pH 8, generally around pH 7. Where a composition comprises an aluminium hydroxide salt, it is preferred to use a histidine buffer [WO03/009869]. Compositions of the invention may be isotonic with respect to humans.

Adjuvants which may be used in compositions of the invention include, but are not limited to insoluble metal salts, oil-in-water emulsions (e.g. MF59 or AS03, both containing squalene), saponins, non-toxic derivatives of LPS (such as monophosphoryl lipid A or 3-O-deacylated MPL), immunostimulatory oligonucleotides, detoxified bacterial ADP-ribosylating toxins, microparticles, liposomes, imidazoquinolones, or mixtures thereof. Other substances that act as immunostimulating agents are disclosed in chapter 7 of *Vaccine Design* . . . (1995) eds. Powell & Newman. ISBN: 030644867X. Plenum.

The use of an aluminium hydroxide and/or aluminium phosphate adjuvant is particularly preferred, and polypeptides are generally adsorbed to these salts. These salts include oxyhydroxides and hydroxyphosphates (e.g. see chapters 8 & 9 of *Vaccine Design* . . . (1995) eds. Powell & Newman. ISBN: 030644867X. Plenum). The salts can take any suitable form (e.g. gel, crystalline, amorphous, etc.).

Further Antigenic Components

Immunogenic compositions of the invention may include antigens for immunising against other diseases or infections. For example, the composition may include one or more of the following further antigens:

- a saccharide antigen from *Streptococcus pneumoniae* [e.g. Watson (2000) *Pediatr Infect Dis J* 19:331-332, Rubin (2000) *Pediatr Clin North Am* 47:269-285, and Jedrzejas (2001) *Microbiol Mol Biol Rev* 65:187-207].
- an antigen from hepatitis A virus, such as inactivated virus [e.g. Bell (2000) *Pediatr Infect Dis J* 19:1187-1188, Iwarson (1995) *APMIS* 103:321-326].
- an antigen from hepatitis B virus, such as the surface and/or core antigens [e.g. Gerlich et al. (1990) *Vaccine* 8 Suppl: S63-68 & 79-80].
- a diphtheria antigen, such as a diphtheria toxoid [e.g. chapter 3 of *Vaccines* (1988) eds. Plotkin & Mortimer. ISBN 0-7216-1946-0] e.g. the $CRM_{197}$ mutant [e.g. Del Guidice et al. (1998) *Molecular Aspects of Medicine* 19:1-70].
- a tetanus antigen, such as a tetanus toxoid (e.g. chapter 4 of *Vaccines* (1988) eds. Plotkin & Mortimer. ISBN 0-7216-1946-0).
- an antigen from *Bordetella pertussis*, such as pertussis holotoxin (PT) and filamentous haemagglutinin (FHA) from *B. pertussis*, optionally also in combination with pertactin and/or agglutinogens 2 and 3 (e.g. Gustafsson et al. (1996) *N. Engl. J. Med.* 334:349-355, and Rappuoli et al. (1991) *TIBTECH* 9:232-238).
- a saccharide antigen from *Haemophilus influenzae* B [e.g. Costantino et al. (1999) *Vaccine* 17:1251-1263].
- polio antigen(s) [e.g. Sutter et al. (2000) *Pediatr Clin North Am* 47:287-308, and Zimmerman & Spann (1999) *Am Fam Physician* 59:113-118, 125-126], such as IPV.
- measles, mumps and/or rubella antigens (e.g. chapters 9, 10 & 11 of *Vaccines* (1988) eds. Plotkin & Mortimer. ISBN 0-7216-1946-0).
- influenza antigen(s) (e.g. chapter 19 of *Vaccines* (1988) eds. Plotkin & Mortimer. ISBN 0-7216-1946-0), such as the haemagglutinin and/or neuraminidase surface proteins.
- an antigen from *Moraxella catarrhalis* [e.g. McMichael (2000) *Vaccine* 19 Suppl 1: S101-107].
- an protein antigen from *Streptococcus agalactiae* (group B *streptococcus*) [e.g. Schuchat (1999) *Lancet* 353 (9146):51-6, WO02/34771].
- a saccharide antigen from *Streptococcus agalactiae* (group B *streptococcus*).
- an antigen from *Streptococcus pyogenes* (group A streptococcus) [e.g. WO02/34771, Dale (1999) *Infect Dis Clin North Am* 13:227-43, Ferretti et al. (2001) *PNAS USA* 98: 4658-4663].
- an antigen from *Staphylococcus aureus* [e.g. Kuroda et al. (2001) *Lancet* 357(9264):1225-1240; see also pages 1218-1219].

Toxic protein antigens may be detoxified where necessary (e.g. detoxification of pertussis toxin by chemical and/or genetic means [Rappuoli et al. (1991) *TIBTECH* 9:232-238]).

Where a diphtheria antigen is included in the composition it is preferred also to include tetanus antigen and pertussis antigens. Similarly, where a tetanus antigen is included it is preferred also to include diphtheria and pertussis antigens. Similarly, where a pertussis antigen is included it is preferred also to include diphtheria and tetanus antigens. DTP combinations are thus preferred.

Saccharide antigens are preferably in the form of conjugates. In general, conjugation enhances the immunogenicity of saccharides as it converts them from T-independent antigens to T-dependent antigens, thus allowing priming for immunological memory. Conjugation is particularly useful for paediatric vaccines and is a well-known technique.

Typical carrier proteins are bacterial toxins, such as diphtheria or tetanus toxins, or toxoids or mutants thereof. The $CRM_{197}$ diphtheria toxin mutant [Research Disclosure, 453077 (January 2002)] is useful, and is the carrier in the *Streptococcus pneumoniae* vaccine sold under the trade name PREVNAR. Other suitable carrier proteins include the *N. meningitidis* outer membrane protein complex [EP-A-0372501], synthetic peptides [EP-A-0378881, EP-A-0427347], heat shock proteins [WO93/17712, WO94/03208], pertussis proteins [WO98/58668, EP-A-0471177], cytokines [WO91/01146], lymphokines [WO91/01146], hormones [WO91/01146], growth factors [WO91/01146], artificial proteins comprising multiple human $CD4^+$ T cell epitopes from various pathogen-derived antigens [Falugi et al. (2001) *Eur J Immunol* 31:3816-3824] such as N19 [Baraldo et al. (2004) *Infect Immun* 72(8):4884-7], protein D from *H. influenzae* [EP-A-0594610, Ruan et al. (1990) *J Immunol* 145:3379-3384] pneumolysin [Kuo et al. (1995) *Infect Immun* 63:2706-13] or its non-toxic derivatives [Michon et al. (1998) *Vaccine*. 16:1732-41], pneumococcal surface protein PspA [WO02/091998], iron-uptake proteins [WO01/72337], toxin A or B from *C. difficile* [WO00/61761], recombinant *P. aeruginosa* exoprotein A (rEPA) [WO00/33882], etc.

Any suitable conjugation reaction can be used, with any suitable linker where necessary.

The saccharide will typically be activated or functionalised prior to conjugation. Activation may involve, for example, cyanylating reagents such as CDAP (e.g. 1-cyano-4-dimethylamino pyridinium tetrafluoroborate [Lees et al. (1996) *Vaccine* 14:190-198, WO95/08348]). Other suitable techniques use carbodiimides, hydrazides, active esters, norborane, p-nitrobenzoic acid, N-hydroxysuccinimide, S-NHS, EDC, TSTU, etc.

Linkages via a linker group may be made using any known procedure, for example, the procedures described in U.S. Pat. Nos. 4,882,317 and 4,695,624. One type of linkage involves reductive amination of the polysaccharide, coupling the resulting amino group with one end of an adipic acid linker group, and then coupling a protein to the other end of the adipic acid linker group [Porro et al. (1985) *Mol Immunol* 22:907-919, EP0208375]. Other linkers include B-propionamido [WO00/10599], nitrophenyl-ethylamine [Gever et al. Med. Microbiol. Immunol, 165:171-288 (1979)], haloacyl halides [U.S. Pat. No. 4,057,685], glycosidic linkages [U.S. Pat. Nos. 4,673,574; 4,761,283; 4,808,700], 6-aminocaproic acid [U.S. Pat. No. 4,459,286], ADH [U.S. Pat. No. 4,965,338], $C_4$ to $C_{12}$ moieties [U.S. Pat. No. 4,663,160] etc. As an alternative to using a linker, direct linkage can be used. Direct linkages to the protein may comprise oxidation of the polysaccharide followed by reductive amination with the protein, as described in, for example, U.S. Pat. Nos. 4,761,283 and 4,356,170.

A process involving the introduction of amino groups into the saccharide (e.g. by replacing terminal =O groups with —$NH_2$) followed by derivatisation with an adipic diester (e.g. adipic acid N-hydroxysuccinimido diester) and reaction with carrier protein is preferred. Another preferred reaction uses CDAP activation with a protein D carrier e.g. for MenA or MenC.

Antigens in the composition will typically be present at a concentration of at least 1 µg/ml each. In general, the concentration of any given antigen will be sufficient to elicit an immune response against that antigen.

Immunogenic compositions of the invention may be used therapeutically (i.e. to treat an existing infection) or prophylactically (i.e. to prevent future infection).

As an alternative to using protein antigens in the immunogenic compositions of the invention, nucleic acid (which could be RNA, such as a self-replicating RNA, or DNA, such as a plasmid) encoding the antigen may be used.

General

The term "comprising" encompasses "including" as well as "consisting" e.g. a composition "comprising" X may consist exclusively of X or may include something additional e.g. X+Y. References to "comprising" (or "comprises", etc.) may optionally be replaced by references to "consisting of" (or "consists of", etc.). The term "consisting essentially of" limits the scope of a claim to the specified materials or steps "and those that do not materially affect the basic and novel characteristic(s)" of the claimed invention.

The term "about" in relation to a numerical value x is optional and means, for example, x±10%.

The word "substantially" does not exclude "completely" e.g. a composition which is "substantially free" from Y may be completely free from Y. Where necessary, the word "substantially" may be omitted from the definition of the invention.

Where the disclosure concerns an "epitope", this epitope may be a B-cell epitope and/or a T-cell epitope, but will usually be a B-cell epitope. Such epitopes can be identified empirically (e.g. using PEPSCAN (e.g. see Geysen et al. (1984) *PNAS USA* 81:3998-4002 and Carter (1994) *Methods Mol Biol* 36:207-23) or similar methods), or they can be predicted (e.g. using the Jameson-Wolf antigenic index (Jameson, B A et al. 1988, *CABIOS* 4(1):181-186), matrix-based approaches (Raddrizzani & Hammer (2000) *Brief Bioinform* 1(2):179-89), MAPITOPE (Bublil et al. (2007) *Proteins* 68(1):294-304), TEPITOPE (De Lalla et al. (1999) *J. Immunol.* 163:1725-29 and Kwok et al. (2001) *Trends Immunol* 22:583-88), neural networks (Brusic et al. (1998) *Bioinformatics* 14(2):121-30), OptiMer & EpiMer (Meister et al. (1995) *Vaccine* 13(6):581-91 and Roberts et al. (1996) *AIDS Res Hum Retroviruses* 12(7):593-610), ADEPT (Maksyutov & Zagrebelnaya (1993) *Comput Appl Biosci* 9(3):291-7), Tsites (Feller & de la Cruz (1991) *Nature* 349(6311):720-1), hydrophilicity (Hopp (1993) *Peptide Research* 6:183-190), or antigenic index (Welling et al. (1985) *FEBS Lett.* 188:215-218)). Epitopes are the parts of an antigen that are recognized by and bind to the antigen binding sites of antibodies or T-cell receptors, and they may also be referred to as "antigenic determinants".

As used herein, references to "percentage sequence identity" between a query amino acid sequence and a subject amino acid sequence are understood to refer to the value of identity that is calculated using a suitable algorithm or software program known in the art to perform pairwise sequence alignment.

A query amino acid sequence may be described by an amino acid sequence identified in one or more claims herein. The query sequence may be 100% identical to the subject sequence, or it may include up to a certain integer number of amino acid alterations (e.g. point mutations, substitutions, deletions, insertions etc.) as compared to the subject sequence, such that the % identity is less than 100%. For example, the query sequence is at least 80, 85, 90, 95, 96, 97, 98, or 99% identical to the subject sequence.

Preferred alignment tools used to perform alignment and calculate percentage (%) sequence identity are local alignment tools, such as the Basic Local Alignment Search Tool (BLAST) algorithms. Software for performing BLAST analyses is publicly available through the National Centre for Biotechnology Information www(dot)ncbi(dot)nlm(dot)nih(dot)gov. Alignment may be determined by the Smith-Waterman homology search algorithm using an affine gap search with a gap open penalty of 12 and a gap extension penalty of 2, BLOSUM matrix of 62. The Smith-Waterman homology search algorithm is disclosed in Smith & Waterman (1981) *Adv. Appl. Math.* 2: 482-489. Other preferred alignment tools are Water (EMBOSS) and Marcher (EMBOSS). Alternatively, preferred alignment tools used to perform alignment and calculate percentage (%) sequence identity are best fit alignment tools, such as GENEPAST, also known as KERR algorithm.

In order to calculate percent identity, the query and subject sequences may be compared and aligned for maximum correspondence over a designated region (e.g. a region of at least about 40, 45, 50, 55, 60, 65 or more amino acids in length, and can be up to the full length of the subject amino acid sequence). Said designated region must include the region of the query sequence comprising any specified point mutations in the amino acid sequence. Alternatively, percentage sequence identity may be calculated over the "full length" of the subject sequence. Any N-terminal or C-terminal amino acid stretches that may be present in the query sequence, such as signal peptides or leader peptide or C-terminal or N-terminal tags, should excluded from the alignment.

The term "fragment" in reference to polypeptide sequences means that the polypeptide is a fraction of a full-length protein. As used herein, a fragment of a mutant polypeptide also comprises the mutation(s). Fragments may possess qualitative biological activity in common with the full-length protein, for example, an "immunogenic fragment" contains or encodes one or more epitopes, such as immunodominant epitopes, that allows the same or similar immune response to be raised to the fragment as is raised to the full-length sequence. Polypeptide fragments generally have an amino (N) terminus portion and/or carboxy (C) terminus portion deleted as compared to the native protein, but wherein the remaining amino acid sequence of the fragment is identical to the amino acid sequence of the native protein. Polypeptide fragments may contain, for example: about 8, 10, 12, 14, 16, 18, 20, 22, 24, 26, 28, 30, 32, 24, 26, 28, 40, 45, 50, 55, 60, 70, 80, 90, 100, 150, 200, 240, 241, 242, 243, 244, 245, 246, 247, 248, 249, 250, 251, 252, 253, 254, 255, 256, 257, 258, 259, 260, 261, 262 contiguous amino acids, including all integers in between, of a reference polypeptide sequence, for example between 50 and 260, 50 and 255, 50 and 250, 50 and 200, 50 and 150 contiguous amino acids of a reference polypeptide sequence. The term fragment explicitly excludes full length fHbp polypeptides and mature lipoproteins thereof.

After serogroup, meningococcal classification includes serotype, serosubtype and then immunotype, and the standard nomenclature lists serogroup, serotype, serosubtype, and immunotype, each separated by a colon e.g. B:4: P1.15: L3,7,9. Within serogroup B, some lineages cause disease often (hyperinvasive), some lineages cause more severe forms of disease than others (hypervirulent), and others rarely cause disease at all. Seven hypervirulent lineages are recognised, namely subgroups I, III and IV-1, ET-5 complex, ET-37 complex, A4 cluster and lineage 3. These have been defined by multilocus enzyme electrophoresis (MLEE), but multilocus sequence typing (MLST) has also been used to classify meningococci. The four main hypervirulent clusters are ST32, ST44, ST8 and ST11 complexes.

References herein to "enhanced stability" or "higher stability" or "increased stability" mean that the mutant polypeptides disclosed herein have a higher relative thermostability (in kcal/mol) as compared to a non-mutant (wild-type) polypeptide under the same experimental conditions. The stability enhancement can be assessed using differential scanning calorimetry (DSC), for example as discussed in Bruylants et al. (*Differential Scanning Calorimetry in Life Sciences: Thermodynamics, Stability, Molecular Recognition and Application in Drug Design,* 2005 Curr. Med. Chem. 12: 2011-2020) and Calorimetry Sciences Corporation's "Characterizing Protein stability by DSC" (Life Sciences Application Note, Doc. No. 2021102136 February 2006) or by differential scanning fluorimetry (DSF). An increase in stability may be characterized as an at least about 5° C. increase in thermal transition midpoint ($T_m$), as assessed by DSC or DSF. See, for example, Thomas et al., *Effect of single-point mutations on the stability and immunogenicity of a recombinant ricin A chain subunit vaccine antigen,* 2013 Hum. Vaccin. Immunother. 9(4): 744-752.

It will be understood that the invention is described above by way of example only and modifications may be made whilst remaining within the scope and spirit of the invention.

SEQUENCES

SEQ ID NO: 1 [v1.13 mature polypeptide from strain M982]
CSSGGGGVAADIGAGLADALTAPLDHKDKGLQSLTLDQSVRKNEKLKLAAQGAEKTYGNGDSLNTGKLKNDKVSRFDFIR
QIEVDGKLITLESGEFQVYKQSHSALTALQTEQVQDSEDSGKMVAKRQFRIGDIAGEHTSFDKLPKGGSATYRGTAFGSDD
AGGKLTYTIDFAAKQGHGKIEHLKSPELNVELATAYIKPDEKRHAVISGSVLYNQDEKGSYSLGIFGGQAQEVAGSAEVETAN
GIHHIGLAAKQ.

SEQ ID NO: 2 [v1.13 ΔG]
VAADIGAGLADALTAPLDHKDKGLQSLTLDQSVRKNEKLKLAAQGAEKTYGNGDSLNTGKLKNDKVSRFDFIRQIEVDGKLI
TLESGEFQVYKQSHSALTALQTEQVQDSEDSGKMVAKRQFRIGDIAGEHTSFDKLPKGGSATYRGTAFGSDDAGGKLTYTI
DFAAKQGHGKIEHLKSPELNVELATAYIKPDEKRHAVISGSVLYNQDEKGSYSLGIFGGQAQEVAGSAEVETANGIHHIGLA
AKQ

SEQ ID NO: 3 [v1.13 ΔG (E211A/E232A)]
VAADIGAGLADALTAPLDHKDKGLQSLTLDQSVRKNEKLKLAAQGAEKTYGNGDSLNTGKLKNDKVSRFDFIRQIEVDGKLI
TLESGEFQVYKQSHSALTALQTEQVQDSEDSGKMVAKRQFRIGDIAGEHTSFDKLPKGGSATYRGTAFGSDDAGGKLTYTI
DFAAKQGHGKIEHLKSPELNVELATAYIKPDEKRHAVISGSVLYNQDAKGSYSLGIFGGQAQEVAGSAAVETANGIHHIGLA
AKQ

SEQ ID NO: 4 [v1.13 ΔG (E211A/S216R)]
VAADIGAGLADALTAPLDHKDKGLQSLTLDQSVRKNEKLKLAAQGAEKTYGNGDSLNTGKLKNDKVSRFDFIRQIEVDGKLI
TLESGEFQVYKQSHSALTALQTEQVQDSEDSGKMVAKRQFRIGDIAGEHTSFDKLPKGGSATYRGTAFGSDDAGGKLTYTI
DFAAKQGHGKIEHLKSPELNVELATAYIKPDEKRHAVISGSVLYNQDAKGSYRLGIFGGQAQEVAGSAEVETANGIHHIGLA
AKQ

SEQ ID NO: 5 [v1.15 mature polypeptide from strain NM452]
CSSGGGGSGGGGVAADIGAGLADALTAPLDHKDKGLKSLTLEDSISQNGTLTLSAQGAERTFKAGDKDNSLNTGKLKNDKI
SRFDFIRQIEVDGQLITLESGEFQVYKQSHSALTALQTEQVQDSEHSGKMVAKRQFRIGDIVGEHTSFGKLPKDVMATYRGT
AFGSDDAGGKLTYTIDFAAKQGHGKIEHLKSPELNVDLAAADIKPDEKHHAVISGSVLYNQAEKGSYSLGIFGGQAQEVAGS
AEVETANGIRHIGLAAKQ SEQ ID NO: 6 [v1.15 ΔG]
VAADIGAGLADALTAPLDHKDKGLKSLTLEDSISQNGTLTLSAQGAERTFKAGDKDNSLNTGKLKNDKISRFDFIRQIEVDGQ
LITLESGEFQVYKQSHSALTALQ.TEQVQDSEHSGKMVAKRQFRIGDIVGEHTSFGKLPKDVMATYRGTAFGSDDAGGKLTY
TIDFAAKQGHGKIEHLKSPELNVDLAAADIKPDEKHHAVISGSVLYNQAEKGSYSLGIFGGQAQEVAGSAEVETANGIRHIGL
AAKQ.

SEQ ID NO: 7 [v1.15 ΔG (S219R)]
VAADIGAGLADALTAPLDHKDKGLKSLTLEDSISQNGTLTLSAQGAERTFKAGDKDNSLNTGKLKNDKISRFDFIRQIEVDGQ
LITLESGEFQVYKQSHSALTALQTEQVQDSEHSGKMVAKRQFRIGDIVGEHTSFGKLPKDVMATYRGTAFGSDDAGGKLTY
TIDFAAKQGHGKIEHLKSPELNVDLAAADIKPDEKHHAVISGSVLYNQAEKGSYRLGIFGGQAQEVAGSAEVETANGIRHIG
LAAKQ

-continued

SEQUENCES

SEQ ID NO: 8 [v1.15 ΔG (E214A/S219R)]
VAADIGAGLADALTAPLDHKDKGLKSLTLEDSISQNGTLTLSAQGAERTFKAGDKDNSLNTGKLKNDKISRFDFIRQIEVDGQ
LITLESGEFQVYKQSHSALTALQTEQVQDSEHSGKMVAKRQFRIGDIVGEHTSFGKLPKDVMATYRGTAFGSDDAGGKLTY
TIDFAAKQGHGKIEHLKSPELNVDLAAADIKPDEKHHAVISGSVLYNQAAKGSYRLGIFGGQAQEVAGSAEVETANGIRHIG
LAAKQ

SEQ ID NO: 9 [v1.15 ΔG (E214A/E235A)]
VAADIGAGLADALTAPLDHKDKGLKSLTLEDSISQNGTLTLSAQGAERTFKAGDKDNSLNTGKLKNDKISRFDFIRQIEVDGQ
LITLESGEFQVYKQSHSALTALQTEQVQDSEHSGKMVAKRQFRIGDIVGEHTSFGKLPKDVMATYRGTAFGSDDAGGKLTY
TIDFAAKQGHGKIEHLKSPELNVDLAAADIKPDEKHHAVISGSVLYNQAAKGSYSLGIFGGQAQEVAGSAAVETANGIRHIG
LAAKQ

SEQ ID NO: 10 [v2 wt from strain 2996]
MNRTAFCCLSLTAALILTACSSGGGGVAADIGAGLADALTAPLDHKDKSLQSLTLDQSVRKNEKLKLAAQGAEKTYGNGDS
LNTGKLKNDKVSRFDFIRQIEVDGQLITLESGEFQIYKQDHSAVVALQIEKINNPDKIDSLINQRSFLVSGLGGEHTAFNQLPD
GKAEYHGKAFSSDDAGGKLTYTIDFAAKQGHGKIEHLKTPEQNVELAAAELKADEKSHAVILGDTRYGSEEKGTYHLALFGD
RAQEIAGSATVKIGEKVHEIGIAGKQ SEQ ID NO: 11 [v2 mature polypeptide]
CSSGGGGVAADIGAGLADALTAPLDHKDKSLQSLTLDQSVRKNEKLKLAAQGAEKTYGNGDSLNTGKLKNDKVSRFDFIRQ
IEVDGQLITLESGEFQIYKQDHSAVVALQIEKINNPDKIDSLINQRSFLVSGLGGEHTAFNQLPDGKAEYHGKAFSSDDAGGK
LTYTIDFAAKQGHGKIEHLKTPEQNVELAAAELKADEKSHAVILGDTRYGSEEKGTYHLALFGDRAQEIAGSATVKIGEKVHEI
GIAGKQ SEQ ID NO: 12 [v2 ΔG]
VAADIGAGLADALTAPLDHKDKSLQSLTLDQSVRKNEKLKLAAQGAEKTYGNGDSLNTGKLKNDKVSRFDFIRQIEVDGQLI
TLESGEFQIYKQDHSAVVALQIEKINNPDKIDSLINQRSFLVSGLGGEHTAFNQLPDGKAEYHGKAFSSDDAGGKLTYTIDFA
AKQGHGKIEHLKTPEQNVELAAAELKADEKSHAVILGDTRYGSEEKGTYHLALFGDRAQEIAGSATVKIGEKVHEIGIAGKQ SEQ ID NO: 13 [v3 wt from strain M1239]
MNRTAFCCLSLTTALILTACSSGGGGSGGGGVAADIGTGLADALTAPLDHKDKGLKSLTLEDSIPQNGTLTLSAQGAEKTFK
AGDKDNSLNTGKLKNDKISRFDFVQKIEVDGQTITLASGEFQIYKQNHSAVVALQIEKINNPDKTDSLINQRSFLVSGLGGEH
TAFNQLPGGKAEYHGKAFSSDDPNGRLHYSIDFTKKQGYGRIEHLKTLEQNVELAAAELKADEKSHAVILGDTRYGSEEKGT
YHLALFGDRAQEIAGSATVKIGEKVHEIGIAGKQ SEQ ID NO: 14 [v3 mature]
CSSGGGGSGGGGVAADIGTGLADALTAPLDHKDKGLKSLTLEDSIPQNGTLTLSAQGAEKTFKAGDKDNSLNTGKLKNDKI
SRFDFVQKIEVDGQTITLASGEFQIYKQNHSAVVALQIEKINNPDKTDSLINQRSFLVSGLGGEHTAFNQLPGGKAEYHGKAF
SSDDPNGRLHYSIDFTKKQGYGRIEHLKTLEQNVELAAAELKADEKSHAVILGDTRYGSEEKGTYHLALFGDRAQEIAGSATV
KIGEKVHEIGIAGKQ SEQ ID NO: 15 [v3 ΔG]
VAADIGTGLADALTAPLDHKDKGLKSLTLEDSIPQNGTLTLSAQGAEKTFKAGDKDNSLNTGKLKNDKISRFDFVQKIEVDG
QTITLASGEFQIYKQNHSAVVALQIEKINNPDKTDSLINQRSFLVSGLGGEHTAFNQLPGGKAEYHGKAFSSDDPNGRLHYSI
DFTKKQGYGRIEHLKTLEQNVELAAAELKADEKSHAVILGDTRYGSEEKGTYHLALFGDRAQEIAGSATVKIGEKVHEIGIAG
KQ SEQ ID NO: 16 [v2 ΔG S32V/L123R]
VAADIGAGLADALTAPLDHKDKSLQSLTLDQVVRKNEKLKLAAQGAEKTYGNGDSLNTGKLKNDKVSRFDFIRQIEVDGQLI
TLESGEFQIYKQDHSAVVALQIEKINNPDKIDSLINQRSFRVSGLGGEHTAFNQLPDGKAEYHGKAFSSDDAGGKLTYTIDFA
AKQGHGKIEHLKTPEQNVELAAAELKADEKSHAVILGDTRYGSEEKGTYHLALFGDRAQEIAGSATVKIGEKVHEIGIAGKQ SEQ ID NO: 17 [v3 ΔG S32V/L126R]
VAADIGTGLADALTAPLDHKDKGLKSLTLEDVIPQNGTLTLSAQGAEKTFKAGDKDNSLNTGKLKNDKISRFDFVQKIEVDG
QTITLASGEFQIYKQNHSAVVALQIEKINNPDKTDSLINQRSFRVSGLGGEHTAFNQLPGGKAEYHGKAFSSDDPNGRLHYSI
DFTKKQGYGRIEHLKTLEQNVELAAAELKADEKSHAVILGDTRYGSEEKGTYHLALFGDRAQEIAGSATVKIGEKVHEIGIAG
KQ SEQ ID NO: 18 [(23S_1.13_E211A/E232A)]
VAADIGAGLADALTAPLDHKDKSLQSLTLDQVVRKNEKLKLAAQGAEKTYGNGDSLNTGKLKNDKVSRFDFIRQIEVDGQLI
TLESGEFQIYKQDHSAVVALQIEKINNPDKIDSLINQRSFRVSGLGGEHTAFNQLPDGKAEYHGKAFSSDDAGGKLTYTIDFA
AKQGHGKIEHLKTPEQNVELAAAELKADEKSHAVILGDTRYGSEEKGTYHLALFGDRAQEIAGSATVKIGEKVHEIGIAGKQ
GSGGGGVAADIGTGLADALTAPLDHKDKGLKSLTLEDVIPQNGTLTLSAQGAEKTFKAGDKDNSLNTGKLKNDKISRFDFV
QKIEVDGQTITLASGEFQIYKQNHSAVVALQIEKINNPDKTDSLINQRSFRVSGLGGEHTAFNQLPGGKAEYHGKAFSSDDP
NGRLHYSIDFTKKQGYGRIEHLKTLEQNVELAAAELKADEKSHAVILGDTRYGSEEKGTYHLALFGDRAQEIAGSATVKIGEK
VHEIGIAGKQGSGGGGVAADIGAGLADALTAPLDHKDKGLKSLTLDQLSLTLDQSVRKNEKLKLAAQGAEKTYGNGDSLNTGKLKND
KVSRFDFIRQIEVDGKLITLESGEFQVYKQSHSALTALQTEQVQDSEDSGKMVAKRQFRIGDIAGEHTSFDKLPKGGSATYR
GTAFGSDDAGGKLTYTIDFAAKQGHGKIEHLKSPELNVELATAYIKPDEKRHAVISGSVLYNQDAKGSYSLGIFGGQAQEVA
GSAAVETANGIHHIGLAAKQ SEQ ID NO: 19 [23S_1.13_E211A/S216R]
VAADIGAGLADALTAPLDHKDKSLQSLTLDQVVRKNEKLKLAAQGAEKTYGNGDSLNTGKLKNDKVSRFDFIRQIEVDGQLI
TLESGEFQIYKQDHSAVVALQIEKINNPDKIDSLINQRSFRVSGLGGEHTAFNQLPDGKAEYHGKAFSSDDAGGKLTYTIDFA
AKQGHGKIEHLKTPEQNVELAAAELKADEKSHAVILGDTRYGSEEKGTYHLALFGDRAQEIAGSATVKIGEKVHEIGIAGKQ
GSGGGGVAADIGTGLADALTAPLDHKDKGLKSLTLEDVIPQNGTLTLSAQGAEKTFKAGDKDNSLNTGKLKNDKISRFDFV
QKIEVDGQTITLASGEFQIYKQNHSAVVALQIEKINNPDKTDSLINQRSFRVSGLGGEHTAFNQLPGGKAEYHGKAFSSDDP
NGRLHYSIDFTKKQGYGRIEHLKTLEQNVELAAAELKADEKSHAVILGDTRYGSEEKGTYHLALFGDRAQEIAGSATVKIGEK

| SEQUENCES |
|---|
| VHEIGIAGKQGSGGGGVAADIGAGLADALTAPLDHKDKGLQSLTLDQSVRKNEKLKLAAQGAEKTYGNGDSLNTGKLKND<br>KVSRFDFIRQIEVDGKLITLESGEFQVYKQSHSALTALQTEQVQDSEDSGKMVAKRQFRIGDIAGEHTSFDKLPKGGSATYR<br>GTAFGSDSDAGGKLTYTIDFAAKQGHGKIEHLKSPELNVELATAYIKPDEKRHAVISGSVLYNQAKGSYRLGIFGGQAQEVA<br>GSAEVETANGIHHIGLAAKQ<br><br>SEQ ID NO: 20 [23S_1.15_S219R]<br>VAADIGAGLADALTAPLDHKDKSLQSLTLDQVVRKNEKLKLAAQGAEKTYGNGDSLNTGKLKNDKVSRFDFIRQIEVDGQLI<br>TLESGEFQIYKQDHSAVVALQIEKINNPDKIDSLINQRSFRVSGLGGEHTAFNQLPDGKAEYHGKAFSSDDAGGKLTYTIDFA<br>AKQGHGKIEHLKTPEQNVELAAAELKADEKSHAVILGDTRYGSEEKGTYHLALFGDRAQEIAGSATVKIGEKVHEIGIAGKQ<br>GSGGGGVAADIGTGLADALTAPLDHKDKGLKSLTLEDVIPQNGTLTLSAQGAEKTFKAGDKDNSLNTGKLKNDKISRFDFV<br>QKIEVDGQTITLASGEFQIYKQNHSAVVALQIEKINNPDKTDSLINQRSFRVSGLGGEHTAFNQLPGGKAEYHGKAFSSDDP<br>NGRLHYSIDFTKKQGYGRIEHLKTLEQNVELAAAELKADEKSHAVILGDTRYGSEEKGTYHLALFGDRAQEIAGSATVKIGEK<br>VHEIGIAGKQGSGGGGVAADIGAGLADALTAPLDHKDKGLKSLTLEDSISQNGTLTLSAQGAERTFKAGDKDNSLNTGKLK<br>NDKISRFDFIRQIEVDGQLITLESGEFQVYKQSHSALTALQTEQVQDSEHSGKMVAKRQFRIGDIVGEHTSFGKLPKDVMAT<br>YRGTAFGSDDAGGKLTYTIDFAAKQGHGKIEHLKSPELNVDLAAADIKPDEKHHAVISGSVLYNQAEKGSYRLGIFGGQAQE<br>VAGSAEVETANGIRHIGLAAKQ<br><br>SEQ ID NO: 21 [23S_1.15_E214A/S219R]<br>VAADIGAGLADALTAPLDHKDKSLQSLTLDQVVRKNEKLKLAAQGAEKTYGNGDSLNTGKLKNDKVSRFDFIRQIEVDGQLI<br>TLESGEFQIYKQDHSAVVALQIEKINNPDKIDSLINQRSFRVSGLGGEHTAFNQLPDGKAEYHGKAFSSDDAGGKLTYTIDFA<br>AKQGHGKIEHLKTPEQNVELAAAELKADEKSHAVILGDTRYGSEEKGTYHLALFGDRAQEIAGSATVKIGEKVHEIGIAGKQ<br>GSGGGGVAADIGTGLADALTAPLDHKDKGLKSLTLEDVIPQNGTLTLSAQGAEKTFKAGDKDNSLNTGKLKNDKISRFDFV<br>QKIEVDGQTITLASGEFQIYKQNHSAVVALQIEKINNPDKTDSLINQRSFRVSGLGGEHTAFNQLPGGKAEYHGKAFSSDDP<br>NGRLHYSIDFTKKQGYGRIEHLKTLEQNVELAAAELKADEKSHAVILGDTRYGSEEKGTYHLALFGDRAQEIAGSATVKIGEK<br>VHEIGIAGKQGSGGGGVAADIGAGLADALTAPLDHKDKGLKSLTLEDSISQNGTLTLSAQGAERTFKAGDKDNSLNTGKLK<br>NDKISRFDFIRQIEVDGQLITLESGEFQVYKQSHSALTALQTEQVQDSEHSGKMVAKRQFRIGDIVGEHTSFGKLPKDVMAT<br>YRGTAFGSDDAGGKLTYTIDFAAKQGHGKIEHLKSPELNVDLAAADIKPDEKHHAVISGSVLYNQAAKGSYRLGIFGGQAQE<br>VAGSAEVETANGIRHIGLAAKQ<br><br>SEQ ID NO: 22 [23S_1.15_ E214A/E235A]<br>VAADIGAGLADALTAPLDHKDKSLQSLTLDQVVRKNEKLKLAAQGAEKTYGNGDSLNTGKLKNDKVSRFDFIRQIEVDGQLI<br>TLESGEFQIYKQDHSAVVALQIEKINNPDKIDSLINQRSFRVSGLGGEHTAFNQLPDGKAEYHGKAFSSDDAGGKLTYTIDFA<br>AKQGHGKIEHLKTPEQNVELAAAELKADEKSHAVILGDTRYGSEEKGTYHLALFGDRAQEIAGSATVKIGEKVHEIGIAGKQ<br>GSGGGGVAADIGTGLADALTAPLDHKDKGLKSLTLEDVIPQNGTLTLSAQGAEKTFKAGDKDNSLNTGKLKNDKISRFDFV<br>QKIEVDGQTITLASGEFQIYKQNHSAVVALQIEKINNPDKTDSLINQRSFRVSGLGGEHTAFNQLPGGKAEYHGKAFSSDDP<br>NGRLHYSIDFTKKQGYGRIEHLKTLEQNVELAAAELKADEKSHAVILGDTRYGSEEKGTYHLALFGDRAQEIAGSATVKIGEK<br>VHEIGIAGKQGSGGGGVAADIGAGLADALTAPLDHKDKGLKSLTLEDSISQNGTLTLSAQGAERTFKAGDKDNSLNTGKLK<br>NDKISRFDFIRQIEVDGQLITLESGEFQVYKQSHSALTALQTEQVQDSEHSGKMVAKRQFRIGDIVGEHTSFGKLPKDVMAT<br>YRGTAFGSDDAGGKLTYTIDFAAKQGHGKIEHLKSPELNVDLAAADIKPDEKHHAVISGSVLYNQAAKGSYSLGIFGGQAQE<br>VAGSAAEVETANGIRHIGLAAKQ<br><br>SEQ ID NO: 23 [v1.1 ΔG + His tag]<br>VAADIGAGLADALTAPLDHKDKGLQSLTLDQSVRKNEKLKLAAQGAEKTYGNGDSLNTGKLKNDKVSRFDFIRQIEVDGQLI<br>TLESGEFQVYKQSHSALTAFQTEQIQDSEHSGKMVAKRQFRIGDIAGEHTSFDKLPEGGRATYRGTAFGSDDAGGKLTYTID<br>FAAKQGNGKIEHLKSPELGLAAKQLNVDLAAADIKPDGKRHAVISGSVLYNQAEKGSYSLGIFGGKAQEVAGSAEVKTVNGI<br>RHLEHHHHHH<br><br>SEQ ID NO: 24 [v1.13 ΔG + His tag]<br>VAADIGAGLADALTAPLDHKDKGLQSLTLDQSVRKNEKLKLAAQGAEKTYGNGDSLNTGKLKNDKVSRFDFIRQIEVDGKLI<br>TLESGEFQVYKQSHSALTALQTEQVQDSEDSGKMVAKRQFRIGDIAGEHTSFDKLPKGGSATYRGTAFGSDDAGGKLTYTI<br>DFAAKQGHGKIEHLKSPELNVELATAYIKPDEKRHAVISGSVLYNQDEKGSYSLGIFGGQAQEVAGSAEVETANGIHHIGLA<br>AKQLEHHHHHH<br><br>SEQ ID NO: 25 [v1.13 ΔG (E211A)]<br>VAADIGAGLADALTAPLDHKDKGLQSLTLDQSVRKNEKLKLAAQGAEKTYGNGDSLNTGKLKNDKVSRFDFIRQIEVDGKLI<br>TLESGEFQVYKQSHSALTALQTEQVQDSEDSGKMVAKRQFRIGDIAGEHTSFDKLPKGGSATYRGTAFGSDDAGGKLTYTI<br>DFAAKQGHGKIEHLKSPELNVELATAYIKPDEKRHAVISGSVLYNQAKGSYSLGIFGGQAQEVAGSAEVETANGIHHIGLA<br>AKQLEHHHHHH<br><br>SEQ ID NO: 26 [v1.13 ΔG (S216R)]<br>VAADIGAGLADALTAPLDHKDKGLQSLTLDQSVRKNEKLKLAAQGAEKTYGNGDSLNTGKLKNDKVSRFDFIRQIEVDGKLI<br>TLESGEFQVYKQSHSALTALQTEQVQDSEDSGKMVAKRQFRIGDIAGEHTSFDKLPKGGSATYRGTAFGSDDAGGKLTYTI<br>DFAAKQGHGKIEHLKSPELNVELATAYIKPDEKRHAVISGSVLYNQDEKGSYRLGIFGGQAQEVAGSAEVETANGIHHIGLA<br>AKQLEHHHHHH<br><br>SEQ ID NO: 27 [v1.15 ΔG + His tag]<br>VAADIGAGLADALTAPLDHKDKGLKSLTLEDSISQNGTLTLSAQGAERTFKAGDKDNSLNTGKLKNDKISRFDFIRQIEVDGQ<br>LITLESGEFQVYKQSHSALTALQTEQVQDSEHSGKMVAKRQFRIGDIVGEHTSFGKLPKDVMATYRGTAFGSDDAGGKLTY<br>TIDFAAKQGHGKIEHLKSPELNVDLAAADIKPDEKHHAVISGSVLYNQAEKGSYSLGIFGGQAQEVAGSAEVETANGIRHIGL<br>AAKQLEHHHHHH<br><br>SEQ ID NO: 28 [v1.15 ΔG (E214A) + His tag]<br>VAADIGAGLADALTAPLDHKDKGLKSLTLEDSISQNGTLTLSAQGAERTFKAGDKDNSLNTGKLKNDKISRFDFIRQIEVDGQ<br>LITLESGEFQVYKQSHSALTALQTEQVQDSEHSGKMVAKRQFRIGDIVGEHTSFGKLPKDVMATYRGTAFGSDDAGGKLTY<br>TIDFAAKQGHGKIEHLKSPELNVDLAAADIKPDEKHHAVISGSVLYNQAAKGSYSLGIFGGQAQEVAGSAEVETANGIRHIG<br>LAAKQLEHHHHHH |

```
SEQUENCES

SEQ ID NO: 29 [fHbp 231 wt fusion polypeptide]
VAADIGAGLADALTAPLDHKDKSLQSLTLDQSVRKNEKLKLAAQGAEKTYGNGDSLNTGKLKNDKVSFDFIRQIEVDGQLIT
LESGEFQIYKQDHSAVVALQIEKINNPDKIDSLINQRSFLVSGLGGEHTAFNQLPDGKAEYHGKAFSSDDAGGKLTYTIDFAA
KQGHGKIEHLKTPEQNVELAAAELKADEKSHAVILGDTRYGSEEKGTYHLALFGDRAQEIAGSATVKIGEKVHEIGIAGKQGS
GGGGVAADIGTGLADALTAPLDHKDKGLKSLTLEDSIPQNGTLTLSAQGAEKTFKAGDKDNSLNTGKLKNDKISRFDFVQKI
EVDGQTITLASGEFQIYKQNHSAVVALQIEKINNPDKTDSLINQRSFLVSGLGGEHTAFNQLPGGKAEYHGKAFSSDDPNGR
LHYSIDFTKKQGYGRIEHLKTLEQNVELAAAELKADEKSHAVILGDTRYGSEEKGTYHLALFGDRAQEIAGSATVKIGEKVHEI
GIAGKQGSGGGGVAADIGAGLADALTAPLDHKDKGLQSLTLDQSVRKNEKLKLAAQGAEKTYGNGSLNTGKLKNDKVSRF
DFIRQIEVDGQLITLESGEFQVYKQSHSALTAFQTEQIQDSEHSGKMVAKRQFRIGDIAGEHTSFDKLPEGGRATYRGTAFG
SDDAGGKLTYTIDFAAKQGNGKIEHLKSPELNVDLAAAIKPDGKRHAVISGSVLYNQAEKGSYSLGIFGKAQEVAGSAEVKT
VNGI RHIGLAAKQ SEQ ID NO: 30 [fHbp 231S fusion polypeptide]
VAADIGAGLADALTAPLDHKDKSLQSLTLDQVVRKNEKLKLAAQGAEKTYGNGDSLNTGKLKNDKVSFDFIRQIEVDGQLIT
LESGEFQIYKQDHSAVVALQIEKINNPDKIDSLINQRSFRVSGLGGEHTAFNQLPDGKAEYHGKAFSSDDAGGKLTYTIDFAA
KQGHGKIEHLKTPEQNVELAAAELKADEKSHAVILGDTRYGSEEKGTYHLALFGDRAQEIAGSATVKIGEKVHEIGIAGKQGS
GGGGVAADIGTGLADALTAPLDHKDKGLKSLTLEDVIPQNGTLTLSAQGAEKTFKAGDKDNSLNTGKLKNDKISRFDFVQKI
EVDGQTITLASGEFQIYKQNHSAVVALQIEKINNPDKTDSLINQRSFRVSGLGGEHTAFNQLPGGKAEYHGKAFSSDDPNG
RLHYSIDFTKKQGYGRIEHLKTLEQNVELAAAELKADEKSHAVILGDTRYGSEEKGTYHLALFGDRAQEIAGSATVKIGEKVHE
IGIAGKQGSGGGGVAADIGAGLADALTAPLDHKDKGLQSLTLDQSVSKNEKLKLAAQGAEKTYGNGSLNTGKLKNDKVSRF
DFIRQIEVDGQLITLESGEFQVYKQSHSALTAFQTEQIQDSEHSGKMVAKRQFRIGDIAGEHTSFDKLPEGGRATYRGTAFG
SDDAGGKLTYTIDFAAKQGNGKIEHLKSPELNVDLAAAIKPDGKRHAVISGSVLYNQAEKGSYSLGIFGKAQEVAGSAEVKT
VNGI RHIGLAAKQ SEQ ID NO: 31 [v1.13 full-length wt sequence]
MNRTAFCCFSLTAALILTACSSGGGGVAADIGAGLADALTAPLDHKDKGLQSLTLDQSVRKNEKLKLAAQGAEKTYGNGDS
LNTGKLKNDKVSRFDFIRQIEVDGKLITLESGEFQVYKQSHSALTALQTEQVQDSEDSGKMVAKRQFRIGDIAGEHTSFDKLP
KGGSATYRGTAFGSDDAGGKLTYTIDFAAKQGHGKIEHLKSPELNVELATAYIKPDEKRHAVISGSVLYNQDEKGSYSLGIFG
GQAQEVAGSAEVETANGIHHIGLAAKQ SEQ ID NO: 32 [v1.15 full-length wt sequence]
MNRTTFCCLSLTAALILTACSSGGGGSGGGGVAADIGAGLADALTAPLDHKDKGLKSLTLEDSISQNGTLTLSAQGAERTFK
AGDKDNSLNTGKLKNDKISRFDFIRQIEVDGQLITLESGEFQVYKQSHSALTALQTEQVQDSEHSGKMVAKRQFRIGDIVGE
HTSFGKLPKDVMATYRGTAFGSDDAGGKLTYTIDFAAKQGHGKIEHLKSPELNVDLAAADIKPDEKHHAVISGSVLYNQAE
KGSYSLGIFGGQAQEVAGSAEVETANGIRHIGLAAKQ SEQ ID NO: 33 [mature fHbp v1.1]
CSSGGGGVAADIGAGLADALTAPLDHKDKGLQSLTLDQSVRKNEKLKLAAQGAEKTYGNGDSLNTGKLKNDKVSRFDFIQI
EVDGQLITLESGEFQVYKQSHSALTAFQTEQIQDSEHSGKMVAKRQFRIGDIAGEHTSFDKLPEGGRATYRGTAFGSDDAG
GKLTYTIDFAAKQGNGKIEHLKSPELNVDLAAADIKPDGKRHAVISGSVLYNQAEKGSYSLGIFGGKAQEVAGSAEVKTVNGI
RHIGLAAKQ SEQ ID NO: 34 [optional N-terminal amino acid sequence]
MGPDSDRLQQRR
```

MODES FOR CARRYING OUT THE INVENTION

The invention will now be further defined by reference to the following non-limiting examples.

EXAMPLES

Example 1: Stability Analysis of Stabilized fHbp 231 Fusion Comprising Variant 1.13 Mutants As described above, Differential Scanning Calorimetry (DSC) provides information on thermal stability and domain folding of proteins, and is described in the literature, for example in Johnson (2013) *Arch Biochem Biophys* 531: 100-9 and Bruylants et al. *Current Medicinal Chemistry* 2005; 12:2011-20. DSC has previously been used to assess the stability of v2 fHbp (Johnson et al. *PLoS Pathogen* 2012; 8:e1002981). Suitable conditions for DSC to assess stability can use 20 µM of polypeptide in a buffered solution (e.g. 25 mM Tris) with a pH between 6 and 8 (e.g. 7-7.5) with 100-200 mM NaCl (e.g. 150 mM).

The present inventors used this technique to investigate the effect of mutating fHbp variant 1 sub-variants on 231S fusion protein stability.

The stabilized fHbp 231 fusion (termed "231S") used in this example includes variant 2 and variant 3 sequences comprising stabilising mutations. Specifically, the v2 component of the 231S fusion has the sequence of SEQ ID NO: 16, comprising both the S32V and L123R mutations. The v3 component of the 231S fusion has the sequence of SEQ ID NO: 17, comprising both the S32V and L126R mutations. The inventors varied the v1 component of the 231S fusion to investigate the effect on stability.

Each of the fHbp variant polypeptides comprises an N-terminal and a C-terminal domain, which can be clearly distinguished in DSC thermograms as two distinct transitions (peaks). While the Tm values corresponding to the C-terminal transitions of most fHbp variants are seen around 90° C., those of the N-terminal domains vary widely between different fHbp variants with the lowest values seen in the variant 2.1 wild type (42° C.) and the highest in var1.1 (70° C.).

Figure 2:
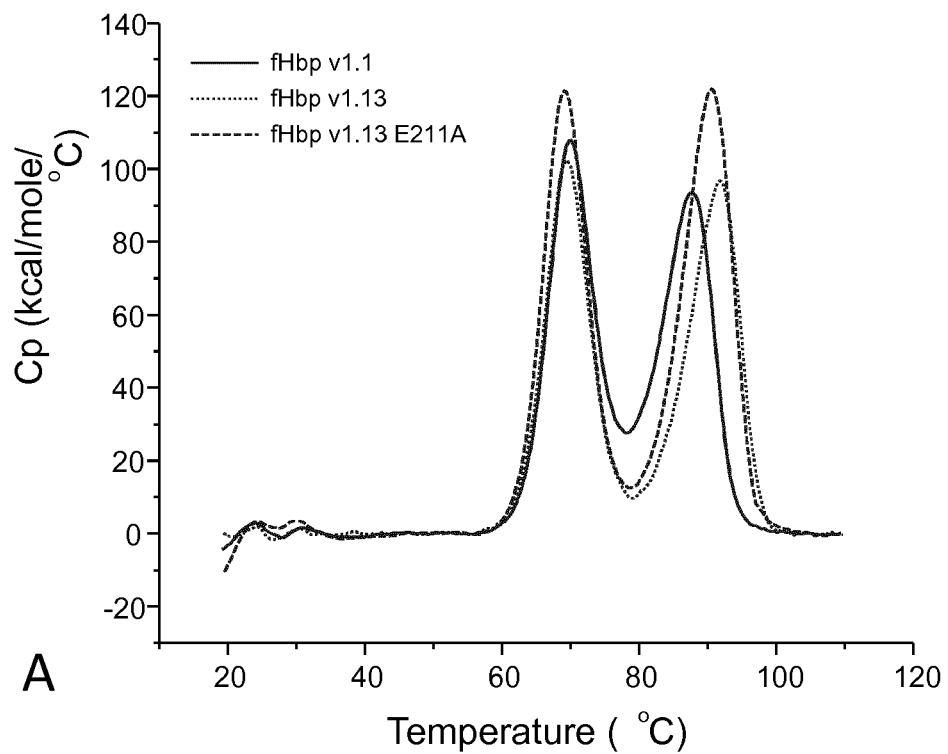
Figure 2:
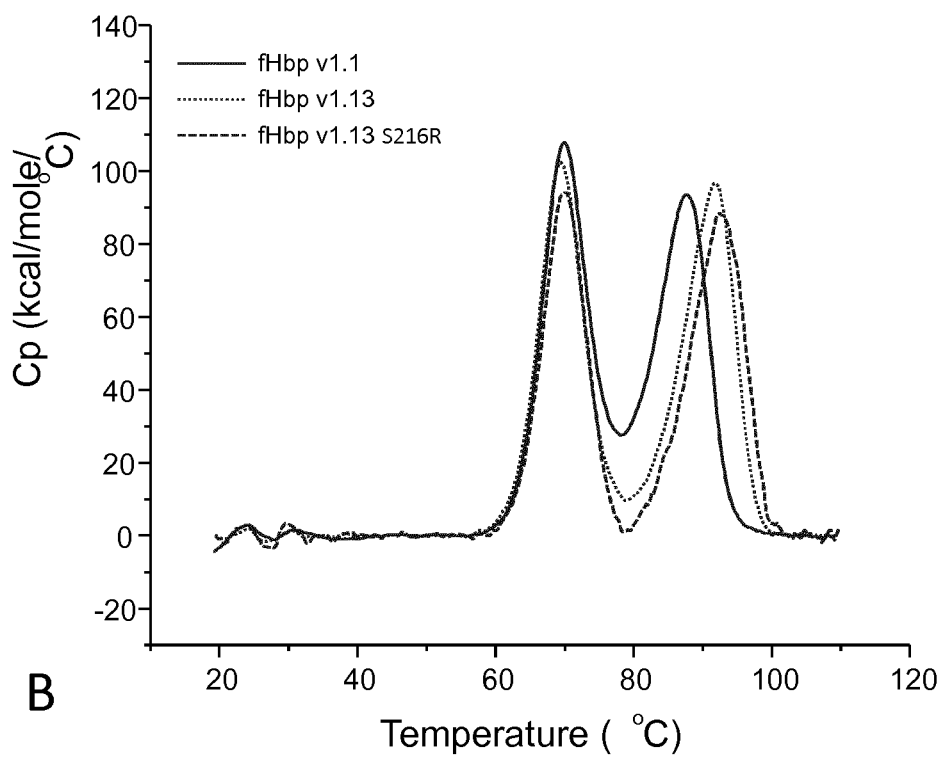
Figure 2:
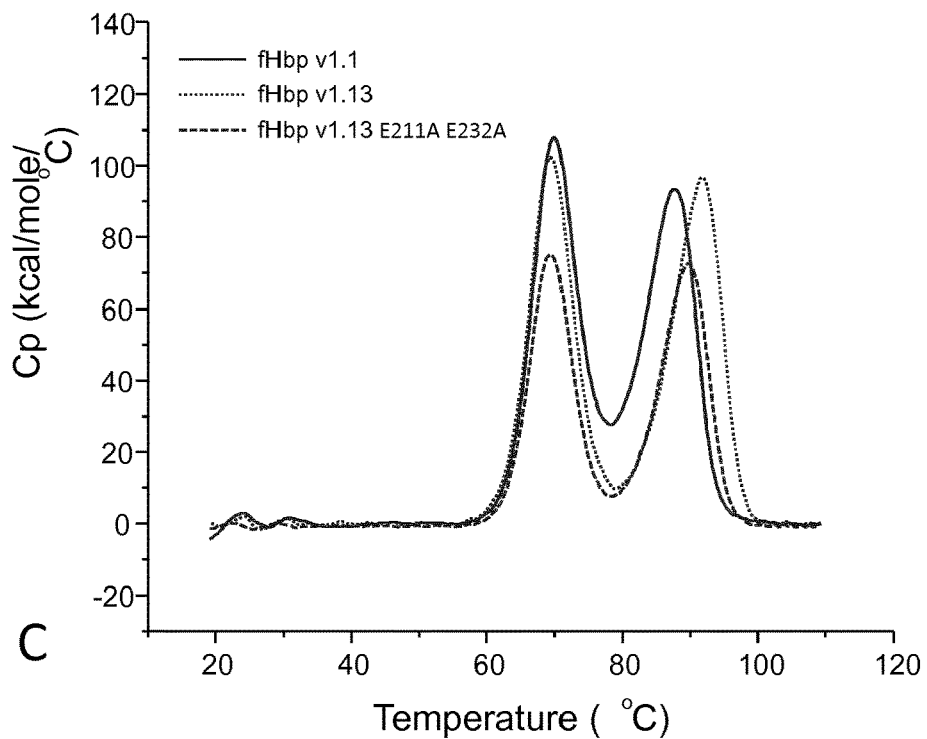
Figure 2:
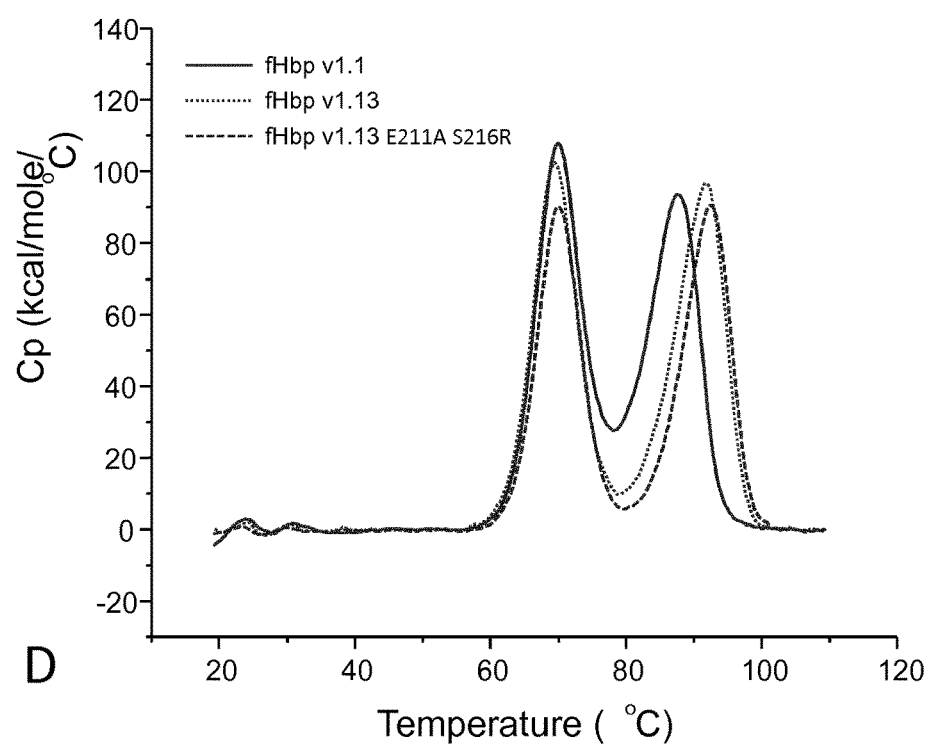

FIG. 2 shows four different thermograms comparing DSC data wherein the variant 1 component of the fHbp 231S fusion is:

fHbp v1.1 or fHbp v1.13 or (A) fHbp v.1.13 E211A (FIG. 2A);

fHbp v1.1 or fHbp v1.13 or (B) fHbp v1.13 S216R (FIG. 2B);

fHbp v1.1 or fHbp v1.13 or fHbp v.1.13 E211A/E232A (FIG. 2C); and fHbp v1.1 or fHbp v1.13 or fHbp v.1.13 E211A/S216R (FIG. 2D).

From each of these four thermograms it can be concluded that (i) fHbp units in the fusion constructs are folded correctly and ii) that the v1 mutations are effective in stabilising the fusion constructs, by causing an increase in C-terminal transition temperatures compared with the fusions comprising wildtype v1 sequences.

Example 2: Binding of fHbp Single Variant Mutants to hfH

The following polypeptides shown in Table 1 were generated (with the addition of a C-terminal His$_6$ tag where not already indicated as part of the referenced sequence) in order to investigate the effect of substitution mutations on the ability of fHbp variant 1 sub-variants 1.13 and 1.15 to reduce binding to human factor H (hfH):

TABLE 1

| Protein | SEQ ID N. # | purification | Purity % (SE_UPLC) |
|---|---|---|---|
| fHbp v1.1 | 23 | MATS3 | 98 |
| fHbp v1.13 | 24 | MenB 664 | 95 |
| fHbp V 1.13 E211A | 25 | MenB 672 | 98 |
| fHbp V 1.13 S216R | 26 | MenB 673 | 98 |
| fHbp V1.13 E211A/E232A | 3 | MenB 687 | 92 |
| fHbp V1.13 E211A/S216R | 4 | MenB 686 | 91 |
| fHbp v1.15 | 27 | MenB 669 | 82 |
| fHbp v1.15 E214A | 28 | MenB 679 | 85 |
| fHbp v1.15 E214A/E235A | 9 | MenB 680 | 86 |
| fHbp v1.15 E214A/S219R | 8 | MenB 682 | 82 |
| fHbp v1.15 S219R | 7 | MenB 683 | 83 |

The inventors investigated the binding of fHbp single variant mutants to hfH using surface plasmon resonance (SPR), which is a technology enabling detailed and quantitative studies of protein-protein interactions and determination of their equilibrium and kinetic parameters (as described for example in Karlsson et al. (1994) Methods 6:99-110).

The SPR-based binding method involves immobilization of a ligand on the surface of a sensor chip. The ligand of interest is immobilized on the surface of the sensor chip using well-defined chemistry allowing solutions with different concentrations of an analyte to flow over it and to characterize its interactions to the immobilized ligand. The SPR signal originates from changes in the refractive index at the surface of the gold sensor chip.

Monitoring the change in the SPR signal over time produces a sensorgram, a plot of the binding response (RU) versus time which allows different stages of a binding event to be visualized and evaluated.

During the injection of an analyte, the binding response increase is due to the formation of analyte-ligand complexes at the surface and the sensorgram is dominated by the association phase. Following injection, a steady state is reached, in which binding and dissociating molecules are in equilibrium. The decrease in response after analyte injection is terminated is due to dissociation of the complexes, defining the dissociation phase. Fitting the sensorgram data to an appropriate kinetic binding model allows calculation of kinetic parameters such as the association ($k_a$) and dissociation ($k_d$) rate constants, and the binding affinity of the tested interactions.

The inventors used the following experimental set-up:
Chip: CM-5 with ~400 RU of factor H 6-7 domain, immobilized by amine chemistry, 10 μg/ml in acetate buffer pH4.0 and with ~ 2500 RU of factor H, Human (Merck Millipore) immobilized by amine chemistry, 20 μg/ml in acetate buffer pH4.0
Running buffer: HBS-P 1×
Antigens analyzed: as shown in in Table 1
Antigens were applied at a fixed concentration of 250 nM
Contact time: 120 s, flow rate: 30 μl/min, Dissociation time: 120 s
Regeneration buffer: 100 mM glycine-HCl, 3M NaCl pH2.0.

Figure 3:
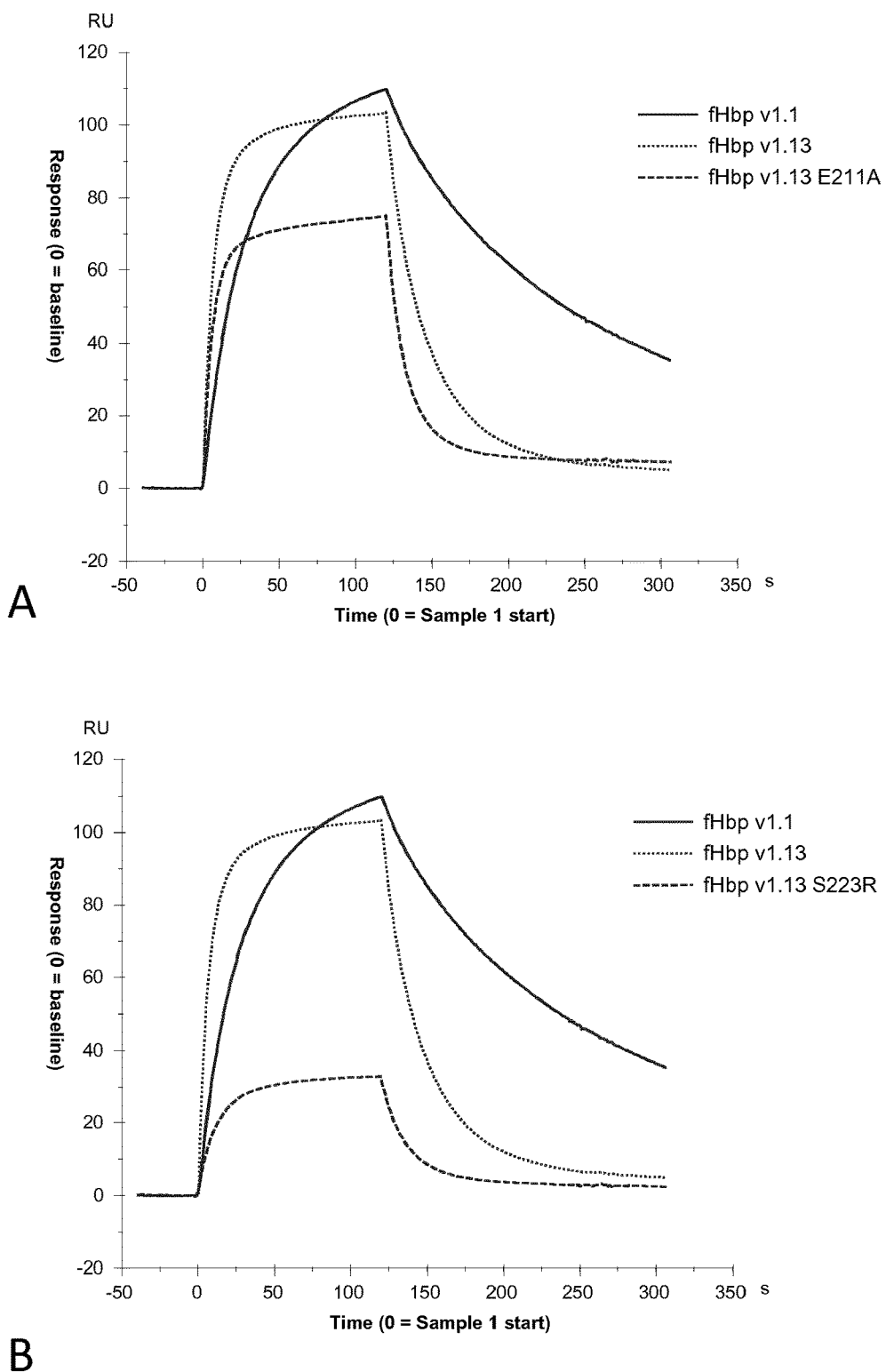
Figure 3:
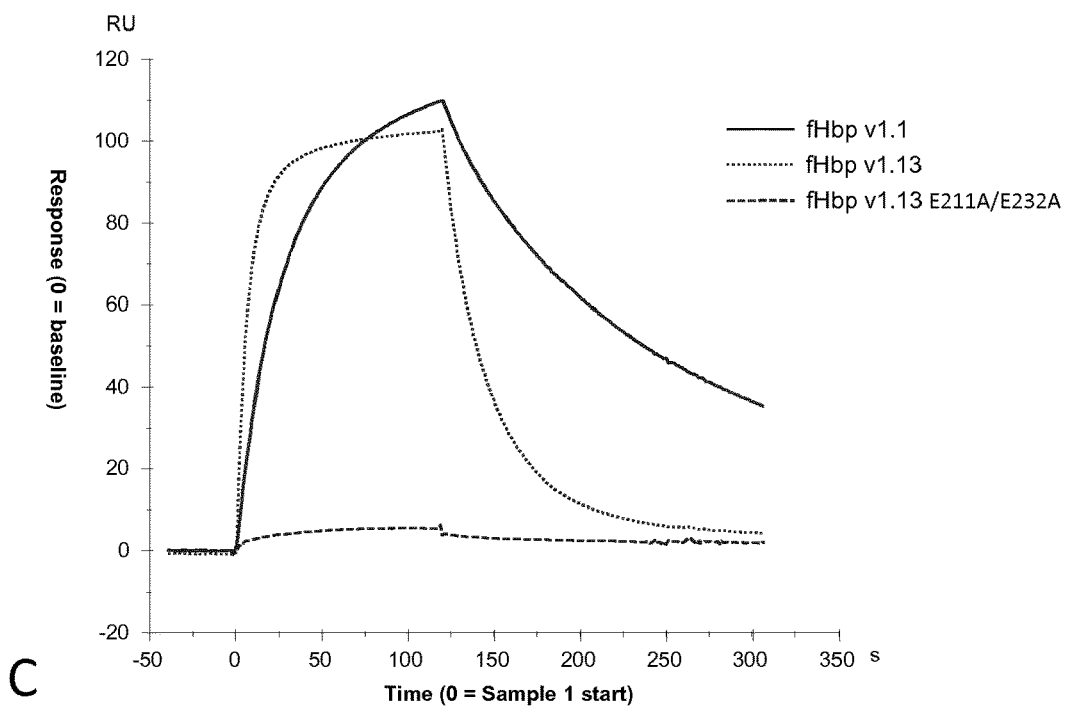
Figure 3:
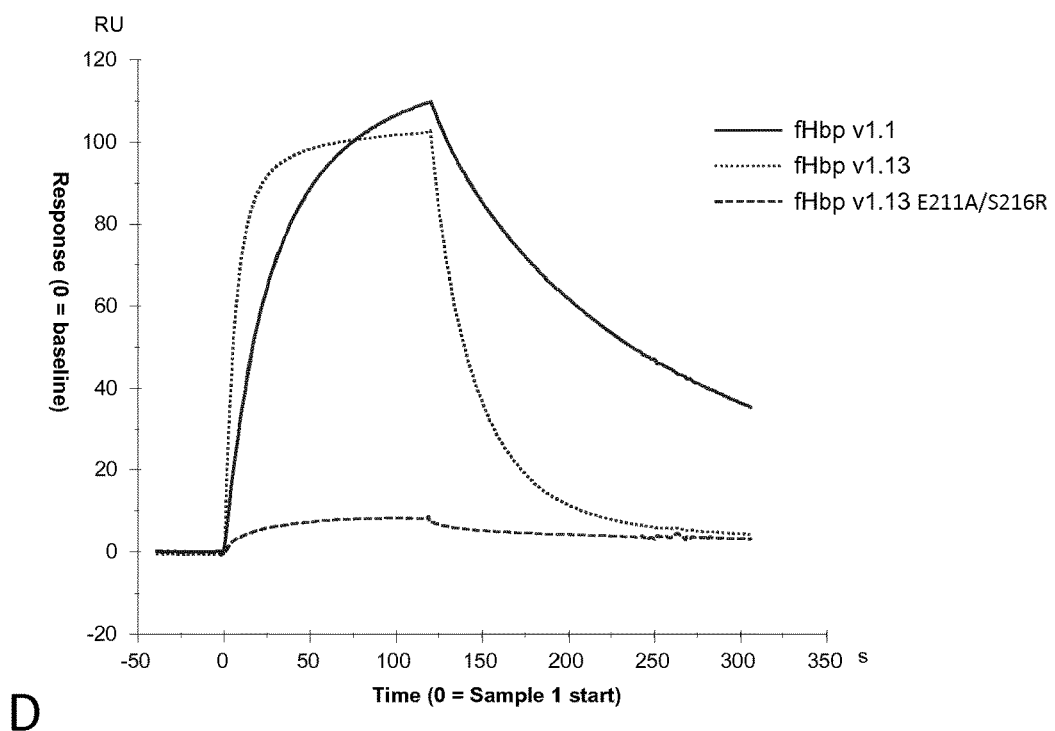

The data shown in FIG. 3 (A-D) compare the binding to factor H (hfH) domain 6-7 of fHbp v1.1 (the fHbp antigen present in BEXSERO®) and fHbp v1.13 (wildtype) with fHbp v.1.13 E211A (FIG. 3A), fHbp v1.13 S216R (FIG. 3B), fHbp v.1.13 E211A/E232A (FIG. 3C) and fHbp v.1.13 E211A/S216R (FIG. 3D).

A fragment of hfH containing only domains 6-7 has been shown to be sufficient to mimic the fHbp-hfH interaction (Schneider et al. (2009) Nature 458:890-893), thus providing a simplified model system to assess the affinity of fHbp mutants and constructs to hfH.

While the fHbp v1.13 single mutants show reduced fH binding compared with v.1.1 and wildtype v1.13 (see FIGS. 3A and 3B), the double mutants v1.13 E211A/E232A and v1.13 E211A/S216R display greatly reduced binding activity (see FIGS. 3C and 3D).

Figure 4:
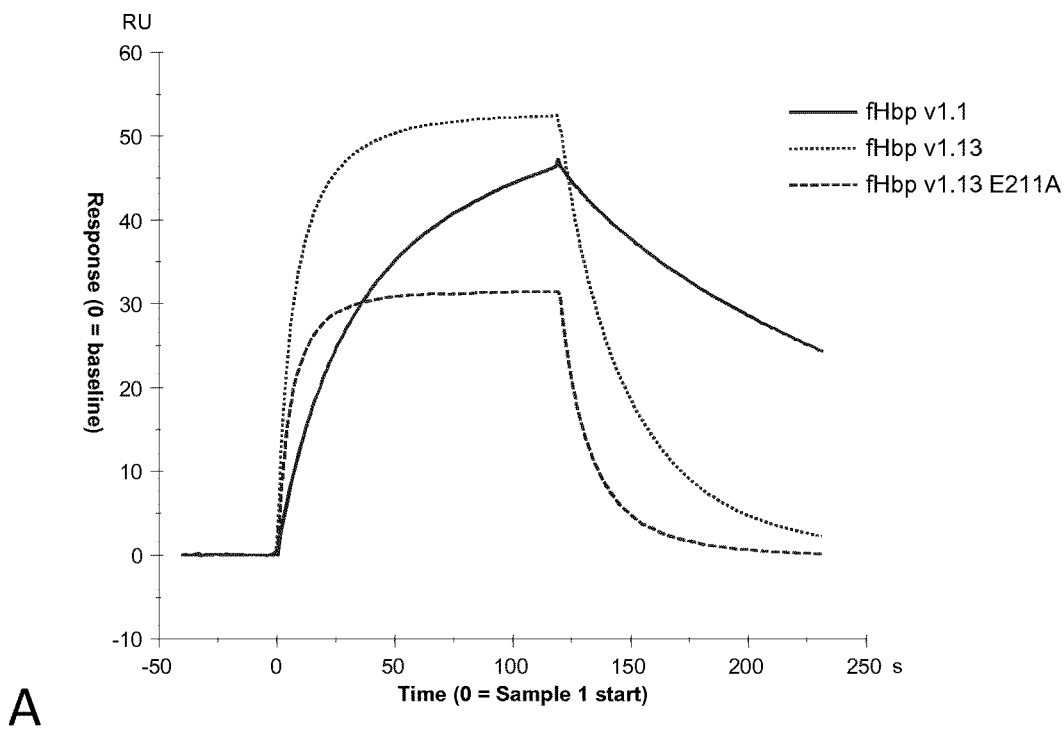
Figure 4:
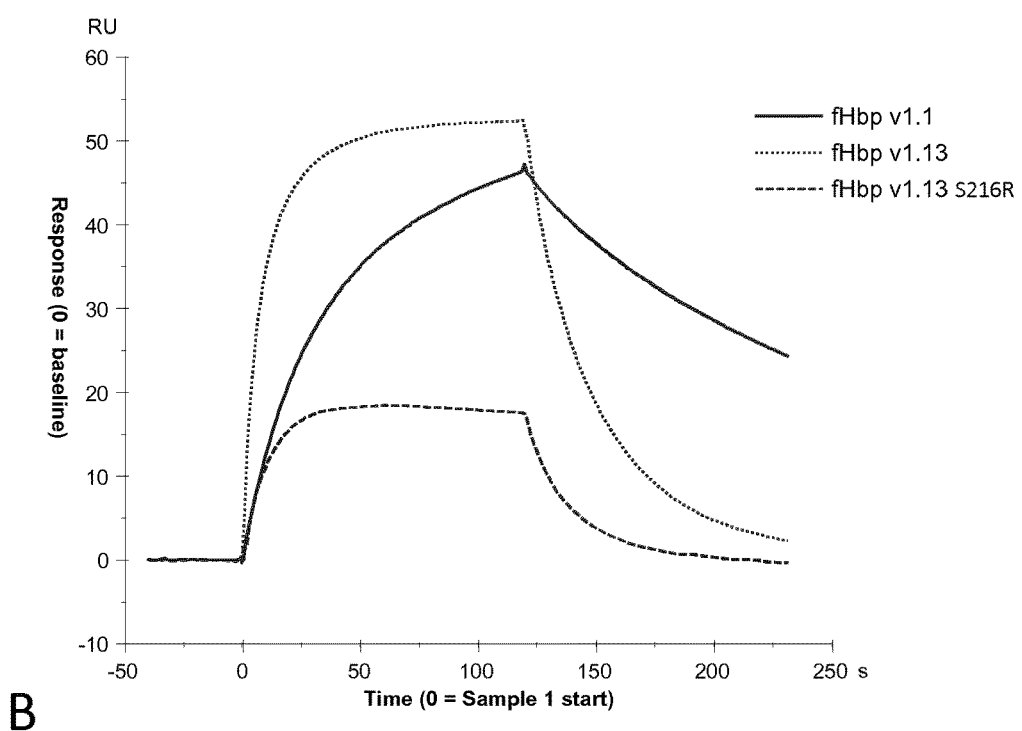
Figure 4:
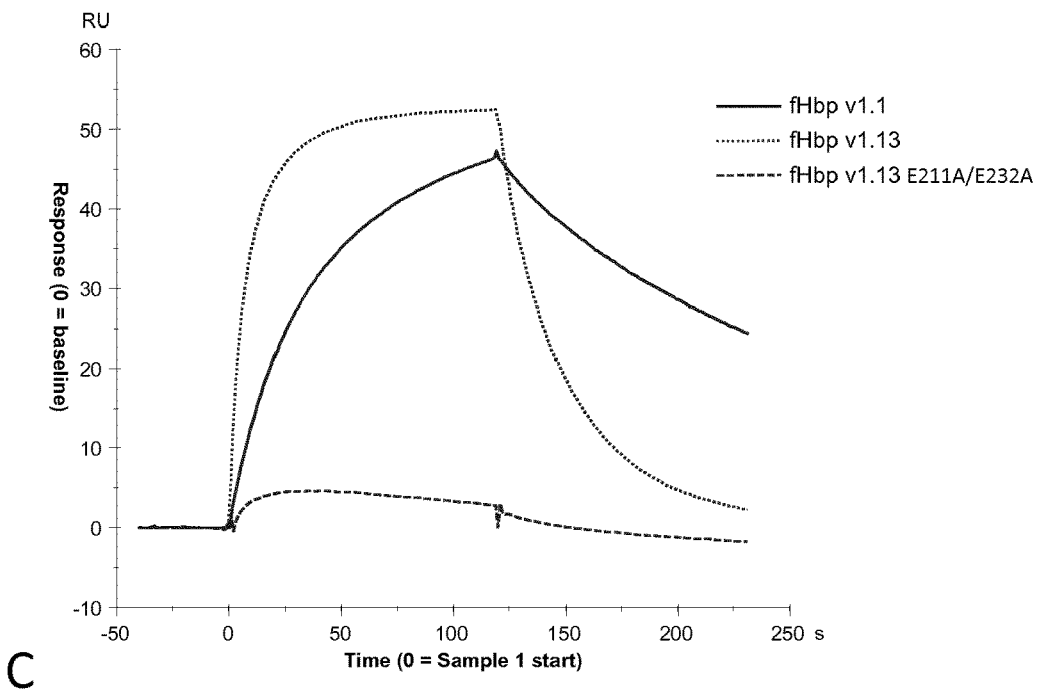
Figure 4:
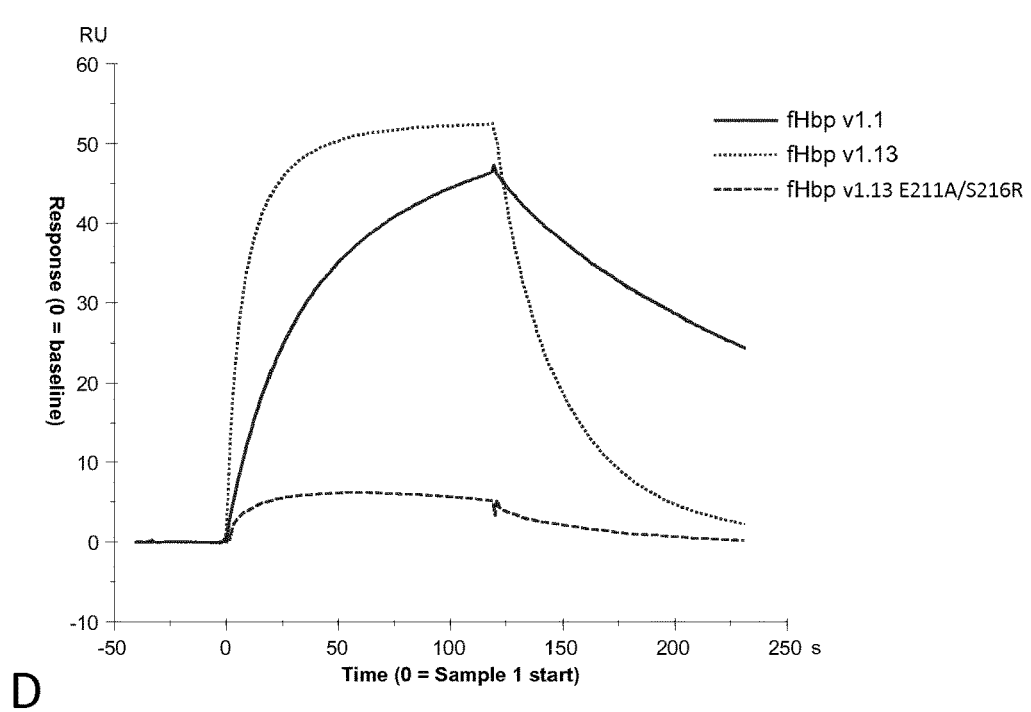

The data shown in FIG. 4 (A-D) compare the binding to the full-length factor H protein of fHbp v1.1 and fHbp v1.13 (wildtype) with fHbp v.1.13 E211A (FIG. 4A), fHbp v1.13 S216R (FIG. 4B), fHbp v.1.13 E211A/E232A (FIG. 4C) and fHbp v.1.13 E211A/S216R (FIG. 4D).

While the fHbp v1.13 single mutants show reduced fH binding compared with v.1.1 and wildtype v1.13 (see FIGS. 4A and 4B), the double mutants v1.13 E211A/E232A and v1.13 E211A/S216R display greatly reduced binding activity (see FIGS. 4C and 4D).

Figure 5:
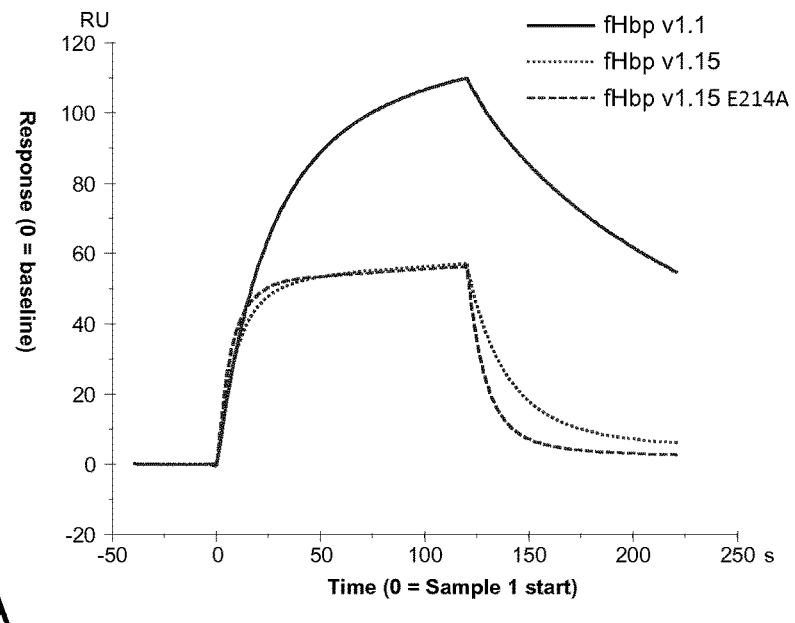
Figure 5:
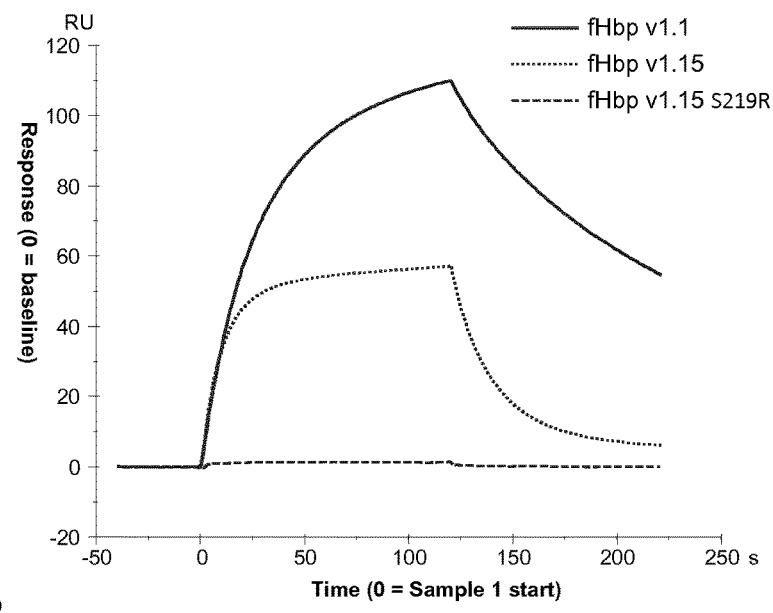
Figure 5:
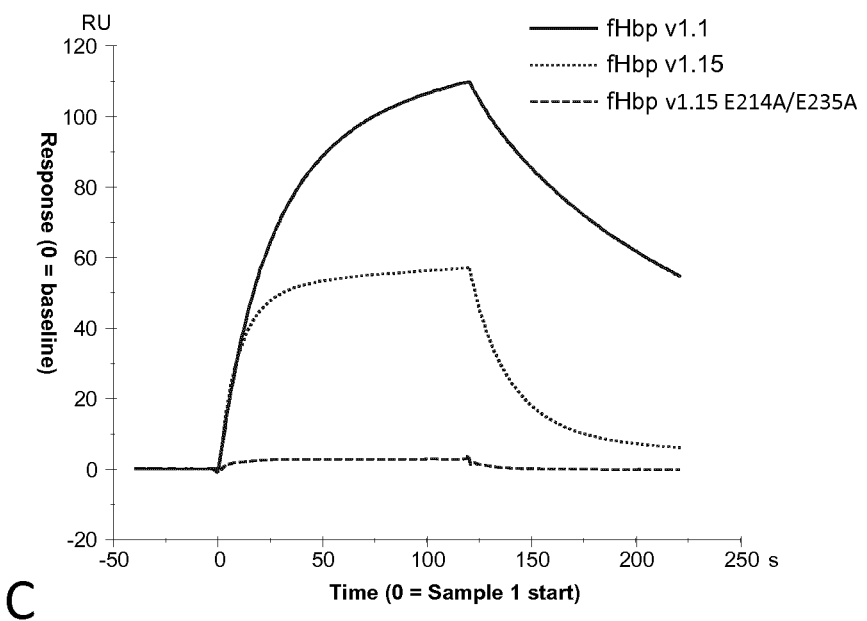
Figure 5:
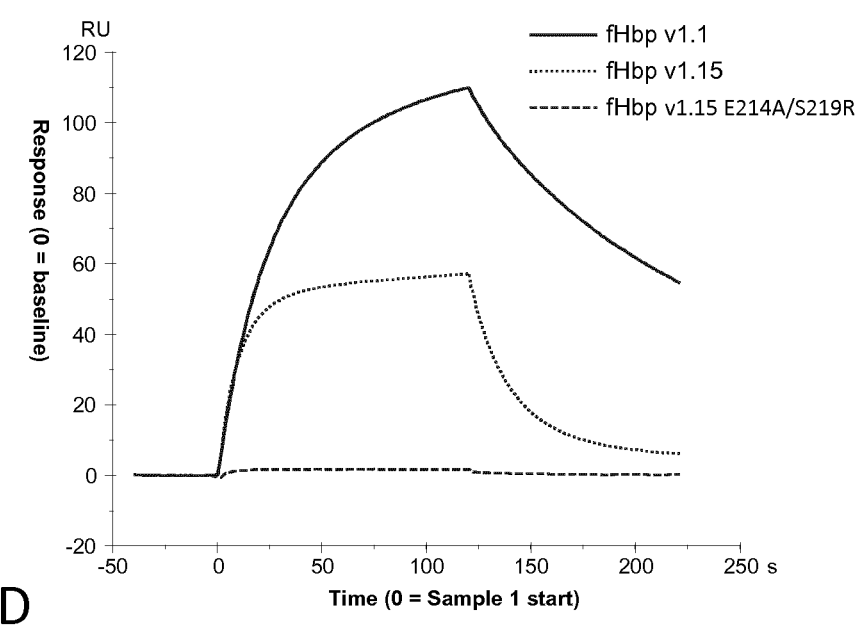

The data shown in FIG. 5 (A-D) compare the binding to factor H domain 6-7 of fHbp v1.1 and fHbp v1.15 (wildtype) with fHbp v.1.15 E214A (FIG. 5A), fHbp v1.15 S219R (FIG. 5B), fHbp v.1.15 E214A/E235A (FIG. 5C) and fHbp v.1.15 E214A/S219R (FIG. 5D).

While the fHbp v1.15 single mutants show reduced fH binding compared with v.1.1 and wildtype v1.15 (see FIGS. 5A and 5B), the double mutants v1.15 E214A/E235A and v1.15 E214A/S219R show no significant binding to the factor H subdomain fH6-7 (see FIGS. 5C and 5D).

Figure 6:
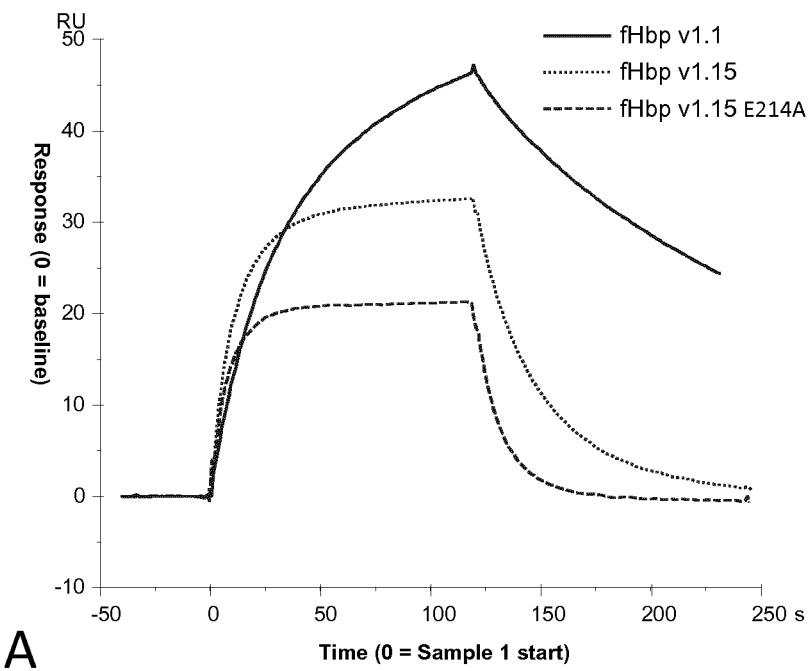
Figure 6:
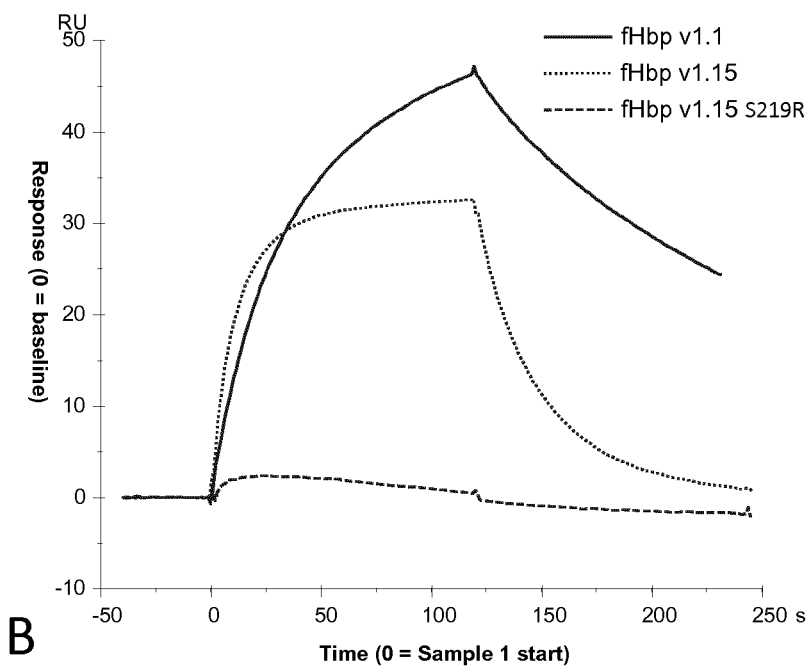
Figure 6:
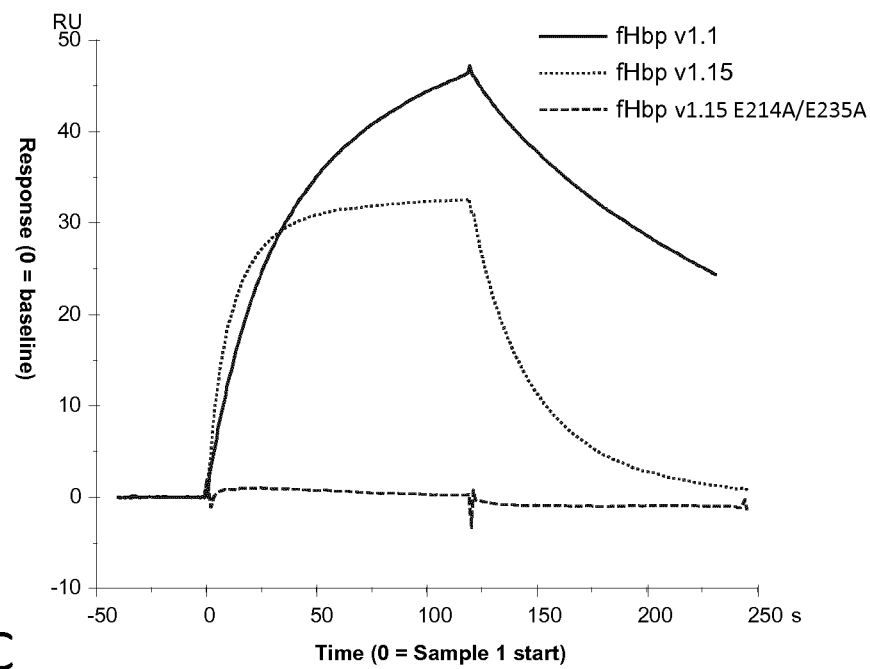
Figure 6:
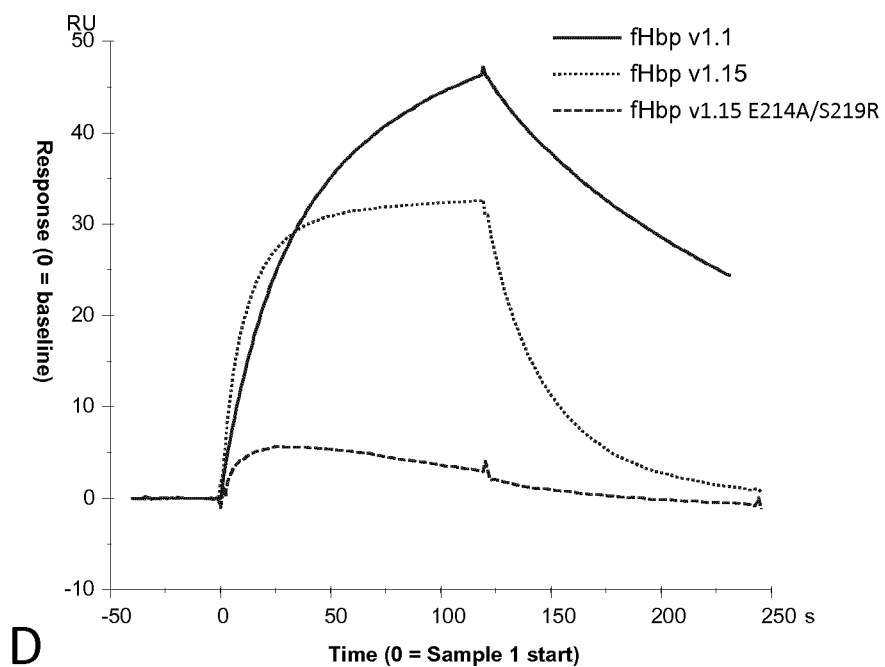

The data shown in FIG. 6 (A-D) compare the binding to the full-length factor H protein of fHbp v1.1 and fHbp v1.15 (wildtype) with fHbp v.1.15 E214A (FIG. 6A), fHbp v1.15 S219R (FIG. 6B), fHbp v.1.15 E214A/E235A (FIG. 6C) and fHbp v.1.15 E214A/S219R (FIG. 6D).

While the fHbp v1.15 single mutant E214A shows reduced fH binding compared with v.1.1 and wildtype v1.15 (see FIG. 6A), the single mutant v1.15 S219R and double mutant v1.15 E214A/E235A do not bind significantly to the full length fH protein (see FIGS. 6B and C).

The double mutant v1.15 E214A/S219R appears to show some residual binding activity to the full length fH protein (see FIG. 6D).

Therefore, in summary, the most promising candidates for reducing or abolishing hfH binding are fHbp mutants v1.13 E211A/E232A, v1.13 E211A/S216R, v1.15 S219R and v1.15 E214A/E235A.

Example 3: Binding of fHbp 23(S)1.13 and 23(S)1.15 Fusion Mutants to hfH

The following fusion polypeptides (Table 2) were generated (with the addition of a C-terminal His$_6$ tag where not already indicated as part of the referenced sequence) in order to investigate the effect of mutating the var component of fHbp 231 fusion proteins on the ability of the fusion to bind to human factor H (hfH):

TABLE 2

| Protein | SEQ ID # | N. purification | Purity % (SE_UPLC) |
|---|---|---|---|
| fHbp 231wt | 29 | MENB593 | 85 |
| fHbp 231S | 30 | MENB665 | 92 |
| fHbp 23S_1.13_E211A/S216R | 19 | MENB689 | 93 |
| fHbp-23S_1.15 E214A/E235A | 22 | MENB702 | 91 |
| fHbp-23S_1.13_E211A/E232A | 18 | MENB703 | 90 |

The inventors investigated the binding of fHbp 23(S)1.13 and 23(S)1.15 fusion mutants to hfH using SPR, as described above in relation to Example 2.

The fHbp 231S fusion (SEQ ID NO: 30) used in this example includes variant 2 and variant 3 sequences comprising the S32V/L123R and S32V/L126R stabilising mutations respectively, as described in detail above. Specifically, the v2 component of the 213S fusion has the sequence of SEQ ID NO: 16 and the v3 component of the 213S fusion has the sequence of SEQ ID NO: 17. The v1.1 component of the fHbp 231S fusion includes an fH non-binding point mutation (R→S), as shown in bold in SEQ ID NO: 30 above and corresponds to the R41S mutation described in WO2011/126863.

The fHbp 231 wt fusion (SEQ ID NO: 29) used in this example corresponds to the fusion of SEQ ID NO: 30, but without the introduction of the stabilising mutations in v2 and v3, and without the non-binding mutation in v1.1.

The fHbp 23S_1.13E211A/S216R fusion (SEQ ID NO: 19) corresponds to the fusion of SEQ ID NO: 30, but the v1 component of the fusion is the v1.13 non-binding E211A/S216R mutant of the present invention.

The fHbp 23S_1.15 E214A/E235A fusion (SEQ ID NO: 22) corresponds to the fusion of SEQ ID NO: 30, but the v1 component of the fusion is the v1.15 non-binding E214A/E235A mutant of the present invention.

The fHbp-23S_1.13E211A/E232A fusion (SEQ ID NO: 18) corresponds to the fusion of SEQ ID NO: 30, but the v1 component of the fusion is the v1.13 non-binding E211A/S216R mutant of the present invention.

The fHbp 231 wt (SEQ ID NO: 29) and fHbp 231S (SEQ ID NO: 30) fusion proteins function as controls in this experiment.

Figure 7:
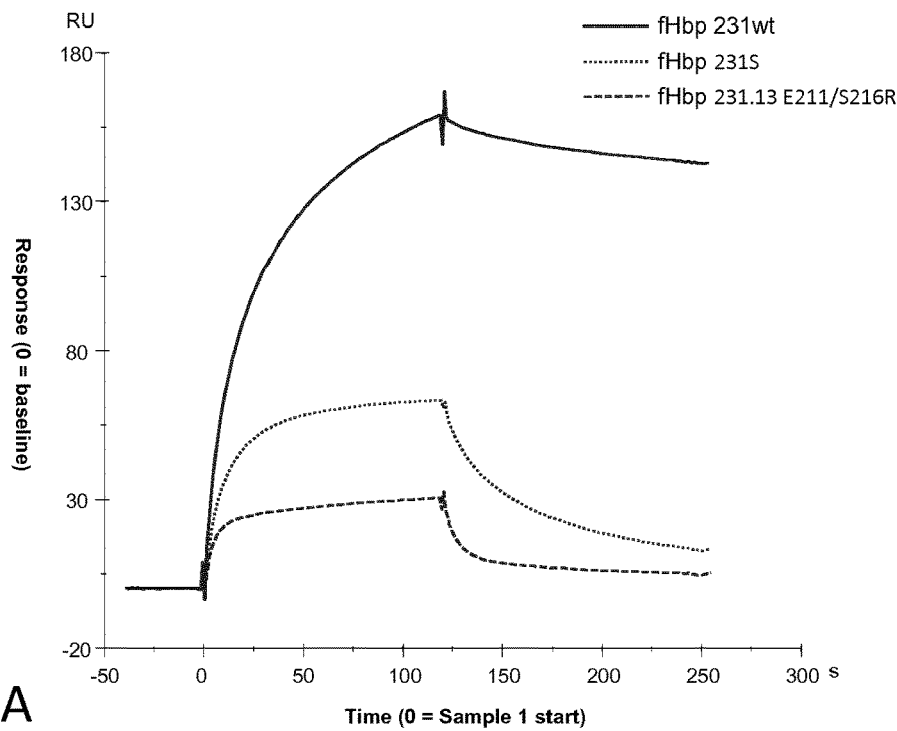
Figure 7:
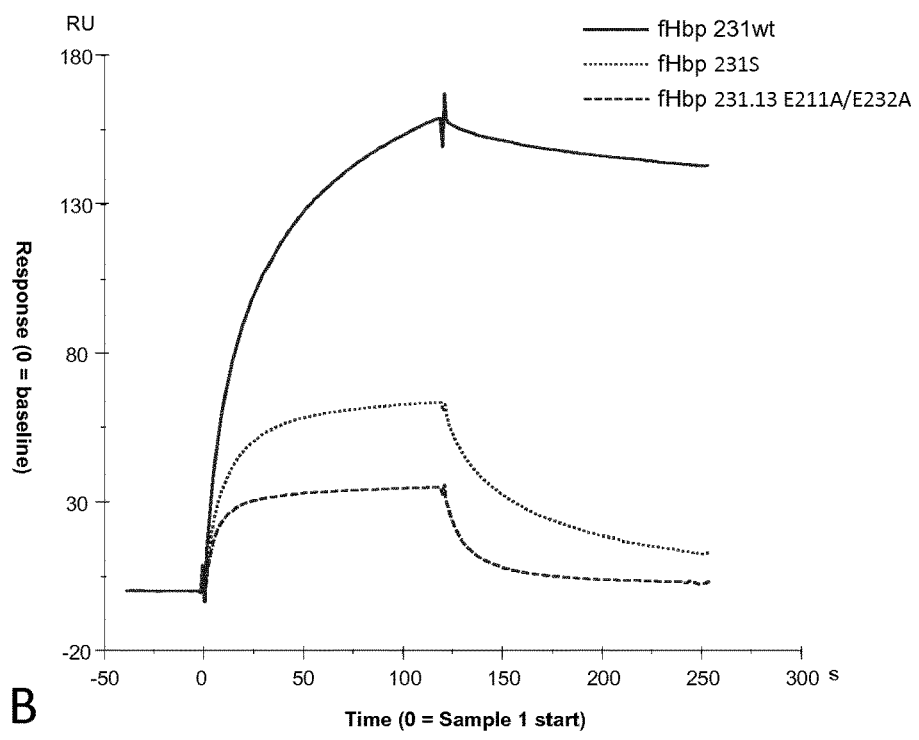

The sensograms shown in FIG. 7 (A-B) compares the binding to factor H (hfH) domain 6-7 of fHbp 231 wt fHbp 231S with fHbp 23S_1.13E211A/S216R (FIG. 7A), and fHbp 23S_1.13E211A/E232A (FIG. 7B).

Figure 8:
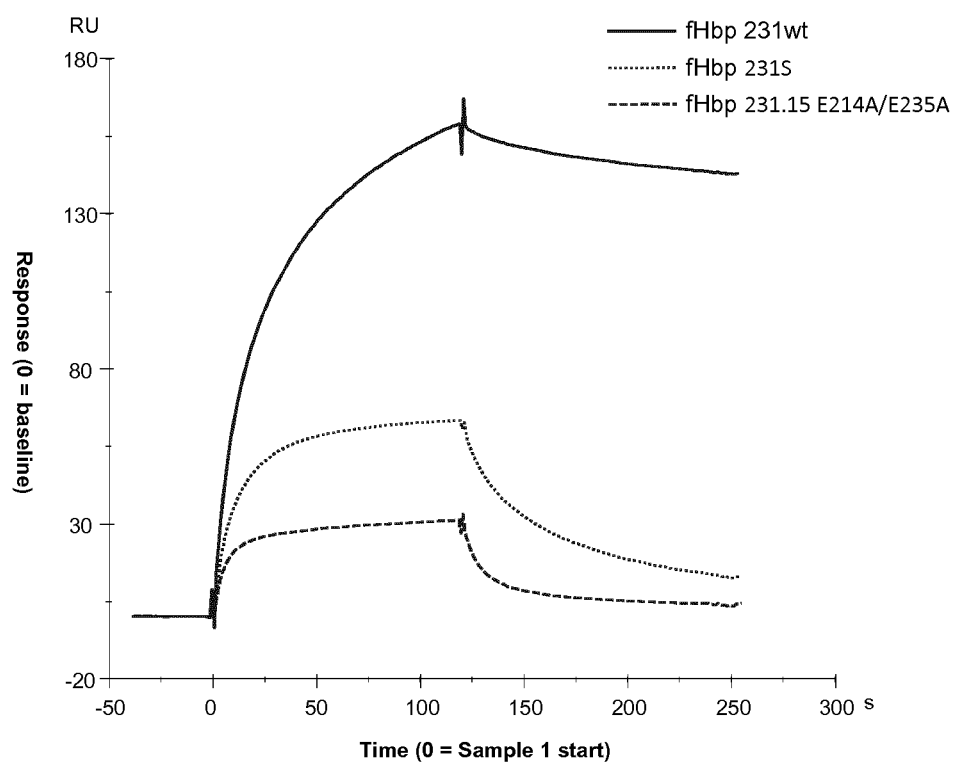

The sensogram shown in FIG. 8 compares the binding to factor H (hfH) domain 6-7 of fHbp 231 wt fHbp 231S with fHbp 23S_1.15 E214A/E235A A fragment of hfH containing only domains 6-7 has been shown to be sufficient to mimic the fHbp-hfH interaction (Schneider et al. (2009) Nature 458:890-893), thus providing a simplified model system to assess the affinity of fHbp mutants and constructs to hfH.

It is clear from FIGS. 7 and 8 that all three of the v1.13/1.15 mutants display strongly reduced binding activity to the factor H domain 6-7. With respect to the 2fHbp 31S fusion, binding activity shown by the v1.13 and v1.15 mutant fusions is clearly reduced.

Figure 9:
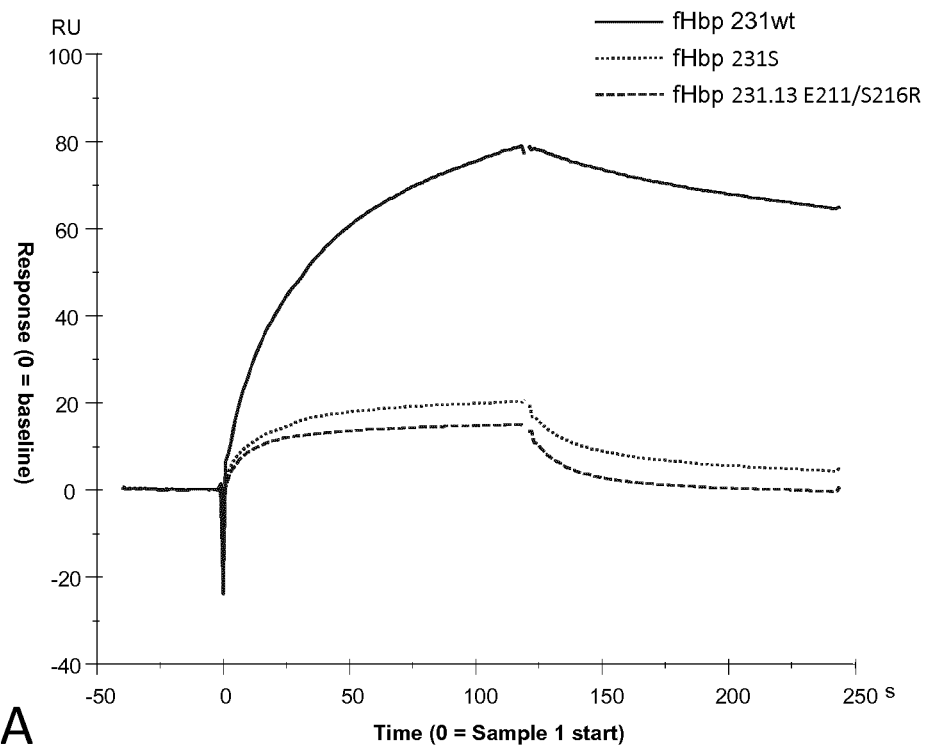
Figure 9:
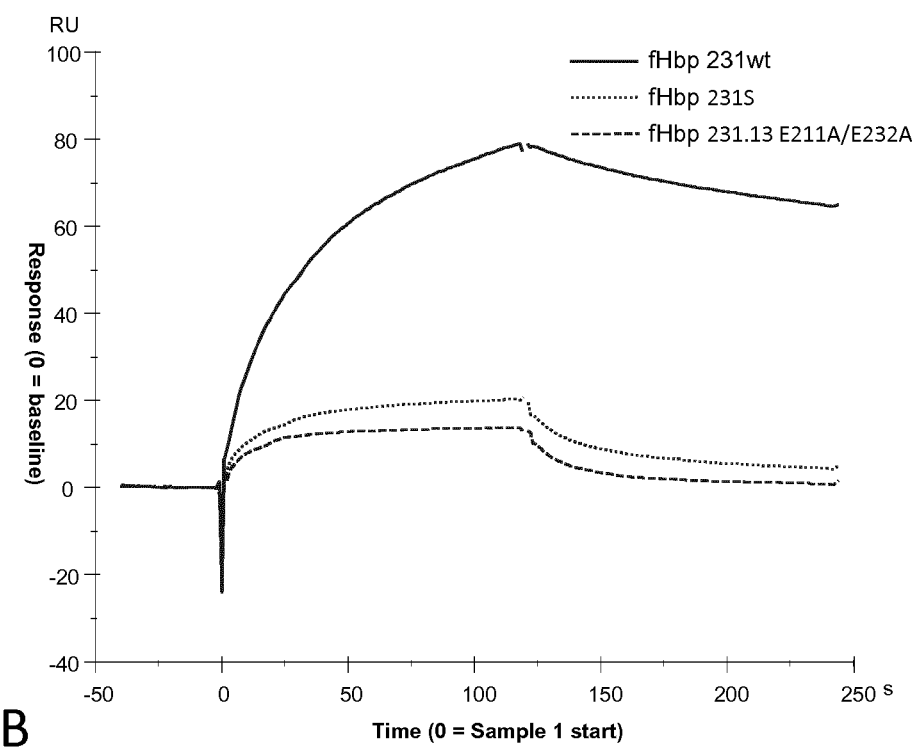

The sensograms shown in FIG. 9 (A-B) compare the binding to the full-length factor H protein of fHbp 231 wt fHbp 231S with fHbp 23S_1.13E211A/S216R (FIG. 9A), and fHbp 23S_1.13E211A/E232A (FIG. 9B).

Figure 10:
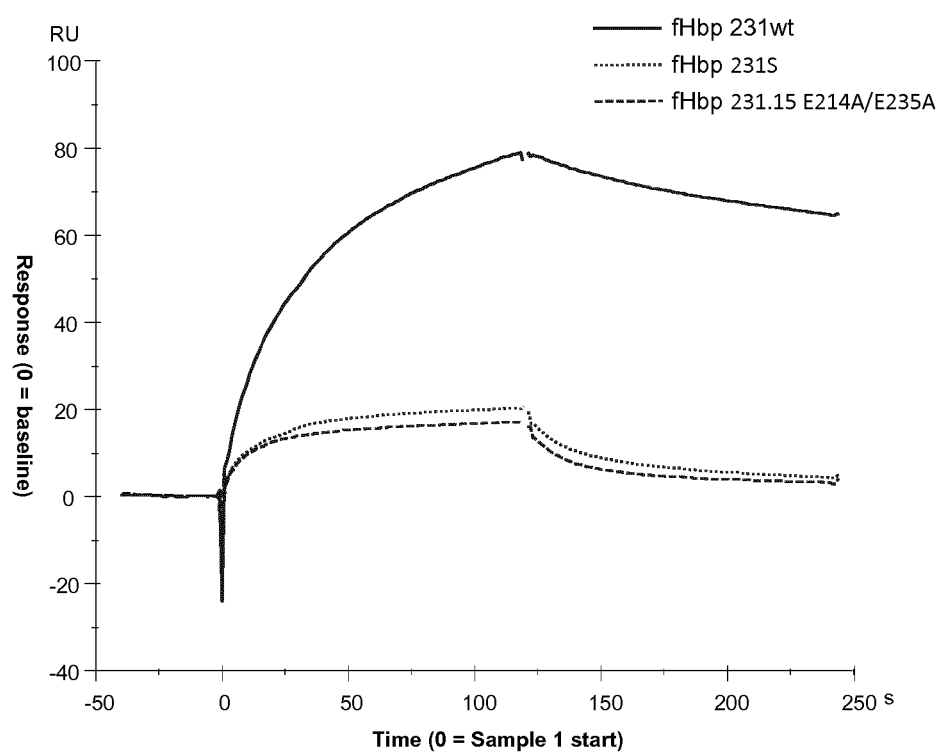

The sensogram shown in FIG. 10 compares the binding to the full-length factor H protein of fHbp 231 wt and fHbp 231S with fHbp 23S_1.15 E214A/E235A.

These data show that all three of the v1.13/1.15 mutants tested display strongly reduced binding activity to the full-length factor H, comparable to the fHbp 231S fusion.

Example 4: Investigating the Immunogenicity Elicited by fHbp Fusion Proteins According to the Invention Against Meningococcal Strains Expressing a Variety of Different fHbp v1 Subvariants (v1.x)

Primary Objective:

To investigate the immunogenicity elicited by 231.13 fusion proteins comprising mutations that reduce or abrogate hfH binding against meningococcal strains expressing fHbp in a variety of different fHbp v1 subvariants, compared with existing fHbp antigens/fusion proteins, and the licensed 4CMenB vaccine. Immunogenicity is determined using rabbit Serum Bactericidal Assay (rSBA) and human Serum Bactericidal Assay (hSBA) against the following fHbp v1 subvariant (v1.x) strains: v1.1, v1.10, v1.13, v1.14 and v1.15.

These experiments aim to evaluate whether fHbp fusion proteins according to the present invention show comparable immunogenicity (non-inferiority) against a panel of strains expressing fHbp v1.x, compared with existing antigen/fusion compositions, and the licensed 4CMenB vaccine.

Immunization Protocol:

Seven groups of 10 mice (CD1 females, aged 6-8 weeks) received three separate 200 µl doses of one of seven different antigen compositions, as detailed in Table 3 below.

Mice were immunized interaperitoneally (i.p.) at days 1, 22 and 36.

Mice were bled at days 0, 35 and 50.

TABLE 3

| | | Treatment | | |
|---|---|---|---|---|
| Group | Number of animals | Antigen | Antigen dose | Adjuvant dose | Volume and route of injection |
| 1 | 10 | 231.13_E211A/ S216R (SEQ ID NO: 19) | 20 µg antigen | Al(OH)$_3$ 3 mg/ml | 200 µl IP |
| 2 | 10 | 231.13_E211A/ E211A/E232A (SEQ ID NO: 18) | 20 µg antigen | Al(OH)$_3$ 3 mg/ml | 200 µl IP |
| 3 | 10 | 231.13 (SEQ ID NO:29) | 20 µg antigen | Al(OH)$_3$ 3 mg/ml | 200 µl IP |
| 4 | 10 | 231.1S (SEQ ID NO:30) | 20 µg antigen | Al(OH)$_3$ 3 mg/ml | 200 µl IP |
| 5 | 10 | fHbp v1.1 (SEQ ID NO: 33) | 20 µg antigen | Al(OH)$_3$ 3 mg/ml | 200 µl IP |

TABLE 3-continued

| Group | Number of animals | Antigen | Antigen dose | Adjuvant dose | Volume and route of injection |
|---|---|---|---|---|---|
| 6 | 10 | 936-741* | 20 µg antigen | Al(OH)$_3$ 3 mg/ml | 200 µl IP |
| 7 | 10 | BEXSERO-like** | 20 µg antigen + 10 µg OMV | Al(OH)$_3$ 3 mg/ml | 200 µl IP |

*936-741 is the GNA2091-fHbp fusion included in the 4CMenB vaccine
**BEXSERO-like refers to the complete BEXSERO product, but not necessarily from a batch approved for release.

End-Point:
Total IgG elicited against fHbp two weeks after the third immunization.
rSBA and hSBA analysis of pooled sera against a panel of *Neisseria meningitidis* strains expressing fHbp v1.1, v1.10, v1.13, v1.14 and v1.15.

Figure 11:
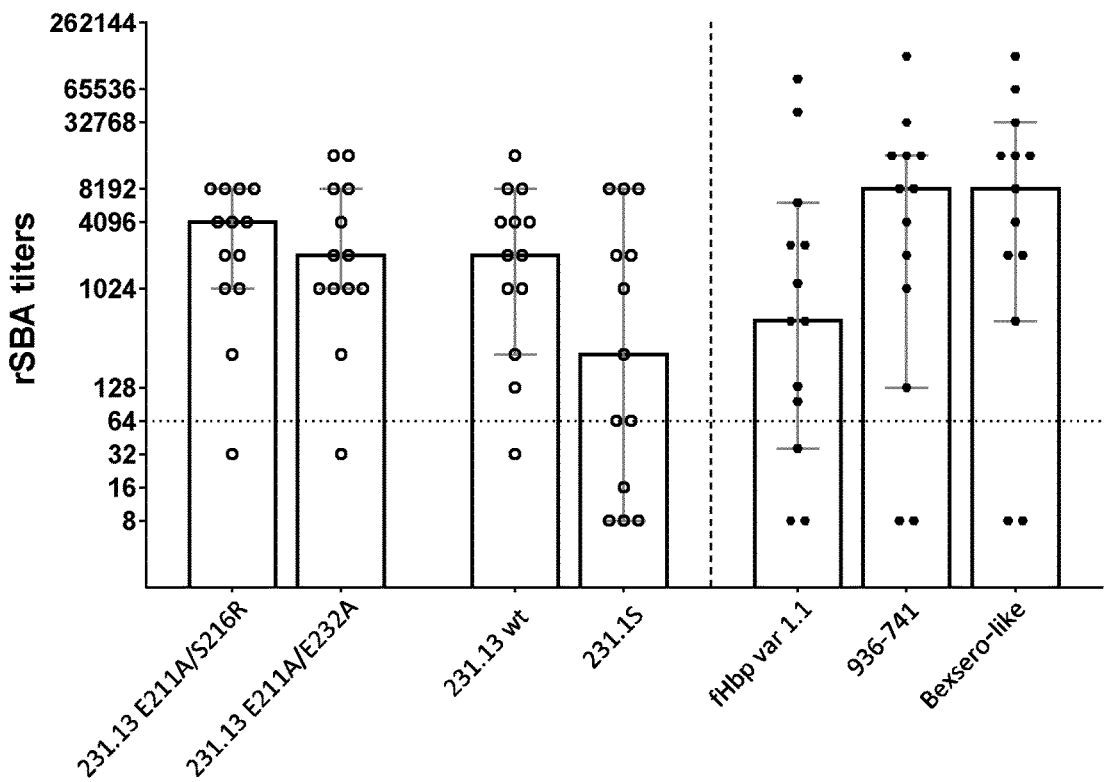
Figure 11:
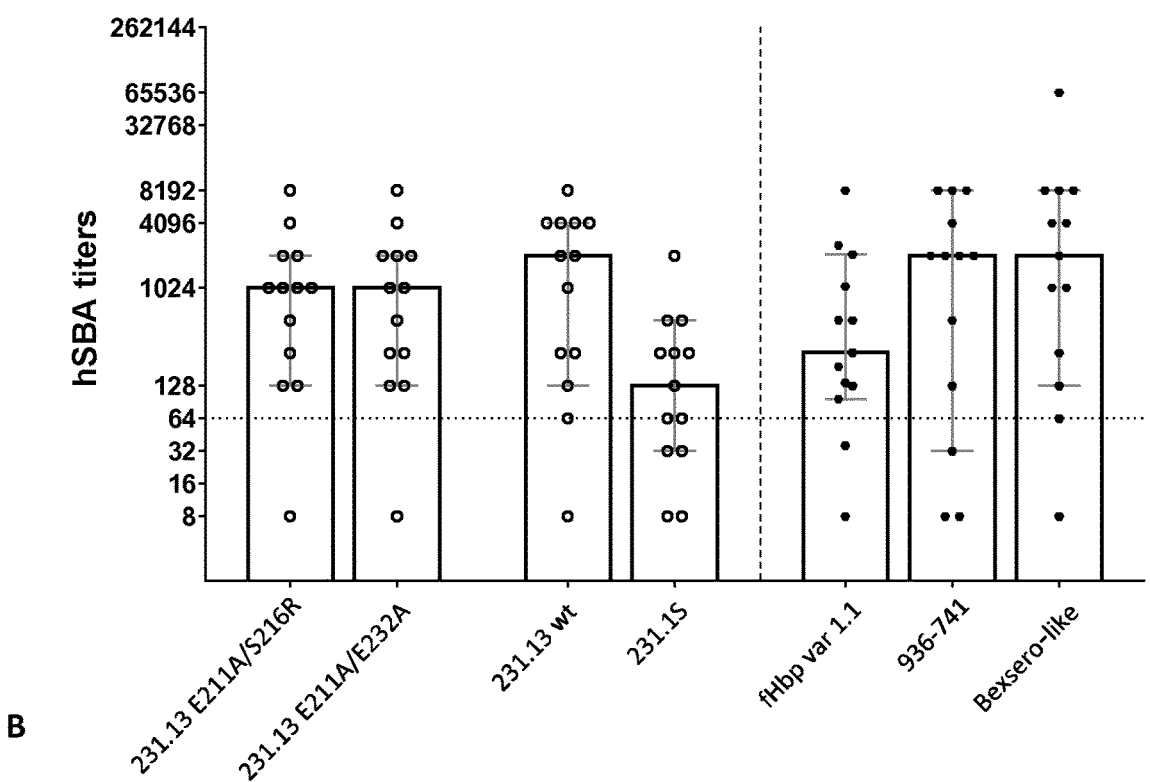

Results:
FIG. 11A shows rSBA titres (rabbit complement) for each of the 7 antigen compositions tested against a variety of meningococcal strains expressing fHbp in v1.x. In the SBA results each dot represents SBA titre of single strains analysed on pooled sera. FIG. 11B shows hSBA titres (human complement) for each of the 7 antigen compositions tested against the same variety of strains expressing fHbp in v1.x.

The results show that fHbp fusion proteins according to the invention (Groups 1 and 2) show comparable (non-inferior) immunogenicity to the licensed BEXSERO product and the BEXSERO fHbp antigen (936-741) against a panel of v1.x strains.

Interestingly, these results also indicate that fHbp fusion proteins according to the invention (Groups 1 and 2) are more immunogenic than existing fusion proteins known in the art (specifically the 231.1S fusion (herein SEQ ID NO: 30)), against a patent of v1.x strains, as determined in both rSBA and hSBA.

Example 5: Investigating the Immunogenicity Elicited by fHbp Fusion Proteins According to the Invention Against Meningococcal Strains Expressing fHbp v2/v3

Primary Objective:
To investigate the immunogenicity elicited by 231.13 fusion proteins comprising mutations that reduce or abrogate hfH binding against meningococcal strains expressing fHbp in v2 or v3, compared with existing fHbp antigens/fusions proteins, and the licensed 4CMenB vaccine. These experiments aim to evaluate whether the inclusion of three different mutated fHbp variants has the potential to increase the breadth of strain coverage, compared to existing antigen compositions.

Immunogenicity is determined using rabbit Serum Bactericidal Assay (rSBA) and human Serum Bactericidal Assay (hSBA) against the following fHbp v2 and v3 strains: v2.16, v3.31 and v3.42.

Immunization Protocol:
Seven groups of 10 mice (CD1 females, aged 6-8 weeks) received three separate 200 µl doses of one of seven different antigen compositions, as detailed in Table 4 below.
Mice were immunized interaperitoneally (i.p.) at days 1, 22 and 36.
Mice were bled at days 0, 35 and 50.

TABLE 4

| Group | Number of animals | Antigen | Antigen dose | Adjuvant dose | Volume and route of injection |
|---|---|---|---|---|---|
| 1 | 10 | 231.13_E211A/S216R (SEQ ID NO: 19) | 20 µg antigen | Al(OH)$_3$ 3 mg/ml | 200 µl IP |
| 2 | 10 | 231.13_E211A/E211A/E232A (SEQ ID NO: 18) | 20 µg antigen | Al(OH)$_3$ 3 mg/ml | 200 µl IP |
| 3 | 10 | 231.13 (SEQ ID NO:29) | 20 µg antigen | Al(OH)$_3$ 3 mg/ml | 200 µl IP |
| 4 | 10 | 231.1S (SEQ ID NO:30) | 20 µg antigen | Al(OH)$_3$ 3 mg/ml | 200 µl IP |
| 5 | 10 | fHbp v1.1 (SEQ ID NO: 33) | 20 µg antigen | Al(OH)$_3$ 3 mg/ml | 200 µl IP |
| 6 | 10 | 936-741* | 20 µg antigen | Al(OH)$_3$ 3 mg/ml | 200 µl IP |
| 7 | 10 | BEXSERO-like** | 20 µg antigen + 10 µg OMV | Al(OH)$_3$ 3 mg/ml | 200 µl IP |

*936-741 is the GNA2091-fHbp fusion included in the 4CMenB vaccine
**BEXSERO-like refers to the complete BEXSERO product, but not necessary from a batch approved for release.

End-Point:
Total IgG elicited against fHbp two weeks after the third immunization.
rSBA and hSBA analysis of pooled sera against a panel of *Neisseria meningitidis* strains expressing fHbp in variant 2 or variant 3.

Figure 12:
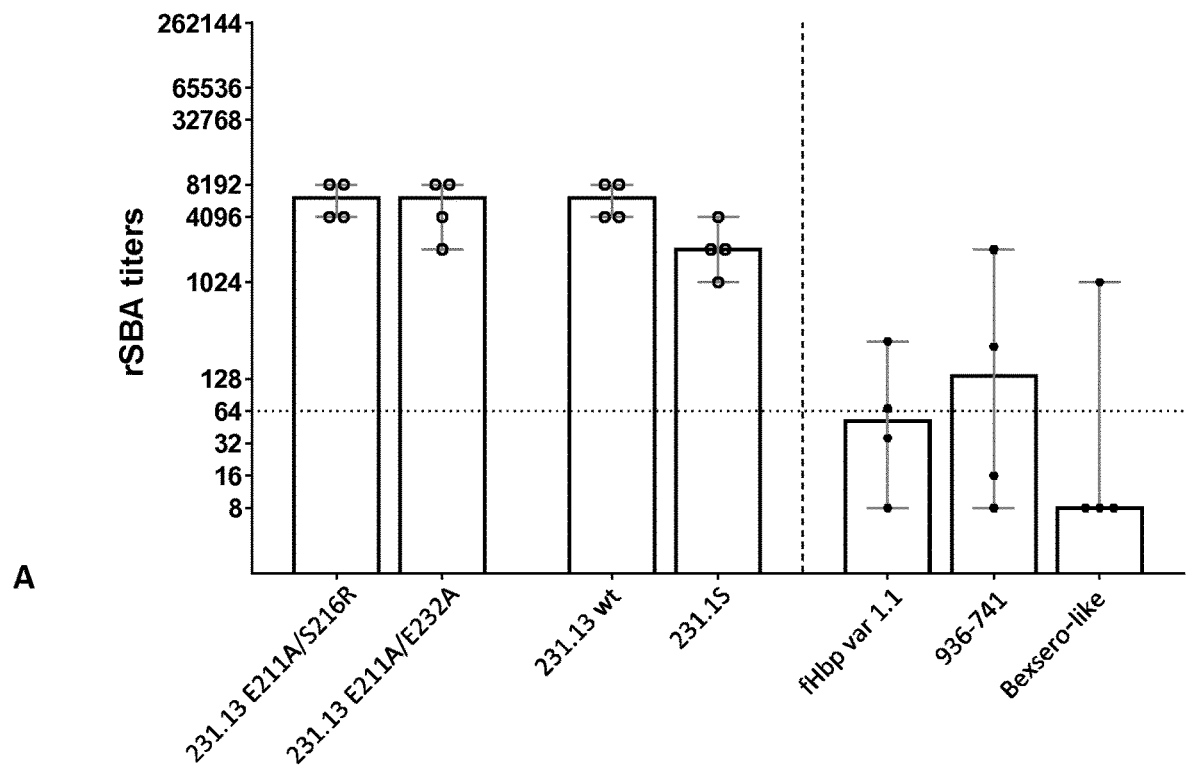
Figure 12:
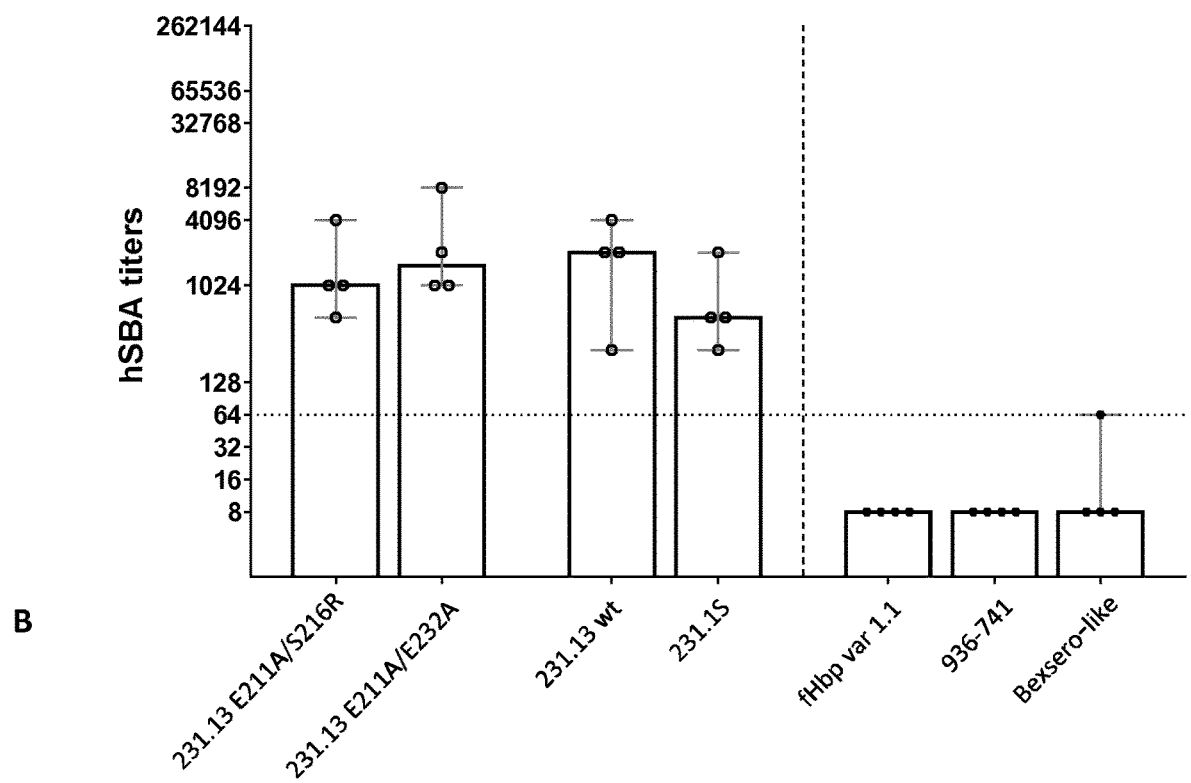

Results:
FIG. 12A shows rSBA titres for each of the 7 antigen compositions tested against a variety of meningococcal strains expressing fHbp in v2 or v3. In the SBA results each dot represents SBA titre of single strains analysed on pooled sera. FIG. 12B shows hSBA titres for each of the 7 antigen compositions tested against the same variety of strains expressing fHbp in v2 or v3.

The results show that fusion proteins comprising all three fHbp variants generate much higher titres in rSBA and hSBA compared with fHbp v1.1 alone, the 936-741 fusion included in BEXSERO or indeed the BEXSERO product itself. This is evidence of a significantly improved immunological response against strains expressing fHbp in v2 or v3, compared with the existing vaccine or vaccine components.

Example 6: Assessing the Added Value of Inclusion of fHbp231.x Non-Binding Mutants of the Invention in the Current 4CMenB Vaccine Primary Objective:
a) To evaluate the strain coverage (defined as hSBA titers ≥64) of 4CMenB+the fHbp231.13_E211A/S216R fusion protein of the invention compared to the current 4CMenB vaccine at two weeks after the third dose in two different animal models (mice and rabbit), as measured by hSBA titers against 20 fHbp var 2 and 3 strains of selected serogroup B *Neisseria meningitidis*.
b) To evaluate the strain coverage (defined as hSBA titers ≥64) of 4CMenB+the fHbp231.13_E211A/S216R fusion protein of the invention compared to the current 4CMenB vaccine at two weeks after the third dose in two different animal models (mice and rabbit), as measured by hSBA titers against 30 fHbp var 1.x strains of selected serogroup B *Neisseria meningitidis*.

c) To evaluate the strain coverage (to assess non-inferiority) of 4CMenB+the fHbp231.13_E211A/S216R fusion protein of the invention compared to the current 4CMenB vaccine at two weeks after the third dose in two different animal models (mice and rabbit), as measured by hSBA titers against 11 serogroup B *Neisseria meningitidis* including 4CMenB reference strains and strains carrying fHbp var 1.1 and 1.4 predicted covered by 4CMenB.

Endpoint: hSBA titers from pooled sera (one pool per group) collected at two weeks after the third injection.

Study Design in Mouse

CD1 female mice of 4-6 weeks old strain received three injections intraperitoneally (IP) with 200 µl of 4CMenB adsorbed Aluminium Hydroxide (BEXSERO) or 4CMenB-adsorbed Aluminium Hydroxide (BEXSERO) plus various different fHbp 231 fusions protein (as shown in Table 5 below) at day 1, 22 and 36. Blood samples collected before 1$^{st}$ injection (day 0) and final bleed collected two weeks after the third injection (day 49).

TABLE 5

| | | | Treatment | | | | Sample |
|---|---|---|---|---|---|---|---|
| Group | Number of animals | Vaccine | Antigen dose | Adjuvant dose | Volume and route of injection | Immunization schedule (Days) | collection (organs, blood volume) and days |
| 1 | 10 | 4CMenB | 20 µg protein +10 µg OMV | Al(OH)3 3 mg/ml | 200 µl IP | 1, 22, 36 | Blood at day 0, 49 |
| 2 | 10 | 4CMenB + fHbp 231.13_wt | 20 µg protein +10 µg OMV | Al(OH)3 3 mg/ml | 200 µl IP | 1, 22, 36 | Blood at day 0, 49 |
| 3 | 10 | 4CMenB + fHbp 231.13_E211A/ S16R | 20 µg protein+10 µg OMV | Al(OH)3 3 mg/ml | 200 µl IP | 1, 22, 36 | Blood at day 0, 49 |
| 4 | 10 | 4CMenB + fHbp 231.13_E211A/ E232A | 20 µg protein +10 µg OMV | Al(OH)3 3 mg/ml | 200 µl IP | 1, 22, 36 | Blood at day 0, 49 |
| 5 | 10 | 4CMenB + fHbp 231S* | 20 µg protein +10 µg OMV | Al(OH)3 3 mg/ml | 200 µl IP | 1, 22, 36 | Blood at day 0, 49 |
| 6 | 10 | 4CMenB + fHbp 231.15_wt | 20 µg protein +10 µg OMV | Al(OH)3 3 mg/ml | 200 µl IP | 1, 22, 36 | Blood at day 0, 49 |
| 7 | 10 | 4CMenB + fHbp 231.15_E214A/ E235A | 20 µg protein +10 µg OMV | Al(OH)3 3 mg/ml | 200 µl IP | 1, 22, 36 | Blood at day 0, 49 |
| 8 | 10 | 4CMenB + fHbp 231S* | 20 µg protein + 10 µg OMV | Al(OH)3 3 mg/ml | 200 µl IP | 1, 22, 36 | Blood at day 0, 49 |

*The fHbp 231S fusion protein includes stabilising mutations in the v2 and v3 components, in addition to an fH non-binding point mutation (R→S) in the v1.1 component, as shown in bold in SEQ ID NO: 30 herein, which corresponds to the R41S mutation described in WO2011/126863.

Study Design in Rabbit

New Zealand female rabbits of 9 weeks old received three injections intramuscular (IM) of 500 µl of 4CMenB adsorbed in Aluminium Hydroxide (BEXSERO) or 4CMenB-adsorbed Aluminium Hydroxide (BEXSERO) plus various different fHbp 231 fusion proteins (as shown in Table 6 below) at days 1, 21 and 35. Final bleed collected two weeks after the third injection.

TABLE 6

| | | | Treatment | | | | Sample |
|---|---|---|---|---|---|---|---|
| Group | Number of animals | Vaccine | Antigen dose | Adjuvant dose | Volume and route of injection | Immunization schedule (Days) | collection (organs, blood volume) and days |
| 1 | 3 | 4CMenB | 50 + 100 µg protein + 25 µg OMV | Al(OH)3 3 mg/ml | 500 µl IM | 1, 22, 36 | Blood at day 0, 49 |
| 2 | 3 | 4CMenB + fHbp 231.13_wt | 50 + 100 µg protein + 25 µg OMV | Al(OH)3 3 mg/ml | 500 µl IM | 1, 22, 36 | Blood at day 0, 49 |
| 3 | 3 | 4CMenB + fHbp 231.13_E211A/ S216R | 50 + 100 µg protein + 25 µg OMV | Al(OH)3 3 mg/ml | 500 µl IM | 1, 22, 36 | Blood at day 0, 49 |

TABLE 6-continued

| Group | Number of animals | Vaccine | Antigen dose | Adjuvant dose | Volume and route of injection | Immunization schedule (Days) | Sample collection (organs, blood volume) and days |
|---|---|---|---|---|---|---|---|
| 4 | 3 | 4CMenB + fHbp 231.15_wt | 50 + 100 µg protein + 25 µg OMV | Al(OH)3 3 mg/ml | 500 µl IM | 1, 22, 36 | Blood at day 0, 49 |
| 5 | 3 | 4CMenB + fHbp 231S* | 50 + 100 µg protein + 25 µg OMV | Al(OH)3 3 mg/ml | 500 µl IM | 1, 22, 36 | Blood at day 0, 49 |
| 6 | 3 | 4CMenB + fHbp 231.15_ E214A/ E235A | 50 + 100 µg protein + 25 µg OMV | Al(OH)3 3 mg/ml | 500 µl IM | 1, 22, 36 | Blood at day 0, 49 |

*The fHbp 231S fusion protein includes stabilising mutations in the v2 and v3 components, in addition to an fH non-binding point mutation (R→S) in the v1.1 component, as shown in bold in SEQ ID NO: 30 herein, which corresponds to the R41S mutation described in WO2011/126863.

Sample Size Justification

Ten mice and 3 rabbits per group is the minimum number of animals that will allow enough pooled serum to be tested in hSBA against a large panel of strains (about 73), considering 20% of retest or further titrations.

A total of 61 fHbp var 1, 2 and 3 carrying strains of selected serogroup B Neisseria meningitides were tested by hSBA.

Immunological Read-Out

Functional antibodies were measured by Serum Bactericidal Assay using human complement (hSBA) on 61 strains of N. meningitidis carrying fHbp var 1.x, var 2, or var 3 and a panel of reference BEXSERO antigen strains.

SBA is the only accepted correlate of protection for N. meningitidis in humans.

Results

Humoral Responses-Functional Antibodies Measured by rSBA

To measure functional antibodies elicited by different BEXSERO formulations able to trigger complement-mediated killing of N. meningitidis strains, sera collected two weeks after the third vaccination were tested as pool in serum bactericidal activity assay using human rabbit serum as complement source (hSBA) against a panel of about 60 N. meningitidis strains.

The total number of Neisseria strains selected were divided in three different strains panels fHbp var 2 and 3, fHbp var 1.x and BEXSERO references and fHbp var 1.1 and 1.4 strains.

50 strains were selected to show added value of the formulation comprising fHbp231.13_E211A/S216R fusion protein of the invention vs BEXSERO:
  20 strains carrying fHbp var2 or var3
    Selection was based on fHbp frequency distribution and included strains carrying fHbp v2.16, v2.19, v2.21, v2.24, v3.116, v3.31 and v3.42.
  30 strains carrying fHbp var1.x
    Selection was performed to address current BEXSERO gaps and to sample the whole genetic diversity of fHbp var1, and included strains carrying fHbp v1.1, v1.4, v1.13, v1.15, v1.14, v1.10, v1.260, v1.510, v1.90, v1.275, v1.697, v1.226, v1.110, v1.249, v1.108, v1.227 and v1.215.
11 strains were selected to show non-inferiority of the formulation comprising fHbp231.13_E211A/S216R fusion protein of the invention vs BEXSERO, including BEXSERO reference strains plus additional strains known to be covered by BEXSERO (including fHbp 1.1 and 1.4).

Immunogenicity Studies in Mouse

To measure added value of the formulations comprising fHbp fusion proteins of the invention vs BEXSERO, sera collected from vaccinated mice were tested as pool in the presence of human plasma as complement source (hSBA) against a total of 50 MenB strains, divided into var (30 strains) and var2/3 strains (20 strains). Of note, the 50 strains were selected in order not to be covered by BEXSERO and therefore are mismatched for all BEXSERO antigens. The results are reported in FIGS. 13A and 13B.

Figure 13:
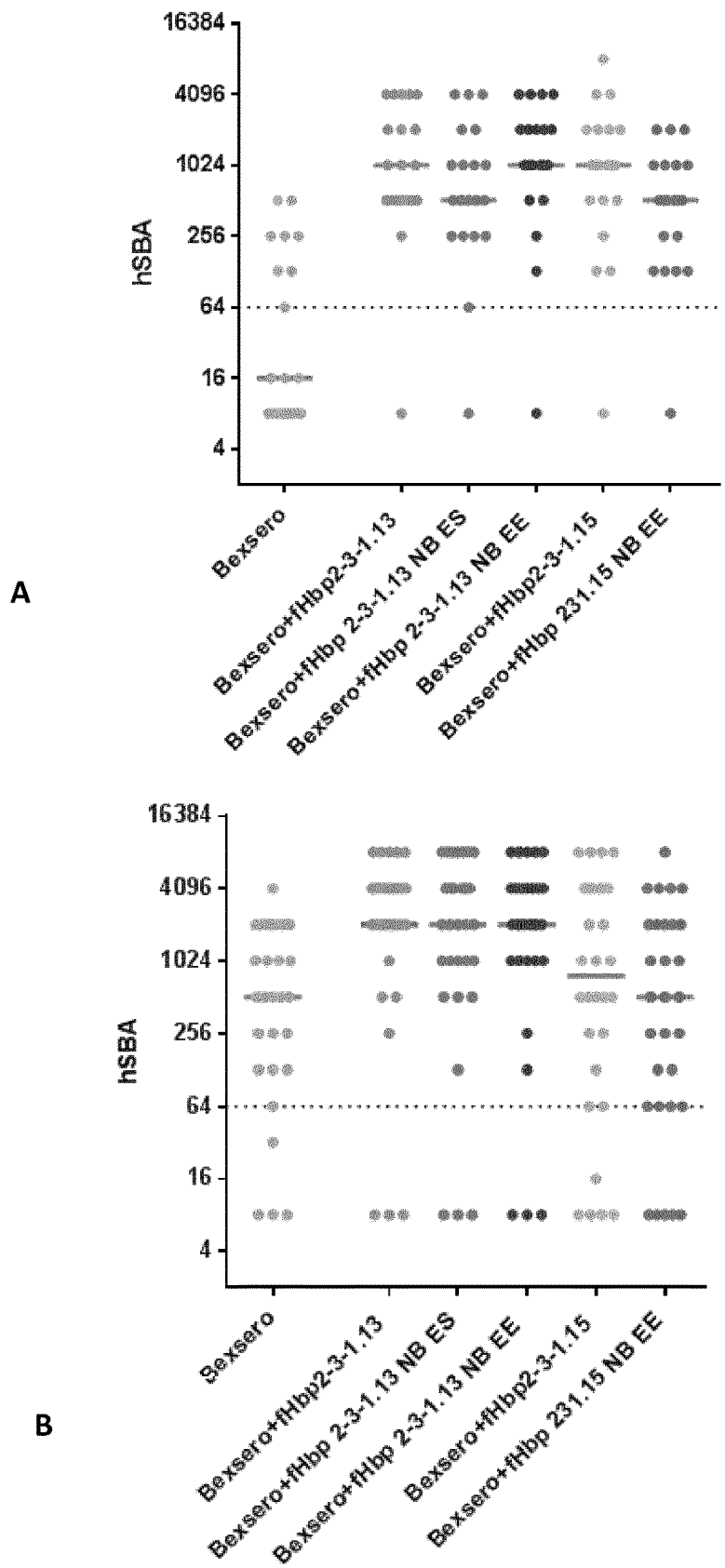

As it is evident from FIGS. 13A and 13B, the formulations comprising fHbp fusion proteins of the invention perform better than BESXERO against var 2/3 strains and are also superior to BEXSERO on var 1.x strain panel.

Figure 14:
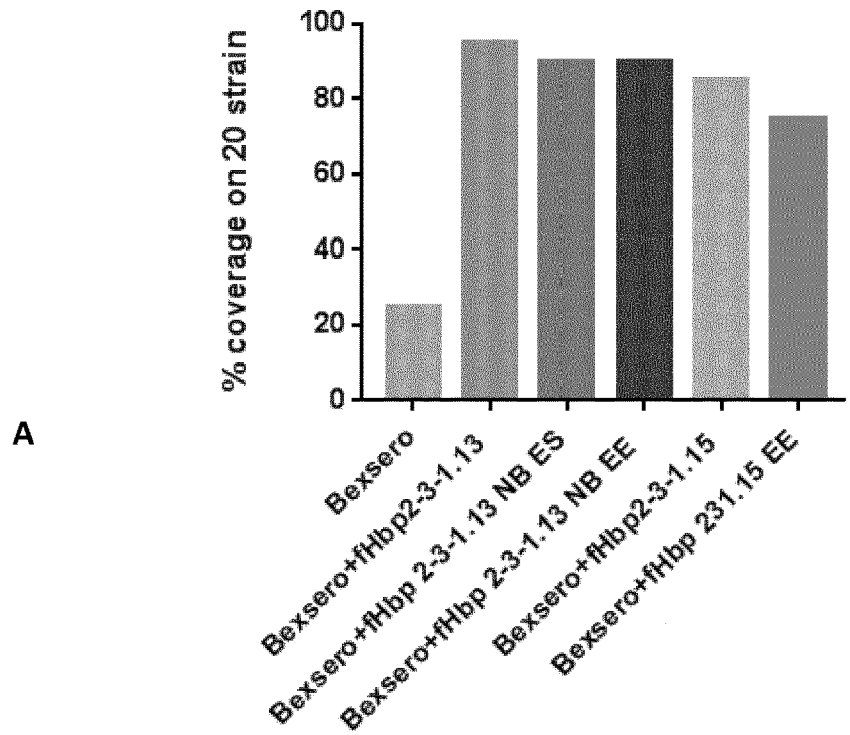
Figure 14:
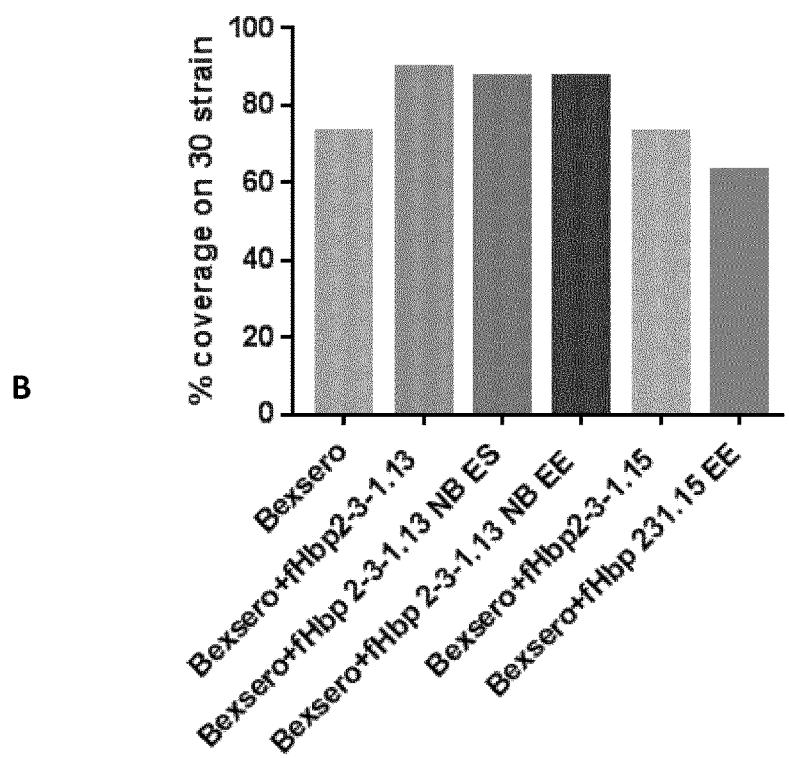

To help to distinguish between covered and non-covered strains a new threshold value of 256 (four times the initial threshold of 64) was selected. The percentages of covered strains were computed and are presented in FIGS. 14A and 14B.

The results shown in these graphs demonstrate again that formulations comprising fusion proteins of the invention present higher coverage against both var2 and 3 strain panels (FIG. 14A) compared to BEXSERO alone, and elicited higher coverage against the majority of variant 1.x strains (FIG. 14B) compared to BEXSERO.

Figure 15:
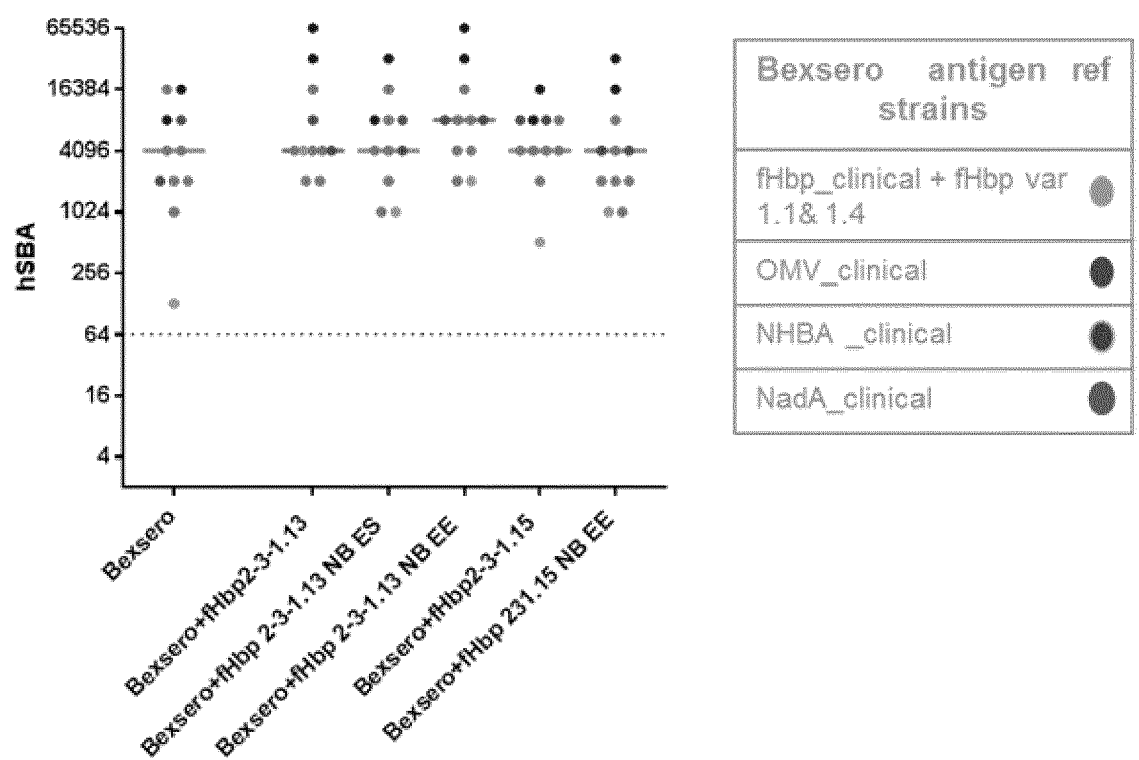

Finally, non-inferiority of formulations comprising fusion proteins of the invention was also assessed testing the mouse antisera against a panel of 11 strains including BEXSERO reference stains and fHbp var 1.1 and 1.4 strains in mouse (FIG. 15). Non-inferiority was assessed with pooled mouse sera tested in hSBA against the panel of 11 MenB strains.

The results shown in FIG. 15 indicate that not only was non-inferiority compared to BEXSERO confirmed for all formulations comprising fusion proteins of the invention, but also improved immunogenicity was evident for most of the strains, as a result of the additional contribution of antibodies directed against the additional fHbp components.

Figure 16:
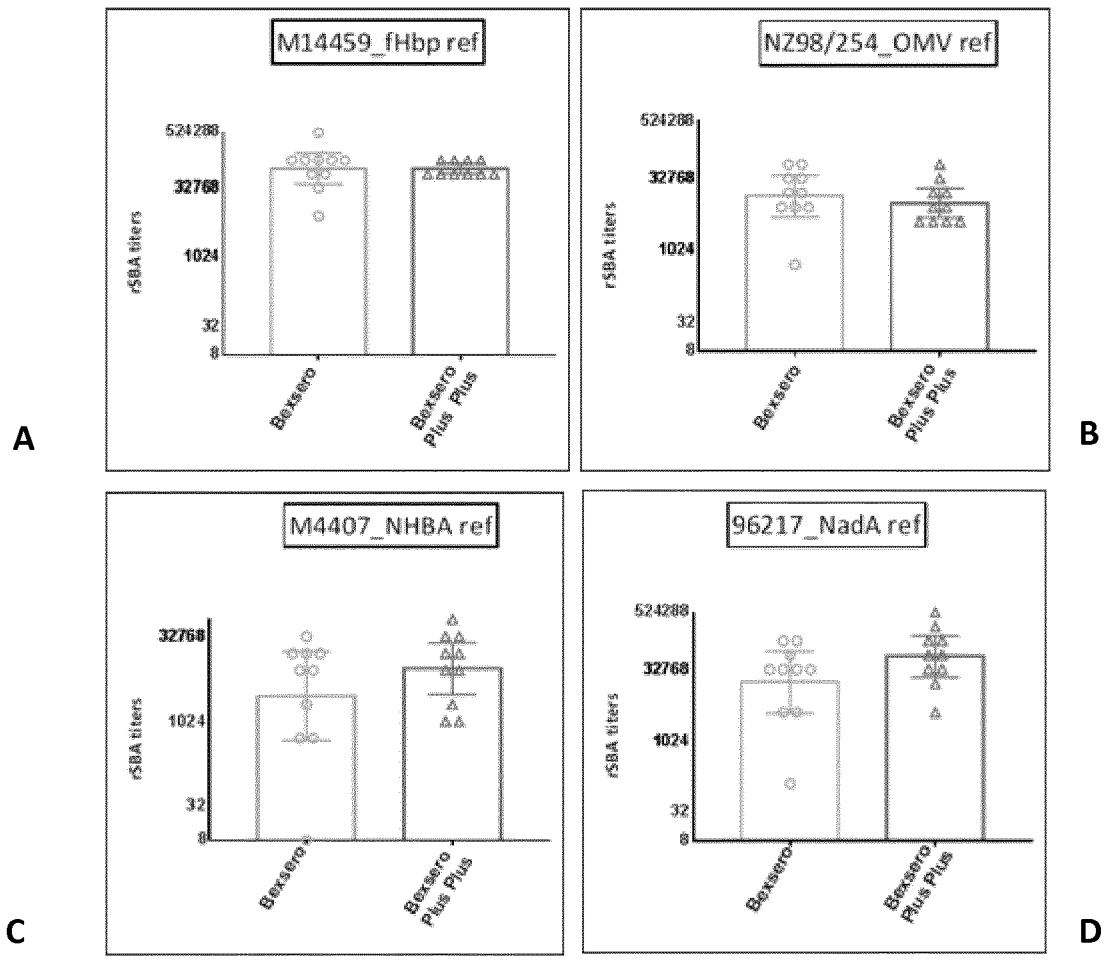

Non-inferiority of formulations comprising the fHbp231.13_E211A/S216R fusion protein of the invention versus BEXSERO has also been assessed by testing individual mouse sera with baby rabbit complement as complement source (rSBA) against the panel of the 4 BEXSERO indicator strains (M14459 for fHbp var.1; NZ98/254 for PorA P1.4; M4407 for NHBA; 96217 for NadA), in order to confirm that BEXSERO antigens' specific immunogenicity is preserved upon the addition of the new fusion protein. The results are reported in FIG. 16 (A-D). In these graphs, "BEXSERO PLUS PLUS" refers to the formulation BEXSERO+fHbp 231.13 E211A/S216R.

Immunogenicity Studies in Rabbit

Pooled hSBA data for the existing BEXSERO formulation and formulations comprising fusion proteins of the invention are further presented in FIG. 17A for var2/3 strain types, and in FIG. 17B for var.1.x strain types. The dashed lines represent hSBA threshold of 16 for rabbit sera.

All the formulations comprising fHbp fusion proteins according to the present invention provide improved coverage against var 2 and 3 strain panels compared to BEXSERO alone, and elicited higher hSBA titers against the majority of variant 1.x strains compared to BEXSERO alone.

As for the mouse study described above, a value of 256 (four times the initial threshold of 64) was chosen as a new threshold to analyse the rabbit data.

A coverage analysis was performed and is summarized in FIG. 18A (for var2/3 strains) and FIG. 18B (for var1.x strains). These results confirm that formulations comprising fHbp fusion proteins according to the present invention were able to cover a higher percentage of var2/3 strains than BEXSERO alone, and were able to cover a higher percentage of v1.x strains than both BEXSERO alone and BEXSERO+the prior art fHbp fusion 231.1_R41S (referred to in FIG. 18 as 2-3-1S).

Finally, non-inferiority of formulations comprising fHbp fusion proteins according to the present invention versus BEXSERO was confirmed testing the rabbit antisera against a panel of 11 strains including BEXSERO reference stains and fHbp var 1.1 and 1.4 strains in rabbit, as reported in FIG. 19.

These results show that non-inferiority was confirmed for all formulations comprising fHbp fusion proteins according to the present invention.

Example 7: Evaluation of Immunogenicity of 4CMenB+23(S)1.13 NB Mutant Vs 4CMenB+23(S)1.13 wt in a hFH Transgenic Mouse Model Immunization Protocol Two groups of 10 mice (transgenic mice expressing hfH) were immunized interaperitoneally (i.p.) with one of the two preparations, A and B:

Group A=4CMenB+fHbp 23(S)1.13 wild type
Group B=4CMenB+fHbp 23(S)1.13_E211A/S216R
One mouse (non-immunized) received only phosphate-buffered saline (PBS) as a control.
3 doses of immunization were performed at day 1, 22 and 36.
Blood samples were withdrawn before immunization and after the third dose.
Pre-immunization sera were pooled for each group.

Bacterial Challenge in Immunized Mice

Nine mice from each group were challenged (two mice died after sampling and before bacterial challenge; one from group A and one from group B). The mice were challenged i.p. using a bioluminescent variant of the serogroup B strain MC58 ($10^7$ CFU per mouse in 500 μl of saline).

Results

Dynamic imaging was performed 30 min and 6 h after infection and total photons per second were scored and expressed using the total photon per sec and per mouse as well as a ratio of total photon per second and per mouse after 6 h of infection/total photon per second and per mouse after 0.5 h of infection (FIG. 20).

The total photons emitted per mouse were computed and are presented in Figure. 21. In both groups, the signals were reduced significantly compared to non-infected mice. Mice of Group B showed lower total photon per second compared to group A, but this difference did not reach significant level (p=0.2) in FIG. 21A. However, if the analysis expressed as ratio 6 h/0.5 h of the signals (FIG. 21B), the difference is significant (p=0.007) (Mann Whitney test).

CONCLUSIONS

As can be seen from FIGS. 20 and 21, the mice in both groups, immunized with both preparations A and B, were protected against MC58 challenge, as evidenced by the post-infection clearance seen in mice from both groups at the 6-hour time point, compared with 0.5 hours. In contrast, the non-immunised mouse was unable to clear the infection by 6 hours post-challenge. However, clearance post-challenge was more profound in the group B mice, immunized with 4CMenB+fHbp 23(S)1.13_E211A/S216R, compared with group A mice immunized with 4CMenB+fHbp 23(S) 1.13 wild type.

Therefore, these in vivo data support the improved immunogenicity of a vaccine composition comprising a mutated non-fH binding fusion polypeptide according to the invention, compared with an equivalent composition comprising a fusion polypeptide that does not contain a non-binding double mutant v1.13 polypeptide of the invention.

The invention claimed is:

1. A mutant v1.13 meningococcal factor H binding protein (fHbp) polypeptide comprising an amino acid sequence having at least 80% sequence identity to SEQ ID NO: 2, wherein the amino acid sequence of the v1.13 meningococcal fHbp polypeptide comprises substitution mutations of SEQ ID NO:2 including the substitution mutation S216R and substitution mutation E211A.

2. The mutant v1.13 meningococcal fHbp polypeptide of claim 1, wherein the amino acid sequence comprises substitution mutations of SEQ ID NO: 2 including the substitution mutation S216R, the substitution mutation E211A, and substitution mutation E232A.

3. The mutant v1.13 meningococcal fHbp polypeptide of claim 1, comprising or consisting of the amino acid sequence of SEQ ID NO: 4.

* * * * *

SEQUENCE LISTING

<160> NUMBER OF SEQ ID NOS: 34

<210> SEQ ID NO 1
<211> LENGTH: 255
<212> TYPE: PRT
<213> ORGANISM: Neisseria meningitidis

<400> SEQUENCE: 1

Cys Ser Ser Gly Gly Gly Gly Val Ala Ala Asp Ile Gly Ala Gly Leu
1               5                   10                  15

Ala Asp Ala Leu Thr Ala Pro Leu Asp His Lys Asp Lys Gly Leu Gln
            20                  25                  30

Ser Leu Thr Leu Asp Gln Ser Val Arg Lys Asn Glu Lys Leu Lys Leu
        35                  40                  45

-continued

Ala Ala Gln Gly Ala Glu Lys Thr Tyr Gly Asn Gly Asp Ser Leu Asn
        50                  55                  60

Thr Gly Lys Leu Lys Asn Asp Lys Val Ser Arg Phe Asp Phe Ile Arg
65                  70                  75                  80

Gln Ile Glu Val Asp Gly Lys Leu Ile Thr Leu Glu Ser Gly Glu Phe
                85                  90                  95

Gln Val Tyr Lys Gln Ser His Ser Ala Leu Thr Ala Leu Gln Thr Glu
            100                 105                 110

Gln Val Gln Asp Ser Glu Asp Ser Gly Lys Met Val Ala Lys Arg Gln
        115                 120                 125

Phe Arg Ile Gly Asp Ile Ala Gly Glu His Thr Ser Phe Asp Lys Leu
    130                 135                 140

Pro Lys Gly Gly Ser Ala Thr Tyr Arg Gly Thr Ala Phe Gly Ser Asp
145                 150                 155                 160

Asp Ala Gly Gly Lys Leu Thr Tyr Thr Ile Asp Phe Ala Ala Lys Gln
                165                 170                 175

Gly His Gly Lys Ile Glu His Leu Lys Ser Pro Glu Leu Asn Val Glu
            180                 185                 190

Leu Ala Thr Ala Tyr Ile Lys Pro Asp Glu Lys Arg His Ala Val Ile
        195                 200                 205

Ser Gly Ser Val Leu Tyr Asn Gln Asp Glu Lys Gly Ser Tyr Ser Leu
    210                 215                 220

Gly Ile Phe Gly Gly Gln Ala Gln Glu Val Ala Gly Ser Ala Glu Val
225                 230                 235                 240

Glu Thr Ala Asn Gly Ile His His Ile Gly Leu Ala Ala Lys Gln
                245                 250                 255

<210> SEQ ID NO 2
<211> LENGTH: 248
<212> TYPE: PRT
<213> ORGANISM: Neisseria meningitidis

<400> SEQUENCE: 2

Val Ala Ala Asp Ile Gly Ala Gly Leu Ala Asp Ala Leu Thr Ala Pro
1               5                   10                  15

Leu Asp His Lys Asp Lys Gly Leu Gln Ser Leu Thr Leu Asp Gln Ser
            20                  25                  30

Val Arg Lys Asn Glu Lys Leu Lys Leu Ala Ala Gln Gly Ala Glu Lys
        35                  40                  45

Thr Tyr Gly Asn Gly Asp Ser Leu Asn Thr Gly Lys Leu Lys Asn Asp
50                  55                  60

Lys Val Ser Arg Phe Asp Phe Ile Arg Gln Ile Glu Val Asp Gly Lys
65                  70                  75                  80

Leu Ile Thr Leu Glu Ser Gly Glu Phe Gln Val Tyr Lys Gln Ser His
                85                  90                  95

Ser Ala Leu Thr Ala Leu Gln Thr Glu Gln Val Gln Asp Ser Glu Asp
            100                 105                 110

Ser Gly Lys Met Val Ala Lys Arg Gln Phe Arg Ile Gly Asp Ile Ala
        115                 120                 125

Gly Glu His Thr Ser Phe Asp Lys Leu Pro Lys Gly Gly Ser Ala Thr
    130                 135                 140

Tyr Arg Gly Thr Ala Phe Gly Ser Asp Asp Ala Gly Gly Lys Leu Thr
145                 150                 155                 160

Tyr Thr Ile Asp Phe Ala Ala Lys Gln Gly His Gly Lys Ile Glu His

```
                    165                 170                 175

Leu Lys Ser Pro Glu Leu Asn Val Glu Leu Ala Thr Ala Tyr Ile Lys
            180                 185                 190

Pro Asp Glu Lys Arg His Ala Val Ile Ser Gly Ser Val Leu Tyr Asn
        195                 200                 205

Gln Asp Glu Lys Gly Ser Tyr Ser Leu Gly Ile Phe Gly Gly Gln Ala
    210                 215                 220

Gln Glu Val Ala Gly Ser Ala Glu Val Glu Thr Ala Asn Gly Ile His
225                 230                 235                 240

His Ile Gly Leu Ala Ala Lys Gln
                245

<210> SEQ ID NO 3
<211> LENGTH: 248
<212> TYPE: PRT
<213> ORGANISM: Artificial Sequence
<220> FEATURE:
<223> OTHER INFORMATION: MUTATED fhbp POLYPEPTIDE

<400> SEQUENCE: 3

Val Ala Ala Asp Ile Gly Ala Gly Leu Ala Asp Ala Leu Thr Ala Pro
1               5                   10                  15

Leu Asp His Lys Asp Lys Gly Leu Gln Ser Leu Thr Leu Asp Gln Ser
            20                  25                  30

Val Arg Lys Asn Glu Lys Leu Lys Leu Ala Ala Gln Gly Ala Glu Lys
        35                  40                  45

Thr Tyr Gly Asn Gly Asp Ser Leu Asn Thr Gly Lys Leu Lys Asn Asp
    50                  55                  60

Lys Val Ser Arg Phe Asp Phe Ile Arg Gln Ile Glu Val Asp Gly Lys
65                  70                  75                  80

Leu Ile Thr Leu Glu Ser Gly Glu Phe Gln Val Tyr Lys Gln Ser His
                85                  90                  95

Ser Ala Leu Thr Ala Leu Gln Thr Glu Gln Val Gln Asp Ser Glu Asp
            100                 105                 110

Ser Gly Lys Met Val Ala Lys Arg Gln Phe Arg Ile Gly Asp Ile Ala
        115                 120                 125

Gly Glu His Thr Ser Phe Asp Lys Leu Pro Lys Gly Gly Ser Ala Thr
    130                 135                 140

Tyr Arg Gly Thr Ala Phe Gly Ser Asp Asp Ala Gly Gly Lys Leu Thr
145                 150                 155                 160

Tyr Thr Ile Asp Phe Ala Ala Lys Gln Gly His Gly Lys Ile Glu His
                165                 170                 175

Leu Lys Ser Pro Glu Leu Asn Val Glu Leu Ala Thr Ala Tyr Ile Lys
            180                 185                 190

Pro Asp Glu Lys Arg His Ala Val Ile Ser Gly Ser Val Leu Tyr Asn
        195                 200                 205

Gln Asp Ala Lys Gly Ser Tyr Ser Leu Gly Ile Phe Gly Gly Gln Ala
    210                 215                 220

Gln Glu Val Ala Gly Ser Ala Val Glu Thr Ala Asn Gly Ile His
225                 230                 235                 240

His Ile Gly Leu Ala Ala Lys Gln
                245

<210> SEQ ID NO 4
<211> LENGTH: 248
<212> TYPE: PRT
```

-continued

<213> ORGANISM: Artificial Sequence
<220> FEATURE:
<223> OTHER INFORMATION: MUTATED fhbp POLYPEPTIDE

<400> SEQ

-continued

Ile Thr Leu Glu Ser Gly Glu Phe Gln Val Tyr Lys Gln Ser His Ser
            100                 105                 110

Ala Leu Thr Ala Leu Gln Thr Glu Gln Val Gln Asp Ser Glu His Ser
        115                 120                 125

Gly Lys Met Val Ala Lys Arg Gln Phe Arg Ile Gly Asp Ile Val Gly
    130                 135                 140

Glu His Thr Ser Phe Gly Lys Leu Pro Lys Asp Val Met Ala Thr Tyr
145                 150                 155                 160

Arg Gly Thr Ala Phe Gly Ser Asp Asp Ala Gly Gly Lys Leu Thr Tyr
                165                 170                 175

Thr Ile Asp Phe Ala Ala Lys Gln Gly His Gly Lys Ile Glu His Leu
            180                 185                 190

Lys Ser Pro Glu Leu Asn Val Asp Leu Ala Ala Ala Asp Ile Lys Pro
        195                 200                 205

Asp Glu Lys His His Ala Val Ile Ser Gly Ser Val Leu Tyr Asn Gln
    210                 215                 220

Ala Glu Lys Gly Ser Tyr Ser Leu Gly Ile Phe Gly Gly Gln Ala Gln
225                 230                 235                 240

Glu Val Ala Gly Ser Ala Glu Val Glu Thr Ala Asn Gly Ile Arg His
                245                 250                 255

Ile Gly Leu Ala Ala Lys Gln
            260

<210> SEQ ID NO 6
<211> LENGTH: 251
<212> TYPE: PRT
<213> ORGANISM: Neisseria meningitidis

<400> SEQUENCE: 6

Val Ala Ala Asp Ile Gly Ala Gly Leu Ala Asp Ala Leu Thr Ala Pro
1               5                   10                  15

Leu Asp His Lys Asp Lys Gly Leu Lys Ser Leu Thr Leu Glu Asp Ser
            20                  25                  30

Ile Ser Gln Asn Gly Thr Leu Thr Leu Ser Ala Gln Gly Ala Glu Arg
        35                  40                  45

Thr Phe Lys Ala Gly Asp Lys Asp Asn Ser Leu Asn Thr Gly Lys Leu
    50                  55                  60

Lys Asn Asp Lys Ile Ser Arg Phe Asp Phe Ile Arg Gln Ile Glu Val
65                  70                  75                  80

Asp Gly Gln Leu Ile Thr Leu Glu Ser Gly Glu Phe Gln Val Tyr Lys
                85                  90                  95

Gln Ser His Ser Ala Leu Thr Ala Leu Gln Thr Glu Gln Val Gln Asp
            100                 105                 110

Ser Glu His Ser Gly Lys Met Val Ala Lys Arg Gln Phe Arg Ile Gly
        115                 120                 125

Asp Ile Val Gly Glu His Thr Ser Phe Gly Lys Leu Pro Lys Asp Val
    130                 135                 140

Met Ala Thr Tyr Arg Gly Thr Ala Phe Gly Ser Asp Asp Ala Gly Gly
145                 150                 155                 160

Lys Leu Thr Tyr Thr Ile Asp Phe Ala Ala Lys Gln Gly His Gly Lys
                165                 170                 175

Ile Glu His Leu Lys Ser Pro Glu Leu Asn Val Asp Leu Ala Ala Ala
            180                 185                 190

Asp Ile Lys Pro Asp Glu Lys His His Ala Val Ile Ser Gly Ser Val

```
            195                 200                 205
Leu Tyr Asn Gln Ala Glu Lys Gly Ser Tyr Ser Leu Gly Ile Phe Gly
    210                 215                 220
Gly Gln Ala Gln Glu Val Ala Gly Ser Ala Glu Val Glu Thr Ala Asn
225                 230                 235                 240
Gly Ile Arg His Ile Gly Leu Ala Ala Lys Gln
                245                 250

<210> SEQ ID NO 7
<211> LENGTH: 251
<212> TYPE: PRT
<213> ORGANISM: Artificial Sequence
<220> FEATURE:
<223> OTHER INFORMATION: MUTATED fhbp POLYPEPTIDE

<400> SEQUENCE: 7

Val Ala Ala Asp Ile Gly Ala Gly Leu Ala Asp Ala Leu Thr Ala Pro
1               5                   10                  15
Leu Asp His Lys Asp Lys Gly Leu Lys Ser Leu Thr Leu Glu Asp Ser
                20                  25                  30
Ile

Val Ala Ala Asp Ile Gly Ala Gly Leu Ala Asp Ala Leu Thr Ala Pro
1               5                   10                  15

Leu Asp His Lys Asp Lys Gly Leu Lys Ser Leu Thr Leu Glu Asp Ser
            20                  25                  30

Ile Ser Gln Asn Gly Thr Leu Thr Leu Ser Ala Gln Gly Ala Glu Arg
        35                  40                  45

Thr Phe Lys Ala Gly Asp Lys Asp Asn Ser Leu Asn Thr Gly Lys Leu
    50                  55                  60

Lys Asn Asp Lys Ile Ser Arg Phe Asp Phe Ile Arg Gln Ile Glu Val
65                  70                  75                  80

Asp Gly Gln Leu Ile Thr Leu Glu Ser Gly Glu Phe Gln Val Tyr Lys
                85                  90                  95

Gln Ser His Ser Ala Leu Thr Ala Leu Gln Thr Glu Gln Val Gln Asp
            100                 105                 110

Ser Glu His Ser Gly Lys Met Val Ala Lys Arg Gln Phe Arg Ile Gly
        115                 120                 125

Asp Ile Val Gly Glu His Thr Ser Phe Gly Lys Leu Pro Lys Asp Val
    130                 135                 140

Met Ala Thr Tyr Arg Gly Thr Ala Phe Gly Ser Asp Asp Ala Gly Gly
145                 150                 155                 160

Lys Leu Thr Tyr Thr Ile Asp Phe Ala Ala Lys Gln Gly His Gly Lys
                165                 170                 175

Ile Glu His Leu Lys Ser Pro Glu Leu Asn Val Asp Leu Ala Ala Ala
            180                 185                 190

Asp Ile Lys Pro Asp Glu Lys His His Ala Val Ile Ser Gly Ser Val
    195                 200                 205

Leu Tyr Asn Gln Ala Ala Lys Gly Ser Tyr Arg Leu Gly Ile Phe Gly
    210                 215                 220

Gly Gln Ala Gln Glu Val Ala Gly Ser Ala Glu Val Glu Thr Ala Asn
225                 230                 235                 240

Gly Ile Arg His Ile Gly Leu Ala Ala Lys Gln
                245                 250

<210> SEQ ID NO 9
<211> LENGTH: 251
<212> TYPE: PRT
<213> ORGANISM: Artificial Sequence
<220> FEATURE:
<223> OTHER INFORMATION: MUTATED fhbp POLYPEPTIDE

<400> SEQUENCE: 9

Val Ala Ala Asp Ile Gly Ala Gly Leu Ala Asp Ala Leu Thr Ala Pro
1               5                   10                  15

Leu Asp His Lys Asp Lys Gly Leu Lys Ser Leu Thr Leu Glu Asp Ser
            20                  25                  30

Ile Ser Gln Asn Gly Thr Leu Thr Leu Ser Ala Gln Gly Ala Glu Arg
        35                  40                  45

Thr Phe Lys Ala Gly Asp Lys Asp Asn Ser Leu Asn Thr Gly Lys Leu
    50                  55                  60

Lys Asn Asp Lys Ile Ser Arg Phe Asp Phe Ile Arg G

```
Ser Glu His Ser Gly Lys Met Val Ala Lys Arg Gln Phe Arg Ile Gly
            115                 120                 125

Asp Ile Val Gly Glu His Thr Ser Phe Gly Lys Leu Pro Lys Asp Val
130                 135                 140

Met Ala Thr Tyr Arg Gly Thr Ala Phe Gly Ser Asp Asp Ala Gly Gly
145                 150                 155                 160

Lys Leu Thr Tyr Thr Ile Asp Phe Ala Ala Lys Gln Gly His Gly Lys
                165                 170                 175

Ile Glu His Leu Lys Ser Pro Glu Leu Asn Val Asp Leu Ala Ala Ala
            180                 185                 190

Asp Ile Lys Pro Asp Glu Lys His His Ala Val Ile Ser Gly Ser Val
        195                 200                 205

Leu Tyr Asn Gln Ala Ala Lys Gly Ser Tyr Ser Leu Gly Ile Phe Gly
    210                 215                 220

Gly Gln Ala Gln Glu Val Ala Gly Ser Ala Ala Val Glu Thr Ala Asn
225                 230                 235                 240

Gly Ile Arg His Ile Gly Leu Ala Ala Lys Gln
                245                 250

<210> SEQ ID NO 10
<211> LENGTH: 273
<212> TYPE: PRT
<213> ORGANISM: Neisseria meningitidis

<400> SEQUENCE: 10

Met Asn Arg Thr Ala Phe Cys Cys Leu Ser Leu Thr Ala Ala Leu Ile
1               5                   10                  15

Leu Thr Ala Cys Ser Ser Gly Gly Gly Val Ala Ala Asp Ile Gly
            20                  25                  30

Ala Gly Leu Ala Asp Ala Leu Thr Ala Pro Leu Asp His Lys Asp Lys
        35                  40                  45

Ser Leu Gln Ser Leu Thr Leu Asp Gln Ser Val Arg Lys Asn Glu Lys
    50                  55                  60

Leu Lys Leu Ala Ala Gln Gly Ala Glu Lys Thr Tyr Gly Asn Gly Asp
65                  70                  75                  80

Ser Leu Asn Thr Gly Lys Leu Lys Asn Asp Lys Val Ser Arg Phe Asp
                85                  90                  95

Phe Ile Arg Gln Ile Glu Val Asp Gly Gln Leu Ile Thr Leu Glu Ser
            100                 105                 110

Gly Glu Phe Gln Ile Tyr Lys Gln Asp His Ser Ala Val Val Ala Leu
        115                 120                 125

Gln Ile Glu Lys Ile Asn Asn Pro Asp Lys Ile Asp Ser Leu Ile Asn
    130                 135                 140

Gln Arg Ser Phe Leu Val Ser Gly Leu Gly Gly Glu His Thr Ala Phe
145                 150                 155                 160

Asn Gln Leu Pro Asp Gly Lys Ala Glu Tyr His Gly Lys Ala Phe Ser
                165                 170                 175

Ser Asp Asp Ala Gly Gly Lys Leu Thr Tyr Thr Ile Asp Phe Ala Ala
            180                 185                 190

Lys Gln Gly His Gly Lys Ile Glu His Leu Lys Thr Pro Glu Gln Asn
        195                 200                 205

Val Glu Leu Ala Ala Ala Glu Leu Lys Ala Asp Glu Lys Ser His Ala
    210                 215                 220

Val Ile Leu Gly Asp Thr Arg Tyr Gly Ser Glu Glu Lys Gly Thr Tyr
225                 230                 235                 240
```

```
His Leu Ala Leu Phe Gly Asp Arg Ala Gln Glu Ile Ala Gly Ser Ala
                245                 250                 255
Thr Val Lys Ile Gly Glu Lys Val His Glu Ile Gly Ile Ala Gly Lys
            260                 265                 270
Gln

<210> SEQ ID NO 11
<211> LENGTH: 254
<212> TYPE: PRT
<213> ORGANISM: Neisseria meningitidis

<400> SEQUENCE: 11

Cys Ser Ser Gly Gly Gly Val Ala Ala Asp Ile Gly Ala Gly Leu
1               5                   10                  15
Ala Asp Ala Leu Thr Ala Pro Leu Asp His Lys Asp Lys Ser Leu Gln
            20                  25                  30
Ser Leu Thr Leu Asp Gln Ser Val Arg Lys Asn Glu Lys Leu Lys Leu
        35                  40                  45
Ala Ala Gln Gly Ala Glu Lys Thr Tyr Gly Asn Gly Asp Ser Leu Asn
    50                  55                  60
Thr Gly Lys Leu Lys Asn Asp Lys Val Ser Arg Phe Asp Phe Ile Arg
65                  70                  75                  80
Gln Ile Glu Val Asp Gly Gln Leu Ile Thr Leu Glu Ser Gly Glu Phe
                85                  90                  95
Gln Ile Tyr Lys Gln Asp His Ser Ala Val Val Ala Leu Gln Ile Glu
            100                 105                 110
Lys Ile Asn Asn Pro Asp Lys Ile Asp Ser Leu Ile Asn Gln Arg Ser
        115                 120                 125
Phe Leu Val Ser Gly Leu Gly Gly Glu His Thr Ala Phe Asn Gln Leu
    130                 135                 140
Pro Asp Gly Lys Ala Glu Tyr His Gly Lys Ala Phe Ser Ser Asp Asp
145                 150                 155                 160
Ala Gly Gly Lys Leu Thr Tyr Thr Ile Asp Phe Ala Ala Lys Gln Gly
                165                 170                 175
His Gly Lys Ile Glu His Leu Lys Thr Pro Glu Gln Asn Val Glu Leu
            180                 185                 190
Ala Ala Ala Glu Leu Lys Ala Asp Glu Lys Ser His Ala Val Ile Leu
        195                 200                 205
Gly Asp Thr Arg Tyr Gly Ser Glu Glu Lys Gly Thr Tyr His Leu Ala
    210                 215                 220
Leu Phe Gly Asp Arg Ala Gln Glu Ile Ala Gly Ser Ala Thr Val Lys
225                 230                 235                 240
Ile Gly Glu Lys Val His Glu Ile Gly Ile Ala Gly Lys Gln
                245                 250

<210> SEQ ID NO 12
<211> LENGTH: 247
<212> TYPE: PRT
<213> ORGANISM: Neisseria meningitidis

<400> SEQUENCE: 12

Val Ala Ala Asp Ile Gly Ala Gly Leu Ala Asp Ala Leu Thr Ala Pro
1               5                   10                  15
Leu Asp His Lys Asp Lys Ser Leu Gln Ser Leu Thr Leu Asp Gln Ser
            20                  25                  30
```

```
Val Arg Lys Asn Glu Lys Leu Lys Leu Ala Ala Gln Gly Ala Glu Lys
         35                  40                  45

Thr Tyr Gly Asn Gly Asp Ser Leu Asn Thr Gly Lys Leu Lys Asn Asp
 50                  55                  60

Lys Val Ser Arg Phe Asp Phe Ile Arg Gln Ile Glu Val Asp Gly Gln
 65                  70                  75                  80

Leu Ile Thr Leu Glu Ser Gly Glu Phe Gln Ile Tyr Lys Gln Asp His
                 85                  90                  95

Ser Ala Val Val Ala Leu Gln Ile Glu Lys Ile Asn Asn Pro Asp Lys
                100                 105                 110

Ile Asp Ser Leu Ile Asn Gln Arg Ser Phe Leu Val Ser Gly Leu Gly
            115                 120                 125

Gly Glu His Thr Ala Phe Asn Gln Leu Pro Asp Gly Lys Ala Glu Tyr
        130                 135                 140

His Gly Lys Ala Phe Ser Ser Asp Asp Ala Gly Gly Lys Leu Thr Tyr
145                 150                 155                 160

Thr Ile Asp Phe Ala Ala Lys Gln Gly His Gly Lys Ile Glu His Leu
                165                 170                 175

Lys Thr Pro Glu Gln Asn Val Glu Leu Ala Ala Ala Glu Leu Lys Ala
            180                 185                 190

Asp Glu Lys Ser His Ala Val Ile Leu Gly Asp Thr Arg Tyr Gly Ser
        195                 200                 205

Glu Glu Lys Gly Thr Tyr His Leu Ala Leu Phe Gly Asp Arg Ala Gln
    210                 215                 220

Glu Ile Ala Gly Ser Ala Thr Val Lys Ile Gly Glu Lys Val His Glu
225                 230                 235                 240

Ile Gly Ile Ala Gly Lys Gln
                245

<210> SEQ ID NO 13
<211> LENGTH: 281
<212> TYPE: PRT
<213> ORGANISM: Neisseria meningitidis

<400> SEQUENCE: 13

Met Asn Arg Thr Ala Phe Cys Cys Leu Ser Leu Thr Thr Ala Leu Ile
 1                5                  10                  15

Leu Thr Ala Cys Ser Ser Gly Gly Gly Ser Gly Gly Gly Gly Gly Val
            20                  25                  30

Ala Ala Asp Ile Gly Thr Gly Leu Ala Asp Ala Leu Thr Ala Pro Leu
         35                  40                  45

Asp His Lys Asp Lys Gly Leu Lys Ser Leu Thr Leu Glu Asp Ser Ile
 50                  55                  60

Pro Gln Asn Gly Thr Leu Thr Leu Ser Ala Gln Gly Ala Glu Lys Thr
 65                  70                  75                  80

Phe Lys Ala Gly Asp Lys Asp Asn Ser Leu Asn Thr Gly Lys Leu Lys
                 85                  90                  95

Asn Asp Lys Ile Ser Arg Phe Asp Phe Val Gln Lys Ile Glu Val Asp
                100                 105                 110

Gly Gln Thr Ile Thr Leu Ala Ser Gly Glu Phe Gln Ile Tyr Lys Gln
            115                 120                 125

Asn His Ser Ala Val Val Ala Leu Gln Ile Glu Lys Ile Asn Asn Pro
        130                 135                 140

Asp Lys Thr Asp Ser Leu Ile Asn Gln Arg Ser Phe Leu Val Ser Gly
145                 150                 155                 160
```

```
Leu Gly Gly Glu His Thr Ala Phe Asn Gln Leu Pro Gly Lys Ala
            165                 170                 175

Glu Tyr His Gly Lys Ala Phe Ser Ser Asp Asp Pro Asn Gly Arg Leu
            180                 185                 190

His Tyr Ser Ile Asp Phe Thr Lys Lys Gln Gly Tyr Gly Arg Ile Glu
            195                 200                 205

His Leu Lys Thr Leu Glu Gln Asn Val Glu Leu Ala Ala Ala Glu Leu
            210                 215                 220

Lys Ala Asp Glu Lys Ser His Ala Val Ile Leu Gly Asp Thr Arg Tyr
225                 230                 235                 240

Gly Ser Glu Glu Lys Gly Thr Tyr His Leu Ala Leu Phe Gly Asp Arg
            245                 250                 255

Ala Gln Glu Ile Ala Gly Ser Ala Thr Val Lys Ile Gly Glu Lys Val
            260                 265                 270

His Glu Ile Gly Ile Ala Gly Lys Gln
            275                 280

<210> SEQ ID NO 14
<211> LENGTH: 281
<212> TYPE: PRT
<213> ORGANISM: Neisseria meningitidis

<400> SEQUENCE: 14

Met Asn Arg Thr Ala Phe Cys Cys Leu Ser Leu Thr Thr Ala Leu Ile
1               5                   10                  15

Leu Thr Ala Cys Ser Ser Gly Gly Gly Ser Gly Gly Gly Gly Gly Val
            20                  25                  30

Ala Ala Asp Ile Gly Thr Gly Leu Ala Asp Ala Leu Thr Ala Pro Leu
            35                  40                  45

Asp His Lys Asp Lys Gly Leu Lys Ser Leu Thr Leu Glu Asp Ser Ile
        50                  55                  60

Pro Gln Asn Gly Thr Leu Thr Leu Ser Ala Gln Gly Ala Glu Lys Thr
65                  70                  75                  80

Phe Lys Ala Gly Asp Lys Asp Asn Ser Leu Asn Thr Gly Lys Leu Lys
            85                  90                  95

Asn Asp Lys Ile Ser Arg Phe Asp Phe Val Gln Lys Ile Glu Val Asp
            100                 105                 110

Gly Gln Thr Ile Thr Leu Ala Ser Gly Glu Phe Gln Ile Tyr Lys Gln
            115                 120                 125

Asn His Ser Ala Val Val Ala Leu Gln Ile Glu Lys Ile Asn Asn Pro
        130                 135                 140

Asp Lys Thr Asp Ser Leu Ile Asn Gln Arg Ser Phe Leu Val Ser Gly
145                 150                 155                 160

Leu Gly Gly Glu His Thr Ala Phe Asn Gln Leu Pro Gly Lys Ala
            165                 170                 175

Glu Tyr His Gly Lys Ala Phe Ser Ser Asp Asp Pro Asn Gly Arg Leu
            180                 185                 190

His Tyr Ser Ile Asp Phe Thr Lys Lys Gln Gly Tyr Gly Arg Ile Glu
            195                 200                 205

His Leu Lys Thr Leu Glu Gln Asn Val Glu Leu Ala Ala Ala Glu Leu
            210                 215                 220

Lys Ala Asp Glu Lys Ser His Ala Val Ile Leu Gly Asp Thr Arg Tyr
225                 230                 235                 240

Gly Ser Glu Glu Lys Gly Thr Tyr His Leu Ala Leu Phe Gly Asp Arg
```

```
                        245                 250                 255
Ala Gln Glu Ile Ala Gly Ser Ala Thr Val Lys Ile Gly Glu Lys Val
                260                 265                 270

His Glu Ile Gly Ile Ala Gly Lys Gln
        275                 280

<210> SEQ ID NO 15
<211> LENGTH: 250
<212> TYPE: PRT
<213> ORGANISM: Neisseria meningitidis

<400> SEQUENCE: 15

Val Ala Ala Asp Ile Gly Thr Gly Leu Ala Asp Ala Leu Thr Ala Pro
1               5                   10                  15

Leu Asp His Lys Asp Lys Gly Leu Lys Ser Leu Thr Leu Glu Asp Ser
                20                  25                  30

Ile Pro Gln Asn Gly Thr Leu Thr Leu Ser Ala Gln Gly Ala Glu Lys
            35                  40                  45

Thr Phe Lys Ala Gly Asp Lys Asp Asn Ser Leu Asn Thr Gly Lys Leu
        50                  55                  60

Lys Asn Asp Lys Ile Ser Arg Phe Asp Phe Val Gln Lys Ile Glu Val
65                  70                  75                  80

Asp Gly Gln Thr Ile Thr Leu Ala Ser Gly Glu Phe Gln Ile Tyr Lys
                85                  90                  95

Gln Asn His Ser Ala Val Val Ala Leu Gln Ile Glu Lys Ile Asn Asn
            100                 105                 110

Pro Asp Lys Thr Asp Ser Leu Ile Asn Gln Arg Ser Phe Leu Val Ser
        115                 120                 125

Gly Leu Gly Gly Glu His Thr Ala Phe Asn Gln Leu Pro Gly Gly Lys
    130                 135                 140

Ala Glu Tyr His Gly Lys Ala Phe Ser Ser Asp Asp Pro Asn Gly Arg
145                 150                 155                 160

Leu His Tyr Ser Ile Asp Phe Thr Lys Lys Gln Gly Tyr Gly Arg Ile
                165                 170                 175

Glu His Leu Lys Thr Leu Glu Gln Asn Val Glu Leu Ala Ala Ala Glu
            180                 185                 190

Leu Lys Ala Asp Glu Lys Ser His Ala Val Ile Leu Gly Asp Thr Arg
        195                 200                 205

Tyr Gly Ser Glu Glu Lys Gly Thr Tyr His Leu Ala Leu Phe Gly Asp
    210                 215                 220

Arg Ala Gln Glu Ile Ala Gly Ser Ala Thr Val Lys Ile Gly Glu Lys
225                 230                 235                 240

Val His Glu Ile Gly Ile Ala Gly Lys Gln
                245                 250

<210> SEQ ID NO 16
<211> LENGTH: 247
<212> TYPE: PRT
<213> ORGANISM: Artificial Sequence
<220> FEATURE:
<223> OTHER INFORMATION: MUTATED fhbp POLYPEPTIDE

<400> SEQUENCE: 16

```
Val Arg Lys Asn Glu Lys Leu Lys Leu Ala Ala Gln Gly Ala Glu Lys
            35                  40                  45

Thr Tyr Gly Asn Gly Asp Ser Leu Asn Thr Gly Lys Leu Lys Asn Asp
 50                      55                  60

Lys Val Ser Arg Phe Asp Phe Ile Arg Gln Ile Glu Val Asp Gly Gln
 65                  70                  75                  80

Leu Ile Thr Leu Glu Ser Gly Glu Phe Gln Ile Tyr Lys Gln Asp His
                 85                  90                  95

Ser Ala Val Val Ala Leu Gln Ile Glu Lys Ile Asn Asn Pro Asp Lys
            100                 105                 110

Ile Asp Ser Leu Ile Asn Gln Arg Ser Phe Arg Val Ser Gly Leu Gly
            115                 120                 125

Gly Glu His Thr Ala Phe Asn Gln Leu Pro Asp Gly Lys Ala Glu Tyr
 130                     135                 140

His Gly Lys Ala Phe Ser Ser Asp Ala Gly Gly Lys Leu Thr Tyr
 145                     150                 155                 160

Thr Ile Asp Phe Ala Ala Lys Gln Gly His Gly Lys Ile Glu His Leu
                 165                 170                 175

Lys Thr Pro Glu Gln Asn Val Glu Leu Ala Ala Ala Glu Leu Lys Ala
            180                 185                 190

Asp Glu Lys Ser His Ala Val Ile Leu Gly Asp Thr Arg Tyr Gly Ser
            195                 200                 205

Glu Glu Lys Gly Thr Tyr His Leu Ala Leu Phe Gly Asp Arg Ala Gln
 210                     215                 220

Glu Ile Ala Gly Ser Ala Thr Val Lys Ile Gly Glu Lys Val His Glu
 225                     230                 235                 240

Ile Gly Ile Ala Gly Lys Gln
             245

<210> SEQ ID NO 17
<211> LENGTH: 250
<212> TYPE: PRT
<213> ORGANISM: Artificial Sequence
<220> FEATURE:
<223> OTHER INFORMATION: MUTATED fhbp POLYPEPTIDE

<400> SEQUENCE: 17

Val Ala Ala Asp Ile Gly Thr Gly Leu Ala Asp Ala Leu Thr Ala Pro
 1               5                  10                  15

Leu Asp His Lys Asp Lys Gly Leu Lys Ser Leu Thr Leu Glu Asp Val
                20                  25                  30

Ile Pro Gln Asn Gly Thr Leu Thr Leu Ser Ala Gln Gly Ala Glu Lys
            35                  40                  45

Thr Phe Lys Ala Gly Asp Lys Asp Asn Ser Leu Asn Thr Gly Lys Leu
 50                      55                  60

Lys Asn Asp Lys Ile Ser Arg Phe Asp Phe Val Gln Lys Ile Glu Val
 65                  70                  75                  80

Asp Gly Gln Thr Ile Thr Leu Ala Ser Gly Glu Phe Gln Ile Tyr Lys
                 85                  90                  95

Gln Asn His Ser Ala Val Val Ala Leu Gln Ile Glu Lys Ile Asn Asn
            100                 105                 110

Pro Asp Lys Thr Asp Ser Leu Ile Asn Gln Arg Ser Phe Arg Val Ser
            115                 120                 125

Gly Leu Gly Gly Glu His Thr Ala Phe Asn Gln Leu Pro Gly Gly Lys
 130                     135                 140
```

```
Ala Glu Tyr His Gly Lys Ala Phe Ser Ser Asp Asp Pro Asn Gly Arg
145                 150                 155                 160

Leu His Tyr Ser Ile Asp Phe Thr Lys Lys Gln Gly Tyr Gly Arg Ile
            165                 170                 175

Glu His Leu Lys Thr Leu Glu Gln Asn Val Glu Leu Ala Ala Ala Glu
        180                 185                 190

Leu Lys Ala Asp Glu Lys Ser His Ala Val Ile Leu Gly Asp Thr Arg
    195                 200                 205

Tyr Gly Ser Glu Glu Lys Gly Thr Tyr His Leu Ala Leu Phe Gly Asp
210                 215                 220

Arg Ala Gln Glu Ile Ala Gly Ser Ala Thr Val Lys Ile Gly Glu Lys
225                 230                 235                 240

Val His Glu Ile Gly Ile Ala Gly Lys Gln
            245                 250
```

<210> SEQ ID NO 18
<211> LENGTH: 757
<212> TYPE: PRT
<213> ORGANISM: Artificial Sequence
<220> FEATURE:
<223> OTHER INFORMATION: MUTATED fhbp POLYPEPTIDE

<400> SEQUENCE: 18

```
Val Ala Ala Asp Ile Gly Ala Gly Leu Ala Asp Ala Leu Thr Ala Pro
1               5                   10                  15

Leu Asp His Lys Asp Lys Ser Leu Gln Ser Leu Thr Leu Asp Gln Val
            20                  25                  30

Val Arg Lys Asn Glu Lys Leu Lys Leu Ala Ala Gln Gly Ala Glu Lys
        35                  40                  45

Thr Tyr Gly Asn Gly Asp Ser Leu Asn Thr Gly Lys Leu Lys Asn Asp
    50                  55                  60

Lys Val Ser Arg Phe Asp Phe Ile Arg Gln Ile Glu Val Asp Gly Gln
65                  70                  75                  80

Leu Ile Thr Leu Glu Ser Gly Glu Phe Gln Ile Tyr Lys Gln Asp His
                85                  90                  95

Ser Ala Val Val Ala Leu Gln Ile Glu Lys Ile Asn Asn Pro Asp Lys
            100                 105                 110

Ile Asp Ser Leu Ile Asn Gln Arg Ser Phe Arg Val Ser Gly Leu Gly
        115                 120                 125

Gly Glu His Thr Ala Phe Asn Gln Leu Pro Asp Gly Lys Ala Glu Tyr
    130                 135                 140

His Gly Lys Ala Phe Ser Ser Asp Asp Ala Gly Gly Lys Leu Thr Tyr
145                 150                 155                 160

Thr Ile Asp Phe Ala Ala Lys Gln Gly His Gly Lys Ile Glu His Leu
                165                 170                 175

Lys Thr Pro Glu Gln Asn Val Glu Leu Ala Ala Ala Glu Leu Lys Ala
            180                 185                 190

Asp Glu Lys Ser His Ala Val Ile Leu Gly Asp Thr Arg Tyr Gly Ser
        195                 200                 205

Glu Glu Lys Gly Thr Tyr His Leu Ala Leu Phe Gly Asp Arg Ala Gln
    210                 215                 220

Glu Ile Ala Gly Ser Ala Thr Val Lys Ile Gly Glu Lys Val His Glu
225                 230                 235                 240

Ile Gly Ile Ala Gly Lys Gln Gly Ser Gly Gly Gly Val Ala Ala
                245                 250                 255
```

Asp Ile Gly Thr Gly Leu Ala Asp Ala Leu Thr Ala Pro Leu Asp His
        260                 265                 270

Lys Asp Lys Gly Leu Lys Ser Leu Thr Leu Glu Asp Val Ile Pro Gln
    275                 280                 285

Asn Gly Thr Leu Thr Leu Ser Ala Gln Gly Ala Glu Lys Thr Phe Lys
    290                 295                 300

Ala Gly Asp Lys Asp Asn Ser Leu Asn Thr Gly Lys Leu Lys Asn Asp
305                 310                 315                 320

Lys Ile Ser Arg Phe Asp Phe Val Gln Lys Ile Glu Val Asp Gly Gln
                325                 330                 335

Thr Ile Thr Leu Ala Ser Gly Glu Phe Gln Ile Tyr Lys Gln Asn His
        340                 345                 350

Ser Ala Val Val Ala Leu Gln Ile Glu Lys Ile Asn Asn Pro Asp Lys
    355                 360                 365

Thr Asp Ser Leu Ile Asn Gln Arg Ser Phe Arg Val Ser Gly Leu Gly
    370                 375                 380

Gly Glu His Thr Ala Phe Asn Gln Leu Pro Gly Gly Lys Ala Glu Tyr
385                 390                 395                 400

His Gly Lys Ala Phe Ser Ser Asp Asp Pro Asn Gly Arg Leu His Tyr
                405                 410                 415

Ser Ile Asp Phe Thr Lys Lys Gln Gly Tyr Gly Arg Ile Glu His Leu
        420                 425                 430

Lys Thr Leu Glu Gln Asn Val Glu Leu Ala Ala Ala Glu Leu Lys Ala
    435                 440                 445

Asp Glu Lys Ser His Ala Val Ile Leu Gly Asp Thr Arg Tyr Gly Ser
    450                 455                 460

Glu Glu Lys Gly Thr Tyr His Leu Ala Leu Phe Gly Asp Arg Ala Gln
465                 470                 475                 480

Glu Ile Ala Gly Ser Ala Thr Val Lys Ile Gly Glu Lys Val His Glu
                485                 490                 495

Ile Gly Ile Ala Gly Lys Gln Gly Ser Gly Gly Gly Val Ala Ala
        500                 505                 510

Asp Ile Gly Ala Gly Leu Ala Asp Ala Leu Thr Ala Pro Leu Asp His
        515                 520                 525

Lys Asp Lys Gly Leu Gln Ser Leu Thr Leu Asp Gln Ser Val Arg Lys
    530                 535                 540

Asn Glu Lys Leu Lys Leu Ala Ala Gln Gly Ala Glu Lys Thr Tyr Gly
545                 550                 555                 560

Asn Gly Asp Ser Leu Asn Thr Gly Lys Leu Lys Asn Asp Lys Val Ser
                565                 570                 575

Arg Phe Asp Phe Ile Arg Gln Ile Glu Val Asp Gly Lys Leu Ile Thr
        580                 585                 590

Leu Glu Ser Gly Glu Phe Gln Val Tyr Lys Gln Ser His Ser Ala Leu
    595                 600                 605

Thr Ala Leu Gln Thr Glu Gln Val Gln Asp Ser Glu Asp Ser Gly Lys
    610                 615                 620

Met Val Ala Lys Arg Gln Phe Arg Ile Gly Asp Ile Ala Gly Glu His
625                 630                 635                 640

Thr Ser Phe Asp Lys Leu Pro Lys Gly Gly Ser Ala Thr Tyr Arg Gly
                645                 650                 655

Thr Ala Phe Gly Ser Asp Asp Ala Gly Gly Lys Leu Thr Tyr Thr Ile
        660                 665                 670

```
Asp Phe Ala Ala Lys Gln Gly His Gly Lys Ile Glu His Leu Lys Ser
            675                 680                 685

Pro Glu Leu Asn Val Glu Leu Ala Thr Ala Tyr Ile Lys Pro Asp Glu
        690                 695                 700

Lys Arg His Ala Val Ile Ser Gly Ser Val Leu Tyr Asn Gln Asp Ala
705                 710                 715                 720

Lys Gly Ser Tyr Ser Leu Gly Ile Phe Gly Gly Gln Ala Gln Glu Val
                725                 730                 735

Ala Gly Ser Ala Ala Val Glu Thr Ala Asn Gly Ile His His Ile Gly
            740                 745                 750

Leu Ala Ala Lys Gln
        755

<210> SEQ ID NO 19
<211> LENGTH: 757
<212> TYPE: PRT
<213> ORGANISM: Artificial Sequence
<220> FEATURE:
<223> OTHER INFORMATION: MUTATED fhbp POLYPETIDE

<400> SEQUENCE: 19

Val Ala Ala Asp Ile Gly Ala Gly Leu Ala Asp Ala Leu Thr Ala Pro
1               5                   10                  15

Leu Asp His Lys Asp Lys Ser Leu Gln Ser Leu Thr Leu Asp Gln Val
            20                  25                  30

Val Arg Lys Asn Glu Lys Leu Lys Leu Ala Ala Gln Gly Ala Glu Lys
        35                  40                  45

Thr Tyr Gly Asn Gly Asp Ser Leu Asn Thr Gly Lys Leu Lys Asn Asp
    50                  55                  60

Lys Val Ser Arg Phe Asp Phe Ile Arg Gln Ile Glu Val Asp Gly Gln
65                  70                  75                  80

Leu Ile Thr Leu Glu Ser Gly Glu Phe Gln Ile Tyr Lys Gln Asp His
                85                  90                  95

Ser Ala Val Val Ala Leu Gln Ile Glu Lys Ile Asn Asn Pro Asp Lys
            100                 105                 110

Ile Asp Ser Leu Ile Asn Gln Arg Ser Phe Arg Val Ser Gly Leu Gly
        115                 120                 125

Gly Glu His Thr Ala Phe Asn Gln Leu Pro Asp Gly Lys Ala Glu Tyr
    130                 135                 140

His Gly Lys Ala Phe Ser Ser Asp Asp Ala Gly Gly Lys Leu Thr Tyr
145                 150                 155                 160

Thr Ile Asp Phe Ala Ala Lys Gln Gly His Gly Lys Ile Glu His Leu
                165                 170                 175

Lys Thr Pro Glu Gln Asn Val Glu Leu Ala Ala Ala Glu Leu Lys Ala
            180                 185                 190

Asp Glu Lys Ser His Ala Val Ile Leu Gly Asp Thr Arg Tyr Gly Ser
        195                 200                 205

Glu Glu Lys Gly Thr Tyr His Leu Ala Leu Phe Gly Asp Arg Ala Gln
    210                 215                 220

Glu Ile Ala Gly Ser Ala Thr Val Lys Ile Gly Glu Lys Val His Glu
225                 230                 235                 240

Ile Gly Ile Ala Gly Lys Gln Gly Ser Gly Gly Gly Val Ala Ala
                245                 250                 255

Asp Ile Gly Thr Gly Leu Ala Asp Ala Leu Thr Ala Pro Leu Asp His
            260                 265                 270
```

```
Lys Asp Lys Gly Leu Lys Ser Leu Thr Leu Glu Asp Val Ile Pro Gln
            275                 280                 285

Asn Gly Thr Leu Thr Leu Ser Ala Gln Gly Ala Glu Lys Thr Phe Lys
290                 295                 300

Ala Gly Asp Lys Asp Asn Ser Leu Asn Thr Gly Lys Leu Lys Asn Asp
305                 310                 315                 320

Lys Ile Ser Arg Phe Asp Phe Val Gln Lys Ile Glu Val Asp Gly Gln
                325                 330                 335

Thr Ile Thr Leu Ala Ser Gly Glu Phe Gln Ile Tyr Lys Gln Asn His
            340                 345                 350

Ser Ala Val Val Ala Leu Gln Ile Glu Lys Ile Asn Asn Pro Asp Lys
        355                 360                 365

Thr Asp Ser Leu Ile Asn Gln Arg Ser Phe Arg Val Ser Gly Leu Gly
370                 375                 380

Gly Glu His Thr Ala Phe Asn Gln Leu Pro Gly Gly Lys Ala Glu Tyr
385                 390                 395                 400

His Gly Lys Ala Phe Ser Ser Asp Pro Asn Gly Arg Leu His Tyr
                405                 410                 415

Ser Ile Asp Phe Thr Lys Lys Gln Gly Tyr Gly Arg Ile Glu His Leu
                420                 425                 430

Lys Thr Leu Glu Gln Asn Val Glu Leu Ala Ala Ala Glu Leu Lys Ala
            435                 440                 445

Asp Glu Lys Ser His Ala Val Ile Leu Gly Asp Thr Arg Tyr Gly Ser
        450                 455                 460

Glu Glu Lys Gly Thr Tyr His Leu Ala Leu Phe Gly Asp Arg Ala Gln
465                 470                 475                 480

Glu Ile Ala Gly Ser Ala Thr Val Lys Ile Gly Glu Lys Val His Glu
                485                 490                 495

Ile Gly Ile Ala Gly Lys Gln Gly Ser Gly Gly Gly Val Ala Ala
                500                 505                 510

Asp Ile Gly Ala Gly Leu Ala Asp Ala Leu Thr Ala Pro Leu Asp His
            515                 520                 525

Lys Asp Lys Gly Leu Gln Ser Leu Thr Leu Asp Gln Ser Val Arg Lys
        530                 535                 540

Asn Glu Lys Leu Lys Leu Ala Ala Gln Gly Ala Glu Lys Thr Tyr Gly
545                 550                 555                 560

Asn Gly Asp Ser Leu Asn Thr Gly Lys Leu Lys Asn Asp Lys Val Ser
                565                 570                 575

Arg Phe Asp Phe Ile Arg Gln Ile Glu Val Asp Gly Lys Leu Ile Thr
                580                 585                 590

Leu Glu Ser Gly Glu Phe Gln Val Tyr Lys Gln Ser His Ser Ala Leu
            595                 600                 605

Thr Ala Leu Gln Thr Glu Gln Val Gln Asp Ser Glu Asp Ser Gly Lys
        610                 615                 620

Met Val Ala Lys Arg Gln Phe Arg Ile Gly Asp Ile Ala Gly Glu His
625                 630                 635                 640

Thr Ser Phe Asp Lys Leu Pro Lys Gly Gly Ser Ala Thr Tyr Arg Gly
                645                 650                 655

Thr Ala Phe Gly Ser Asp Asp Ala Gly Gly Lys Leu Thr Tyr Thr Ile
                660                 665                 670

Asp Phe Ala Ala Lys Gln Gly His Gly Lys Ile Glu His Leu Lys Ser
            675                 680                 685

Pro Glu Leu Asn Val Glu Leu Ala Thr Ala Tyr Ile Lys Pro Asp Glu
```

690                 695                 700

Lys Arg His Ala Val Ile Ser Gly Ser Val Leu Tyr Asn Gln Asp Ala
705                 710                 715                 720

Lys Gly Ser Tyr Arg Leu Gly Ile Phe Gly Gly Gln Ala Gln Glu Val
                  725                 730                 735

Ala Gly Ser Ala Glu Val Glu Thr Ala Asn Gly Ile His His Ile Gly
                  740                 745                 750

Leu Ala Ala Lys Gln
            755

<210> SEQ ID NO 20
<211> LENGTH: 760
<212> TYPE: PRT
<213> ORGANISM: Artificial Sequence
<220> FEATURE:
<223> OTHER INFORMATION: MUTATED fhbp POLYPEPTIDE

<400> SEQUENCE: 20

Val Ala Ala Asp Ile Gly Ala Gly Leu Ala Asp Ala Leu Thr Ala Pro
1               5                   10                  15

Leu Asp His Lys Asp Lys Ser Leu Gln Ser Leu Thr Leu Asp Gln Val
                20                  25                  30

Val Arg Lys Asn Glu Lys Leu Lys Leu Ala Ala Gln Gly Ala Glu Lys
            35                  40                  45

Thr Tyr Gly Asn Gly Asp Ser Leu Asn Thr Gly Lys Leu Lys Asn Asp
    50                  55                  60

Lys Val Ser Arg Phe Asp Phe Ile Arg Gln Ile Glu Val Asp Gly Gln
65                  70                  75                  80

Leu Ile Thr Leu Glu Ser Gly Glu Phe Gln Ile Tyr Lys Gln Asp His
                85                  90                  95

Ser Ala Val Val Ala Leu Gln Ile Glu Lys Ile Asn Asn Pro Asp Lys
                100                 105                 110

Ile Asp Ser Leu Ile Asn Gln Arg Ser Phe Arg Val Ser Gly Leu Gly
            115                 120                 125

Gly Glu His Thr Ala Phe Asn Gln Leu Pro Asp Gly Lys Ala Glu Tyr
    130                 135                 140

His Gly Lys Ala Phe Ser Ser Asp Asp Ala Gly Gly Lys Leu Thr Tyr
145                 150                 155                 160

Thr Ile Asp Phe Ala Ala Lys Gln Gly His Gly Lys Ile Glu His Leu
                165                 170                 175

Lys Thr Pro Glu Gln Asn Val Glu Leu Ala Ala Ala Glu Leu Lys Ala
                180                 185                 190

Asp Glu Lys Ser His Ala Val Ile Leu Gly Asp Thr Arg Tyr Gly Ser
            195                 200                 205

Glu Glu Lys Gly Thr Tyr His Leu Ala Leu Phe Gly Asp Arg Ala Gln
    210                 215                 220

Glu Ile Ala Gly Ser Ala Thr Val Lys Ile Gly Glu Lys Val His Glu
225                 230                 235                 240

Ile Gly Ile Ala Gly Lys Gln Gly Ser Gly Gly Gly Val Ala Ala
                245                 250                 255

Asp Ile Gly Thr Gly Leu Ala Asp Ala Leu Thr Ala Pro Leu Asp His
                260                 265                 270

Lys Asp Lys Gly Leu Lys Ser Leu Thr Leu Glu Asp Val Ile Pro Gln
            275                 280                 285

Asn Gly Thr Leu Thr Leu Ser Ala Gln Gly Ala Glu Lys Thr Phe Lys

```
                290                 295                 300
Ala Gly Asp Lys Asp Asn Ser Leu Asn Thr Gly Lys Leu Lys Asn Asp
305                 310                 315                 320

Lys Ile Ser Arg Phe Asp Phe Val Gln Lys Ile Glu Val Asp Gly Gln
                325                 330                 335

Thr Ile Thr Leu Ala Ser Gly Glu Phe Gln Ile Tyr Lys Gln Asn His
                340                 345                 350

Ser Ala Val Val Ala Leu Gln Ile Glu Lys Ile Asn Asn Pro Asp Lys
                355                 360                 365

Thr Asp Ser Leu Ile Asn Gln Arg Ser Phe Arg Val Ser Gly Leu Gly
                370                 375                 380

Gly Glu His Thr Ala Phe Asn Gln Leu Pro Gly Gly Lys Ala Glu Tyr
385                 390                 395                 400

His Gly Lys Ala Phe Ser Ser Asp Pro Asn Gly Arg Leu His Tyr
                405                 410                 415

Ser Ile Asp Phe Thr Lys Lys Gln Gly Tyr Gly Arg Ile Glu His Leu
                420                 425                 430

Lys Thr Leu Glu Gln Asn Val Glu Leu Ala Ala Ala Glu Leu Lys Ala
                435                 440                 445

Asp Glu Lys Ser His Ala Val Ile Leu Gly Asp Thr Arg Tyr Gly Ser
450                 455                 460

Glu Glu Lys Gly Thr Tyr His Leu Ala Leu Phe Gly Asp Arg Ala Gln
465                 470                 475                 480

Glu Ile Ala Gly Ser Ala Thr Val Lys Ile Gly Glu Lys Val His Glu
                485                 490                 495

Ile Gly Ile Ala Gly Lys Gln Gly Ser Gly Gly Gly Val Ala Ala
                500                 505                 510

Asp Ile Gly Ala Gly Leu Ala Asp Ala Leu Thr Ala Pro Leu Asp His
                515                 520                 525

Lys Asp Lys Gly Leu Lys Ser Leu Thr Leu Glu Asp Ser Ile Ser Gln
530                 535                 540

Asn Gly Thr Leu Thr Leu Ser Ala Gln Gly Ala Glu Arg Thr Phe Lys
545                 550                 555                 560

Ala Gly Asp Lys Asp Asn Ser Leu Asn Thr Gly Lys Leu Lys Asn Asp
                565                 570                 575

Lys Ile Ser Arg Phe Asp Phe Ile Arg Gln Ile Glu Val Asp Gly Gln
                580                 585                 590

Leu Ile Thr Leu Glu Ser Gly Glu Phe Gln Val Tyr Lys Gln Ser His
                595                 600                 605

Ser Ala Leu Thr Ala Leu Gln Thr Glu Gln Val Gln Asp Ser Glu His
                610                 615                 620

Ser Gly Lys Met Val Ala Lys Arg Gln Phe Arg Ile Gly Asp Ile Val
625                 630                 635                 640

Gly Glu His Thr Ser Phe Gly Lys Leu Pro Lys Asp Val Met Ala Thr
                645                 650                 655

Tyr Arg Gly Thr Ala Phe Gly Ser Asp Asp Ala Gly Gly Lys Leu Thr
                660                 665                 670

Tyr Thr Ile Asp Phe Ala Ala Lys Gln Gly His Gly Lys Ile Glu His
                675                 680                 685

Leu Lys Ser Pro Glu Leu Asn Val Asp Leu Ala Ala Ala Asp Ile Lys
                690                 695                 700

Pro Asp Glu Lys His His Ala Val Ile Ser Gly Ser Val Leu Tyr Asn
705                 710                 715                 720
```

Gln Ala Glu Lys Gly Ser Tyr Arg Leu Gly Ile Phe Gly Gly Gln Ala
                    725                 730                 735

Gln Glu Val Ala Gly Ser Ala Glu Val Glu Thr Ala Asn Gly Ile Arg
                740                 745                 750

His Ile Gly Leu Ala Ala Lys Gln
            755                 760

<210> SEQ ID NO 21
<211> LENGTH: 760
<212> TYPE: PRT
<213> ORGANISM: Artificial Sequence
<220> FEATURE:
<223> OTHER INFORMATION: MUTATED fhbp POLYPEPTIDE

<400> SEQUENCE: 21

Val Ala Ala Asp Ile Gly Ala Gly Leu Ala Asp Ala Leu Thr Ala Pro
1               5                   10                  15

Leu Asp His Lys Asp Lys Ser Leu Gln Ser Leu Thr Leu Asp Gln Val
                20                  25                  30

Val Arg Lys Asn Glu Lys Leu Lys Leu Ala Ala Gln Gly Ala Glu Lys
            35                  40                  45

Thr Tyr Gly Asn Gly Asp Ser Leu Asn Thr Gly Lys Leu Lys Asn Asp
    50                  55                  60

Lys Val Ser Arg Phe Asp Phe Ile Arg Gln Ile Glu Val Asp Gly Gln
65                  70                  75                  80

Leu Ile Thr Leu Glu Ser Gly Glu Phe Gln Ile Tyr Lys Gln Asp His
                85                  90                  95

Ser Ala Val Val Ala Leu Gln Ile Glu Lys Ile Asn Asn Pro Asp Lys
                100                 105                 110

Ile Asp Ser Leu Ile Asn Gln Arg Ser Phe Arg Val Ser Gly Leu Gly
            115                 120                 125

Gly Glu His Thr Ala Phe Asn Gln Leu Pro Asp Gly Lys Ala Glu Tyr
    130                 135                 140

His Gly Lys Ala Phe Ser Ser Asp Asp Ala Gly Gly Lys Leu Thr Tyr
145                 150                 155                 160

Thr Ile Asp Phe Ala Ala Lys Gln Gly His Gly Lys Ile Glu His Leu
                165                 170                 175

Lys Thr Pro Glu Gln Asn Val Glu Leu Ala Ala Ala Glu Leu Lys Ala
            180                 185                 190

Asp Glu Lys Ser His Ala Val Ile Leu Gly Asp Thr Arg Tyr Gly Ser
    195                 200                 205

Glu Glu Lys Gly Thr Tyr His Leu Ala Leu Phe Gly Asp Arg Ala Gln
210                 215                 220

Glu Ile Ala Gly Ser Ala Thr Val Lys Ile Gly Glu Lys Val His Glu
225                 230                 235                 240

Ile Gly Ile Ala Gly Lys Gln Gly Ser Gly Gly Gly Val Ala Ala
                245                 250                 255

Asp Ile Gly Thr Gly Leu Ala Asp Ala Leu Thr Ala Pro Leu Asp His
            260                 265                 270

Lys Asp Lys Gly Leu Lys Ser Leu Thr Leu Glu Asp Val Ile Pro Gln
    275                 280                 285

Asn Gly Thr Leu Thr Leu Ser Ala Gln Gly Ala Glu Lys Thr Phe Lys
290                 295                 300

Ala Gly Asp Lys Asp Asn Ser Leu Asn Thr Gly Lys Leu Lys Asn Asp
305                 310                 315                 320

```
Lys Ile Ser Arg Phe Asp Phe Val Gln Lys Ile Glu Val Asp Gly Gln
                325                 330                 335

Thr Ile Thr Leu Ala Ser Gly Glu Phe Gln Ile Tyr Lys Gln Asn His
                340                 345                 350

Ser Ala Val Val Ala Leu Gln Ile Glu Lys Ile Asn Asn Pro Asp Lys
                355                 360                 365

Thr Asp Ser Leu Ile Asn Gln Arg Ser Phe Arg Val Ser Gly Leu Gly
                370                 375                 380

Gly Glu His Thr Ala Phe Asn Gln Leu Pro Gly Gly Lys Ala Glu Tyr
385                 390                 395                 400

His Gly Lys Ala Phe Ser Ser Asp Asp Pro Asn Gly Arg Leu His Tyr
                405                 410                 415

Ser Ile Asp Phe Thr Lys Lys Gln Gly Tyr Gly Arg Ile Glu His Leu
                420                 425                 430

Lys Thr Leu Glu Gln Asn Val Glu Leu Ala Ala Ala Glu Leu Lys Ala
                435                 440                 445

Asp Glu Lys Ser His Ala Val Ile Leu Gly Asp Thr Arg Tyr Gly Ser
                450                 455                 460

Glu Glu Lys Gly Thr Tyr His Leu Ala Leu Phe Gly Asp Arg Ala Gln
465                 470                 475                 480

Glu Ile Ala Gly Ser Ala Thr Val Lys Ile Gly Glu Lys Val His Glu
                485                 490                 495

Ile Gly Ile Ala Gly Lys Gln Gly Ser Gly Gly Gly Val Ala Ala
                500                 505                 510

Asp Ile Gly Ala Gly Leu Ala Asp Ala Leu Thr Ala Pro Leu Asp His
                515                 520                 525

Lys Asp Lys Gly Leu Lys Ser Leu Thr Leu Glu Asp Ser Ile Ser Gln
530                 535                 540

Asn Gly Thr Leu Thr Leu Ser Ala Gln Gly Ala Glu Arg Thr Phe Lys
545                 550                 555                 560

Ala Gly Asp Lys Asp Asn Ser Leu Asn Thr Gly Lys Leu Lys Asn Asp
                565                 570                 575

Lys Ile Ser Arg Phe Asp Phe Ile Arg Gln Ile Glu Val Asp Gly Gln
                580                 585                 590

Leu Ile Thr Leu Glu Ser Gly Glu Phe Gln Val Tyr Lys Gln Ser His
                595                 600                 605

Ser Ala Leu Thr Ala Leu Gln Thr Glu Gln Val Gln Asp Ser Glu His
                610                 615                 620

Ser Gly Lys Met Val Ala Lys Arg Gln Phe Arg Ile Gly Asp Ile Val
625                 630                 635                 640

Gly Glu His Thr Ser Phe Gly Lys Leu Pro Lys Asp Val Met Ala Thr
                645                 650                 655

Tyr Arg Gly Thr Ala Phe Gly Ser Asp Asp Ala Gly Gly Lys Leu Thr
                660                 665                 670

Tyr Thr Ile Asp Phe Ala Ala Lys Gln Gly His Gly Lys Ile Glu His
                675                 680                 685

Leu Lys Ser Pro Glu Leu Asn Val Asp Leu Ala Ala Ala Asp Ile Lys
                690                 695                 700

Pro Asp Glu Lys His His Ala Val Ile Ser Gly Ser Val Leu Tyr Asn
705                 710                 715                 720

Gln Ala Ala Lys Gly Ser Tyr Arg Leu Gly Ile Phe Gly Gly Gln Ala
                725                 730                 735
```

```
Gln Glu Val Ala Gly Ser Ala Glu Val Thr Ala Asn Gly Ile Arg
            740                 745                 750

His Ile Gly Leu Ala Ala Lys Gln
        755                 760

<210> SEQ ID NO 22
<211> LENGTH: 760
<212> TYPE: PRT
<213> ORGANISM: Artificial Sequence
<220> FEATURE:
<223> OTHER INFORMATION: MUTATED fhbp POLYPEPTIDE

<400> SEQUENCE: 22

Val Ala Ala Asp Ile Gly Ala Gly Leu Ala Asp Ala Leu Thr Ala Pro
1               5                   10                  15

Leu Asp His Lys Asp Lys Ser Leu Gln Ser Leu Thr Leu Asp Gln Val
            20                  25                  30

Val Arg Lys Asn Glu Lys Leu Lys Leu Ala Ala Gln Gly Ala Glu Lys
        35                  40                  45

Thr Tyr Gly Asn Gly Asp Ser Leu Asn Thr Gly Lys Leu Lys Asn Asp
    50                  55                  60

Lys Val Ser Arg Phe Asp Phe Ile Arg Gln Ile Glu Val Asp Gly Gln
65                  70                  75                  80

Leu Ile Thr Leu Glu Ser Gly Glu Phe Gln Ile Tyr Lys Gln Asp His
                85                  90                  95

Ser Ala Val Val Ala Leu Gln Ile Glu Lys Ile Asn Asn Pro Asp Lys
            100                 105                 110

Ile Asp Ser Leu Ile Asn Gln Arg Ser Phe Arg Val Ser Gly Leu Gly
        115                 120                 125

Gly Glu His Thr Ala Phe Asn Gln Leu Pro Asp Gly Lys Ala Glu Tyr
    130                 135                 140

His Gly Lys Ala Phe Ser Ser Asp Ala Gly Gly Lys Leu Thr Tyr
145                 150                 155                 160

Thr Ile Asp Phe Ala Ala Lys Gln Gly His Gly Lys Ile Glu His Leu
                165                 170                 175

Lys Thr Pro Glu Gln Asn Val Glu Leu Ala Ala Ala Glu Leu Lys Ala
            180                 185                 190

Asp Glu Lys Ser His Ala Val Ile Leu Gly Asp Thr Arg Tyr Gly Ser
        195                 200                 205

Glu Glu Lys Gly Thr Tyr His Leu Ala Leu Phe Gly Asp Arg Ala Gln
    210                 215                 220

Glu Ile Ala Gly Ser Ala Thr Val Lys Ile Gly Glu Lys Val His Glu
225                 230                 235                 240

Ile Gly Ile Ala Gly Lys Gln Gly Ser Gly Gly Gly Val Ala Ala
                245                 250                 255

Asp Ile Gly Thr Gly Leu Ala Asp Ala Leu Thr Ala Pro Leu Asp His
            260                 265                 270

Lys Asp Lys Gly Leu Lys Ser Leu Thr Leu Glu Asp Val Ile Pro Gln
        275                 280                 285

Asn Gly Thr Leu Thr Leu Ser Ala Gln Gly Ala Glu Lys Thr Phe Lys
    290                 295                 300

Ala Gly Asp Lys Asp Asn Ser Leu Asn Thr Gly Lys Leu Lys Asn Asp
305                 310                 315                 320

Lys Ile Ser Arg Phe Asp Phe Val Gln Lys Ile Glu Val Asp Gly Gln
                325                 330                 335
```

```
Thr Ile Thr Leu Ala Ser Gly Glu Phe Gln Ile Tyr Lys Gln Asn His
            340                 345                 350

Ser Ala Val Val Ala Leu Gln Ile Glu Lys Ile Asn Asn Pro Asp Lys
        355                 360                 365

Thr Asp Ser Leu Ile Asn Gln Arg Ser Phe Arg Val Ser Gly Leu Gly
    370                 375                 380

Gly Glu His Thr Ala Phe Asn Gln Leu Pro Gly Gly Lys Ala Glu Tyr
385                 390                 395                 400

His Gly Lys Ala Phe Ser Ser Asp Pro Asn Gly Arg Leu His Tyr
                405                 410                 415

Ser Ile Asp Phe Thr Lys Lys Gln Gly Tyr Gly Arg Ile Glu His Leu
            420                 425                 430

Lys Thr Leu Glu Gln Asn Val Glu Leu Ala Ala Ala Glu Leu Lys Ala
        435                 440                 445

Asp Glu Lys Ser His Ala Val Ile Leu Gly Asp Thr Arg Tyr Gly Ser
        450                 455                 460

Glu Glu Lys Gly Thr Tyr His Leu Ala Leu Phe Gly Asp Arg Ala Gln
465                 470                 475                 480

Glu Ile Ala Gly Ser Ala Thr Val Lys Ile Gly Glu Lys Val His Glu
            485                 490                 495

Ile Gly Ile Ala Gly Lys Gln Gly Ser Gly Gly Gly Val Ala Ala
            500                 505                 510

Asp Ile Gly Ala Gly Leu Ala Asp Ala Leu Thr Ala Pro Leu Asp His
        515                 520                 525

Lys Asp Lys Gly Leu Lys Ser Leu Thr Leu Glu Asp Ser Ile Ser Gln
        530                 535                 540

Asn Gly Thr Leu Thr Leu Ser Ala Gln Gly Ala Glu Arg Thr Phe Lys
545                 550                 555                 560

Ala Gly Asp Lys Asp Asn Ser Leu Asn Thr Gly Lys Leu Lys Asn Asp
                565                 570                 575

Lys Ile Ser Arg Phe Asp Phe Ile Arg Gln Ile Glu Val Asp Gly Gln
            580                 585                 590

Leu Ile Thr Leu Glu Ser Gly Glu Phe Gln Val Tyr Lys Gln Ser His
        595                 600                 605

Ser Ala Leu Thr Ala Leu Gln Thr Glu Gln Val Gln Asp Ser Glu His
        610                 615                 620

Ser Gly Lys Met Val Ala Lys Arg Gln Phe Arg Ile Gly Asp Ile Val
625                 630                 635                 640

Gly Glu His Thr Ser Phe Gly Lys Leu Pro Lys Asp Val Met Ala Thr
            645                 650                 655

Tyr Arg Gly Thr Ala Phe Gly Ser Asp Asp Ala Gly Gly Lys Leu Thr
            660                 665                 670

Tyr Thr Ile Asp Phe Ala Ala Lys Gln Gly His Gly Lys Ile Glu His
        675                 680                 685

Leu Lys Ser Pro Glu Leu Asn Val Asp Leu Ala Ala Ala Asp Ile Lys
        690                 695                 700

Pro Asp Glu Lys His His Ala Val Ile Ser Gly Ser Val Leu Tyr Asn
705                 710                 715                 720

Gln Ala Ala Lys Gly Ser Tyr Ser Leu Gly Ile Phe Gly Gly Gln Ala
                725                 730                 735

Gln Glu Val Ala Gly Ser Ala Val Glu Thr Ala Asn Gly Ile Arg
            740                 745                 750

His Ile Gly Leu Ala Ala Lys Gln
```

```
              755                 760
```

<210> SEQ ID NO 23
<211> LENGTH: 256
<212> TYPE: PRT
<213> ORGANISM: Artificial Sequence
<220> FEATURE:
<223> OTHER INFORMATION: fHbp polypeptide with His6 tag

<400> SEQUENCE: 23

```
Val Ala Ala Asp Ile Gly Ala Gly Leu Ala Asp Ala Leu Thr Ala Pro
1               5                   10                  15

Leu Asp His Lys Asp Lys Gly Leu Gln Ser Leu Thr Leu Asp Gln Ser
            20                  25                  30

Val Arg Lys Asn Glu Lys Leu Lys Leu Ala Ala Gln Gly Ala Glu Lys
        35                  40                  45

Thr Tyr Gly Asn Gly Asp Ser Leu Asn Thr Gly Lys Leu Lys Asn Asp
    50                  55                  60

Lys Val Ser Arg Phe Asp Phe Ile Arg Gln Ile Glu Val Asp Gly Gln
65                  70                  75                  80

Leu Ile Thr Leu Glu Ser Gly Glu Phe Gln Val Tyr Lys Gln Ser His
                85                  90                  95

Ser Ala Leu Thr Ala Phe Gln Thr Glu Gln Ile Gln Asp Ser Glu His
            100                 105                 110

Ser Gly Lys Met Val Ala Lys Arg Gln Phe Arg Ile Gly Asp Ile Ala
        115                 120                 125

Gly Glu His Thr Ser Phe Asp Lys Leu Pro Glu Gly Gly Arg Ala Thr
    130                 135                 140

Tyr Arg Gly Thr Ala Phe Gly Ser Asp Asp Ala Gly Gly Lys Leu Thr
145                 150                 155                 160

Tyr Thr Ile Asp Phe Ala Ala Lys Gln Gly Asn Gly Lys Ile Glu His
                165                 170                 175

Leu Lys Ser Pro Glu Leu Gly Leu Ala Ala Lys Gln Leu Asn Val Asp
            180                 185                 190

Leu Ala Ala Ala Asp Ile Lys Pro Asp Gly Lys Arg His Ala Val Ile
        195                 200                 205

Ser Gly Ser Val Leu Tyr Asn Gln Ala Glu Lys Gly Ser Tyr Ser Leu
    210                 215                 220

Gly Ile Phe Gly Gly Lys Ala Gln Glu Val Ala Gly Ser Ala Glu Val
225                 230                 235                 240

Lys Thr Val Asn Gly Ile Arg His Leu Glu His His His His His His
                245                 250                 255
```

<210> SEQ ID NO 24
<211> LENGTH: 256
<212> TYPE: PRT
<213> ORGANISM: Artificial Sequence
<220> FEATURE:
<223> OTHER INFORMATION: fHbp polypeptide with His6 tag

<400> SEQUENCE: 24

```
Val Ala Ala Asp Ile Gly Ala Gly Leu Ala Asp Ala Leu Thr Ala Pro
1               5                   10                  15

Leu Asp His Lys Asp Lys Gly Leu Gln Ser Leu Thr Leu Asp Gln Ser
            20                  25                  30

Val Arg Lys Asn Glu Lys Leu Lys Leu Ala Ala Gln Gly Ala Glu Lys
        35                  40                  45
```

Thr Tyr Gly Asn Gly Asp Ser Leu Asn Thr Gly Lys Leu Lys Asn Asp
    50                  55                  60

Lys Val Ser Arg Phe Asp Phe Ile Arg Gln Ile Glu Val Asp Gly Lys
65                  70                  75                  80

Leu Ile Thr Leu Glu Ser Gly Glu Phe Gln Val Tyr Lys Gln Ser His
                85                  90                  95

Ser Ala Leu Thr Ala Leu Gln Thr Glu Gln Val Gln Asp Ser Glu Asp
            100                 105                 110

Ser Gly Lys Met Val Ala Lys Arg Gln Phe Arg Ile Gly Asp Ile Ala
            115                 120                 125

Gly Glu His Thr Ser Phe Asp Lys Leu Pro Lys Gly Gly Ser Ala Thr
        130                 135                 140

Tyr Arg Gly Thr Ala Phe Gly Ser Asp Asp Ala Gly Gly Lys Leu Thr
145                 150                 155                 160

Tyr Thr Ile Asp Phe Ala Ala Lys Gln Gly His Gly Lys Ile Glu His
                165                 170                 175

Leu Lys Ser Pro Glu Leu Asn Val Glu Leu Ala Thr Ala Tyr Ile Lys
            180                 185                 190

Pro Asp Glu Lys Arg His Ala Val Ile Ser Gly Ser Val Leu Tyr Asn
        195                 200                 205

Gln Asp Glu Lys Gly Ser Tyr Ser Leu Gly Ile Phe Gly Gly Gln Ala
        210                 215                 220

Gln Glu Val Ala Gly Ser Ala Glu Val Glu Thr Ala Asn Gly Ile His
225                 230                 235                 240

His Ile Gly Leu Ala Ala Lys Gln Leu Glu His His His His His
                245                 250                 255

<210> SEQ ID NO 25
<211> LENGTH: 256
<212> TYPE: PRT
<213> ORGANISM: Artificial Sequence
<220> FEATURE:
<223> OTHER INFORMATION: Mutated fHbp polypeptide

<400> SEQUENCE: 25

Val Ala Ala Asp Ile Gly Ala Gly Leu Ala Asp Ala Leu Thr Ala Pro
1               5                   10                  15

Leu Asp His Lys Asp Lys Gly Leu Gln Ser Leu Thr Leu Asp Gln Ser
            20                  25                  30

Val Arg Lys Asn Glu Lys Leu Lys Leu Ala Ala Gln Gly Ala Glu Lys
        35                  40                  45

Thr Tyr Gly Asn Gly Asp Ser Leu Asn Thr Gly Lys Leu Lys Asn Asp
    50                  55                  60

Lys Val Ser Arg Phe Asp Phe Ile Arg Gln Ile Glu Val Asp Gly Lys
65                  70                  75                  80

Leu Ile Th

Tyr Thr Ile Asp Phe Ala Ala Lys Gln Gly His Gly Lys Ile Glu His
                165                 170                 175

Leu Lys Ser Pro Glu Leu Asn Val Glu Leu Ala Thr Ala Tyr Ile Lys
            180                 185                 190

Pro Asp Glu Lys Arg His Ala Val Ile Ser Gly Ser Val Leu Tyr Asn
            195                 200                 205

Gln Asp Ala Lys Gly Ser Tyr Ser Leu Gly Ile Phe Gly Gly Gln Ala
210                 215                 220

Gln Glu Val Ala Gly Ser Ala Glu Val Glu Thr Ala Asn Gly Ile His
225                 230                 235                 240

His Ile Gly Leu Ala Ala Lys Gln Leu Glu His His His His His His
            245                 250                 255

<210> SEQ ID NO 26
<211> LENGTH: 256
<212> TYPE: PRT
<213> ORGANISM: Artificial Sequence
<220> FEATURE:
<223> OTHER INFORMATION: Mutated fHbp polypeptide

<400> SEQUENCE: 26

Val Ala Ala Asp Ile Gly Ala Gly Leu Ala Asp Ala Leu Thr Ala Pro
1               5                   10                  15

Leu Asp His Lys Asp Lys Gly Leu Gln Ser Leu Thr Leu Asp Gln Ser
            20                  25                  30

Val Arg Lys Asn Glu Lys Leu Lys Leu Ala Ala Gln Gly Ala Glu Lys
        35                  40                  45

Thr Tyr Gly Asn Gly Asp Ser Leu Asn Thr Gly Lys Leu Lys Asn Asp
    50                  55                  60

Lys Val Ser Arg Phe Asp Phe Ile Arg Gln Ile Glu Val Asp Gly Lys
65                  70                  75                  80

Leu Ile Thr Leu Glu Ser Gly Glu Phe Gln Val Tyr Lys Gln Ser His
                85                  90                  95

Ser Ala Leu Thr Ala Leu Gln Thr Glu Gln Val Gln Asp Ser Glu Asp
            100                 105                 110

Ser Gly Lys Met Val Ala Lys Arg Gln Phe Arg Ile Gly Asp Ile Ala
        115                 120                 125

Gly Glu His Thr Ser Phe Asp Lys Leu Pro Lys Gly Gly Ser Ala Thr
    130                 135                 140

Tyr Arg Gly Thr Ala Phe Gly Ser Asp Asp Ala Gly Gly Lys Leu Thr
145                 150                 155                 160

Tyr Thr Ile Asp Phe Ala Ala Lys Gln Gly His Gly Lys Ile Glu His
                165                 170                 175

Leu Lys Ser Pro Glu Leu Asn Val Glu Leu Ala Thr Ala Tyr Ile Lys
            180                 185                 190

Pro Asp Glu Lys Arg His Ala Val Ile Ser Gly Ser Val Leu Tyr Asn
        195                 200                 205

Gln Asp Glu Lys Gly Ser Tyr Arg Leu Gly Ile Phe Gly Gly Gln Ala
    210                 215                 220

Gln Glu Val Ala Gly Ser Ala Glu Val Glu Thr Ala Asn Gly Ile His
225                 230                 235                 240

His Ile Gly Leu Ala Ala Lys Gln Leu Glu His His His His His His
                245                 250                 255

<210> SEQ ID NO 27
<211> LENGTH: 259

-continued

```
<212> TYPE: PRT
<213> ORGANISM: Artificial Sequence
<220> FEATURE:
<223> OTHER INFORMATION: fHbp polypeptide with His6 tag

<400> SEQUENCE: 27
```

Val Ala Ala Asp Ile Gly Ala Gly Leu Ala Asp Ala Leu Thr Ala Pro
1               5                   10                  15

Leu Asp His Lys Asp Lys Gly Leu Lys Ser Leu Thr Leu Glu Asp Ser
            20                  25                  30

Ile Ser Gln Asn Gly Thr Leu Thr Leu Ser Ala Gln Gly Ala Glu Arg
        35                  40                  45

Thr Phe Lys Ala Gly Asp Lys Asp Asn Ser Leu Asn Thr Gly Lys Leu
    50                  55                  60

Lys Asn Asp Lys Ile Ser Arg Phe Asp Phe Ile Arg Gln Ile Glu Val
65                  70                  75                  80

Asp Gly Gln Leu Ile Thr Leu Glu Ser Gly Glu Phe Gln Val Tyr Lys
                85                  90                  95

Gln Ser His Ser Ala Leu Thr Ala Leu Gln Thr Glu Gln Val Gln Asp
            100                 105                 110

Ser Glu His Ser Gly Lys Met Val Ala Lys Arg Gln Phe Arg Ile Gly
        115                 120                 125

Asp Ile Val Gly Glu His Thr Ser Phe Gly Lys Leu Pro Lys Asp Val
    130                 135                 140

Met Ala Thr Tyr Arg Gly Thr Ala Phe Gly Ser Asp Asp Ala Gly Gly
145                 150                 155                 160

Lys Leu Thr Tyr Thr Ile Asp Phe Ala Ala Lys Gln Gly His Gly Lys
                165                 170                 175

Ile Glu His Leu Lys Ser Pro Glu Leu Asn Val Asp Leu Ala Ala Ala
            180                 185                 190

Asp Ile Lys Pro Asp Glu Lys His His Ala Val Ile Ser Gly Ser Val
        195                 200                 205

Leu Tyr Asn Gln Ala Glu Lys Gly Ser Tyr Ser Leu Gly Ile Phe Gly
    210                 215                 220

Gly Gln Ala Gln Glu Val Ala Gly Ser Ala Glu Val Glu Thr Ala Asn
225                 230                 235                 240

Gly Ile Arg His Ile Gly Leu Ala Ala Lys Gln Leu Glu His His His
                245                 250                 255

His His His

```
<210> SEQ ID NO 28
<211> LENGTH: 259
<212> TYPE: PRT
<213> ORGANISM: Artificial Sequence
<220> FEATURE:
<223> OTHER INFORMATION: Mutated fHbp polypeptide with His6 tag

<400> SEQUENCE: 28
```

Val Ala Ala Asp Ile Gly Ala Gly Leu Ala Asp Ala Leu Thr Ala Pro
1               5                   10                  15

Leu Asp His Lys Asp Lys Gly Leu Lys Ser Leu Thr Leu Glu Asp Ser
            20                  25                  30

Ile Ser Gln Asn Gly Thr Leu Thr Leu Ser Ala Gln Gly Ala Glu Arg
        35                  40                  45

Thr Phe Lys Ala Gly Asp Lys Asp Asn Ser Leu Asn Thr Gly Lys Leu
    50                  55                  60

```
Lys Asn Asp Lys Ile Ser Arg Phe Asp Phe Ile Arg Gln Ile Glu Val
 65                  70                  75                  80

Asp Gly Gln Leu Ile Thr Leu Glu Ser Gly Glu Phe Gln Val Tyr Lys
                 85                  90                  95

Gln Ser His Ser Ala Leu Thr Ala Leu Gln Thr Glu Gln Val Gln Asp
            100                 105                 110

Ser Glu His Ser Gly Lys Met Val Ala Lys Arg Gln Phe Arg Ile Gly
            115                 120                 125

Asp Ile Val Gly Glu His Thr Ser Phe Gly Lys Leu Pro Lys Asp Val
130                 135                 140

Met Ala Thr Tyr Arg Gly Thr Ala Phe Gly Ser Asp Asp Ala Gly Gly
145                 150                 155                 160

Lys Leu Thr Tyr Thr Ile Asp Phe Ala Ala Lys Gln Gly His Gly Lys
                165                 170                 175

Ile Glu His Leu Lys Ser Pro Glu Leu Asn Val Asp Leu Ala Ala Ala
            180                 185                 190

Asp Ile Lys Pro Asp Glu Lys His His Ala Val Ile Ser Gly Ser Val
            195                 200                 205

Leu Tyr Asn Gln Ala Ala Lys Gly Ser Tyr Ser Leu Gly Ile Phe Gly
210                 215                 220

Gly Gln Ala Gln Glu Val Ala Gly Ser Ala Glu Val Glu Thr Ala Asn
225                 230                 235                 240

Gly Ile Arg His Ile Gly Leu Ala Ala Lys Gln Leu Glu His His His
                245                 250                 255

His His His

<210> SEQ ID NO 29
<211> LENGTH: 753
<212> TYPE: PRT
<213> ORGANISM: Artificial Sequence
<220> FEATURE:
<223> OTHER INFORMATION: fHbp fusion polypeptide

<400> SEQUENCE: 29

Val Ala Ala Asp Ile Gly Ala Gly Leu Ala Asp Ala Leu Thr Ala Pro
  1               5                  10                  15

Leu Asp His Lys Asp Lys Ser Leu Gln Ser Leu Thr Leu Asp Gln Ser
                 20                  25                  30

Val Arg Lys Asn Glu Lys Leu Lys Leu Ala Ala Gln Gly Ala Glu Lys
             35                  40                  45

Thr Tyr Gly Asn Gly Asp Ser Leu Asn Thr Gly Lys Leu Lys Asn Asp
 50                  55                  60

Lys Val Ser Phe Asp Phe Ile Arg Gln Ile Glu Val Asp Gly Gln Leu
 65                  70                  75                  80

Ile Thr Leu Glu Ser Gly Glu Phe Gln Ile Tyr Lys Gln Asp His Ser
                 85                  90                  95

Ala Val Val Ala Leu Gln Ile Glu Lys Ile Asn Asn Pro Asp Lys Ile
            100                 105                 110

Asp Ser Leu Ile Asn Gln Arg Ser Phe Leu Val Ser Gly Leu Gly Gly
            115                 120                 125

Glu His Thr Ala Phe Asn Gln Leu Pro Asp Gly Lys Ala Glu Tyr His
130                 135                 140

Gly Lys Ala Phe Ser Ser Asp Asp Ala Gly Gly Lys Leu Thr Tyr Thr
145                 150                 155                 160

Ile Asp Phe Ala Ala Lys Gln Gly His Gly Lys Ile Glu His Leu Lys
```

```
                165                 170                 175
Thr Pro Glu Gln Asn Val Glu Leu Ala Ala Ala Glu Leu Lys Ala Asp
                    180                 185                 190
Glu Lys Ser His Ala Val Ile Leu Gly Asp Thr Arg Tyr Gly Ser Glu
                    195                 200                 205
Glu Lys Gly Thr Tyr His Leu Ala Leu Phe Gly Asp Arg Ala Gln Glu
                    210                 215                 220
Ile Ala Gly Ser Ala Thr Val Lys Ile Gly Glu Lys Val His Glu Ile
225                 230                 235                 240
Gly Ile Ala Gly Lys Gln Gly Ser Gly Gly Gly Val Ala Ala Asp
                    245                 250                 255
Ile Gly Thr Gly Leu Ala Asp Ala Leu Thr Ala Pro Leu Asp His Lys
                    260                 265                 270
Asp Lys Gly Leu Lys Ser Leu Thr Leu Glu Asp Ser Ile Pro Gln Asn
                    275                 280                 285
Gly Thr Leu Thr Leu Ser Ala Gln Gly Ala Glu Lys Thr Phe Lys Ala
                    290                 295                 300
Gly Asp Lys Asp Asn Ser Leu Asn Thr Gly Lys Leu Lys Asn Asp Lys
305                 310                 315                 320
Ile Ser Arg Phe Asp Phe Val Gln Lys Ile Glu Val Asp Gly Gln Thr
                    325                 330                 335
Ile Thr Leu Ala Ser Gly Glu Phe Gln Ile Tyr Lys Gln Asn His Ser
                    340                 345                 350
Ala Val Val Ala Leu Gln Ile Glu Lys Ile Asn Asn Pro Asp Lys Thr
                    355                 360                 365
Asp Ser Leu Ile Asn Gln Arg Ser Phe Leu Val Ser Gly Leu Gly Gly
                    370                 375                 380
Glu His Thr Ala Phe Asn Gln Leu Pro Gly Gly Lys Ala Glu Tyr His
385                 390                 395                 400
Gly Lys Ala Phe Ser Ser Asp Asp Pro Asn Gly Arg Leu His Tyr Ser
                    405                 410                 415
Ile Asp Phe Thr Lys Lys Gln Gly Tyr Gly Arg Ile Glu His Leu Lys
                    420                 425                 430
Thr Leu Glu Gln Asn Val Glu Leu Ala Ala Ala Glu Leu Lys Ala Asp
                    435                 440                 445
Glu Lys Ser His Ala Val Ile Leu Gly Asp Thr Arg Tyr Gly Ser Glu
                    450                 455                 460
Glu Lys Gly Thr Tyr His Leu Ala Leu Phe Gly Asp Arg Ala Gln Glu
465                 470                 475                 480
Ile Ala Gly Ser Ala Thr Val Lys Ile Gly Glu Lys Val His Glu Ile
                    485                 490                 495
Gly Ile Ala Gly Lys Gln Gly Ser Gly Gly Gly Val Ala Ala Asp
                    500                 505                 510
Ile Gly Ala Gly Leu Ala Asp Ala Leu Thr Ala Pro Leu Asp His Lys
                    515                 520                 525
Asp Lys Gly Leu Gln Ser Leu Thr Leu Asp Gln Ser Val Arg Lys Asn
                    530                 535                 540
Glu Lys Leu Lys Leu Ala Ala Gln Gly Ala Glu Lys Thr Tyr Gly Asn
545                 550                 555                 560
Gly Ser Leu Asn Thr Gly Lys Leu Lys Asn Asp Lys Val Ser Arg Phe
                    565                 570                 575
Asp Phe Ile Arg Gln Ile Glu Val Asp Gly Gln Leu Ile Thr Leu Glu
                    580                 585                 590
```

-continued

```
Ser Gly Glu Phe Gln Val Tyr Lys Gln Ser His Ser Ala Leu Thr Ala
            595                 600                 605

Phe Gln Thr Glu Gln Ile Gln Asp Ser Glu His Ser Gly Lys Met Val
610                 615                 620

Ala Lys Arg Gln Phe Arg Ile Gly Asp Ile Ala Gly Glu His Thr Ser
625                 630                 635                 640

Phe Asp Lys Leu Pro Glu Gly Gly Arg Ala Thr Tyr Arg Gly Thr Ala
                645                 650                 655

Phe Gly Ser Asp Asp Ala Gly Gly Lys Leu Thr Tyr Thr Ile Asp Phe
                660                 665                 670

Ala Ala Lys Gln Gly Asn Gly Lys Ile Glu His Leu Lys Ser Pro Glu
                675                 680                 685

Leu Asn Val Asp Leu Ala Ala Ala Ile Lys Pro Asp Gly Lys Arg His
            690                 695                 700

Ala Val Ile Ser Gly Ser Val Leu Tyr Asn Gln Ala Glu Lys Gly Ser
705                 710                 715                 720

Tyr Ser Leu Gly Ile Phe Gly Lys Ala Gln Glu Val Ala Gly Ser Ala
                725                 730                 735

Glu Val Lys Thr Val Asn Gly Ile Arg His Ile Gly Leu Ala Ala Lys
            740                 745                 750

Gln

<210> SEQ ID NO 30
<211> LENGTH: 753
<212> TYPE: PRT
<213> ORGANISM: Artificial Sequence
<220> FEATURE:
<223> OTHER INFORMATION: fHbp fusion polypeptide

<400> SEQUENCE: 30

Val Ala Ala Asp Ile Gly Ala Gly Leu Ala Asp Ala Leu Thr Ala Pro
1               5                   10                  15

Leu Asp His Lys Asp Lys Ser Leu Gln Ser Leu Thr Leu Asp Gln Val
            20                  25                  30

Val Arg Lys Asn Glu Lys Leu Lys Leu Ala Ala Gln Gly Ala Glu Lys
        35                  40                  45

Thr Tyr Gly Asn Gly Asp Ser Leu Asn Thr Gly Lys Leu Lys Asn Asp
    50                  55                  60

Lys Val Ser Phe Asp Phe Ile Arg Gln Ile Glu Val Asp Gly Gln Leu
65                  70                  75                  80

Ile Thr Leu Glu Ser Gly Glu Phe Gln Ile Tyr Lys Gln Asp His Ser
                85                  90                  95

Ala Val Val Ala Leu Gln Ile Glu Lys Ile Asn Asn Pro Asp Lys Ile
            100                 105                 110

Asp Ser Leu Ile Asn Gln Arg Ser Phe Arg Val Ser Gly Leu Gly Gly
        115                 120                 125

Glu His Thr Ala Phe Asn Gln Leu Pro Asp Gly Lys Ala Glu Tyr His
    130                 135                 140

Gly Lys Ala Phe Ser Ser Asp Asp Ala Gly Gly Lys Leu Thr Tyr Thr
145                 150                 155                 160

Ile Asp Phe Ala Ala Lys Gln Gly His Gly Lys Ile Glu His Leu Lys
                165                 170                 175

Thr Pro Glu Gln Asn Val Glu Leu Ala Ala Ala Glu Leu Lys Ala Asp
            180                 185                 190
```

```
Glu Lys Ser His Ala Val Ile Leu Gly Asp Thr Arg Tyr Gly Ser Glu
            195                 200                 205
Glu Lys Gly Thr Tyr His Leu Ala Leu Phe Gly Asp Arg Ala Gln Glu
            210                 215                 220
Ile Ala Gly Ser Ala Thr Val Lys Ile Gly Glu Lys Val His Glu Ile
225                 230                 235                 240
Gly Ile Ala Gly Lys Gln Gly Ser Gly Gly Gly Val Ala Ala Asp
            245                 250                 255
Ile Gly Thr Gly Leu Ala Asp Ala Leu Thr Ala Pro Leu Asp His Lys
            260                 265                 270
Asp Lys Gly Leu Lys Ser Leu Thr Leu Glu Asp Val Ile Pro Gln Asn
            275                 280                 285
Gly Thr Leu Thr Leu Ser Ala Gln Gly Ala Glu Lys Thr Phe Lys Ala
            290                 295                 300
Gly Asp Lys Asp Asn Ser Leu Asn Thr Gly Lys Leu Lys Asn Asp Lys
305                 310                 315                 320
Ile Ser Arg Phe Asp Phe Val Gln Lys Ile Glu Val Asp Gly Gln Thr
            325                 330                 335
Ile Thr Leu Ala Ser Gly Glu Phe Gln Ile Tyr Lys Gln Asn His Ser
            340                 345                 350
Ala Val Val Ala Leu Gln Ile Glu Lys Ile Asn Asn Pro Asp Lys Thr
            355                 360                 365
Asp Ser Leu Ile Asn Gln Arg Ser Phe Arg Val Ser Gly Leu Gly Gly
            370                 375                 380
Glu His Thr Ala Phe Asn Gln Leu Pro Gly Gly Lys Ala Glu Tyr His
385                 390                 395                 400
Gly Lys Ala Phe Ser Ser Asp Asp Pro Asn Gly Arg Leu His Tyr Ser
            405                 410                 415
Ile Asp Phe Thr Lys Lys Gln Gly Tyr Gly Arg Ile Glu His Leu Lys
            420                 425                 430
Thr Leu Glu Gln Asn Val Glu Leu Ala Ala Ala Glu Leu Lys Ala Asp
            435                 440                 445
Glu Lys Ser His Ala Val Ile Leu Gly Asp Thr Arg Tyr Gly Ser Glu
            450                 455                 460
Glu Lys Gly Thr Tyr His Leu Ala Leu Phe Gly Asp Arg Ala Gln Glu
465                 470                 475                 480
Ile Ala Gly Ser Ala Thr Val Lys Ile Gly Glu Lys Val His Glu Ile
                    485                 490                 495
Gly Ile Ala Gly Lys Gln Gly Ser Gly Gly Gly Val Ala Ala Asp
            500                 505                 510
Ile Gly Ala Gly Leu Ala Asp Ala Leu Thr Ala Pro Leu Asp His Lys
            515                 520                 525
Asp Lys Gly Leu Gln Ser Leu Thr Leu Asp Gln Ser Val Ser Lys Asn
            530                 535                 540
Glu Lys Leu Lys Leu Ala Ala Gln Gly Ala Glu Lys Thr Tyr Gly Asn
545                 550                 555                 560
Gly Ser Leu Asn Thr Gly Lys Leu Lys Asn Asp Lys Val Ser Arg Phe
                    565                 570                 575
Asp Phe Ile Arg Gln Ile Glu Val Asp Gly Gln Leu Ile Thr Leu Glu
            580                 585                 590
Ser Gly Glu Phe Gln Val Tyr Lys Gln Ser His Ser Ala Leu Thr Ala
            595                 600                 605
Phe Gln Thr Glu Gln Ile Gln Asp Ser Glu His Ser Gly Lys Met Val
```

```
            610                 615                 620
Ala Lys Arg Gln Phe Arg Ile Gly Asp Ile Ala Gly Glu His Thr Ser
625                 630                 635                 640

Phe Asp Lys Leu Pro Glu Gly Gly Arg Ala Thr Tyr Arg Gly Thr Ala
                645                 650                 655

Phe Gly Ser Asp Asp Ala Gly Gly Lys Leu Thr Tyr Thr Ile Asp Phe
                660                 665                 670

Ala Ala Lys Gln Gly Asn Gly Lys Ile Glu His Leu Lys Ser Pro Glu
                675                 680                 685

Leu Asn Val Asp Leu Ala Ala Ala Ile Lys Pro Asp Gly Lys Arg His
            690                 695                 700

Ala Val Ile Ser Gly Ser Val Leu Tyr Asn Gln Ala Glu Lys Gly Ser
705                 710                 715                 720

Tyr Ser Leu Gly Ile Phe Gly Lys Ala Gln Glu Val Ala Gly Ser Ala
                725                 730                 735

Glu Val Lys Thr Val Asn Gly Ile Arg His Ile Gly Leu Ala Ala Lys
                740                 745                 750

Gln

<210> SEQ ID NO 31
<211> LENGTH: 274
<212> TYPE: PRT
<213> ORGANISM: Neisseria meningitidis

<400> SEQUENCE: 31

Met Asn Arg Thr Ala Phe Cys Cys Phe Ser Leu Thr Ala Ala Leu Ile
1               5                   10                  15

Leu Thr Ala Cys Ser Ser Gly Gly Gly Val Ala Ala Asp Ile Gly
            20                  25                  30

Ala Gly Leu Ala Asp Ala Leu Thr Ala Pro Leu Asp His Lys Asp Lys
        35                  40                  45

Gly Leu Gln Ser Leu Thr Leu Asp Gln Ser Val Arg Lys Asn Glu Lys
    50                  55                  60

Leu Lys Leu Ala Ala Gln Gly Ala Glu Lys Thr Tyr Gly Asn Gly Asp
65                  70                  75                  80

Ser Leu Asn Thr Gly Lys Leu Lys Asn Asp Lys Val Ser Arg Phe Asp
                85                  90                  95

Phe Ile Arg Gln Ile Glu Val Asp Gly Lys Leu Ile Thr Leu Glu Ser
            100                 105                 110

Gly Glu Phe Gln Val Tyr Lys Gln Ser His Ser Ala Leu Thr Ala Leu
        115                 120                 125

Gln Thr Glu Gln Val Gln Asp Ser Glu Asp Ser Gly Lys Met Val Ala
    130                 135                 140

Lys Arg Gln Phe Arg Ile Gly Asp Ile Ala Gly Glu His Thr Ser Phe
145                 150                 155                 160

Asp Lys Leu Pro Lys Gly Gly Ser Ala Thr Tyr Arg Gly Thr Ala Phe
                165                 170                 175

Gly Ser Asp Asp Ala Gly Gly Lys Leu Thr Tyr Thr Ile Asp Phe Ala
            180                 185                 190

Ala Lys Gln Gly His Gly Lys Ile Glu His Leu Lys Ser Pro Glu Leu
        195                 200                 205

Asn Val Glu Leu Ala Thr Ala Tyr Ile Lys Pro Asp Glu Lys Arg His
    210                 215                 220

Ala Val Ile Ser Gly Ser Val Leu Tyr Asn Gln Asp Glu Lys Gly Ser
```

```
                225                 230                 235                 240
Tyr Ser Leu Gly Ile Phe Gly Gly Gln Ala Gln Glu Val Ala Gly Ser
                    245                 250                 255
Ala Glu Val Glu Thr Ala Asn Gly Ile His His Ile Gly Leu Ala Ala
                260                 265                 270
Lys Gln

<210> SEQ ID NO 32
<211> LENGTH: 282
<212> TYPE: PRT
<213> ORGANISM: Neisseria meningitidis

<400> SEQUENCE: 32

Met Asn Arg Thr Thr Phe Cys Cys Leu Ser Leu Thr Ala Ala Leu Ile
1               5                   10                  15
Leu Thr Ala Cys Ser Ser Gly Gly Gly Ser Gly Gly Gly Gly Gly Val
                20                  25                  30
Ala Ala Asp Ile Gly Ala Gly Leu Ala Asp Ala Leu Thr Ala Pro Leu
            35                  40                  45
Asp His Lys Asp Lys Gly Leu Lys Ser Leu Thr Leu Glu Asp Ser Ile
50                  55                  60
Ser Gln Asn Gly Thr Leu Thr Leu Ser Ala Gln Gly Ala Glu Arg Thr
65                  70                  75                  80
Phe Lys Ala Gly Asp Lys Asp Asn Ser Leu Asn Thr Gly Lys Leu Lys
                85                  90                  95
Asn Asp Lys Ile Ser Arg Phe Asp Phe Ile Arg Gln Ile Glu Val Asp
            100                 105                 110
Gly Gln Leu Ile Thr Leu Glu Ser Gly Glu Phe Gln Val Tyr Lys Gln
        115                 120                 125
Ser His Ser Ala Leu Thr Ala Leu Gln Thr Glu Gln Val Gln Asp Ser
130                 135                 140
Glu His Ser Gly Lys Met Val Ala Lys Arg Gln Phe Arg Ile Gly Asp
145                 150                 155                 160
Ile Val Gly Glu His Thr Ser Phe Gly Lys Leu Pro Lys Asp Val Met
                165                 170                 175
Ala Thr Tyr Arg Gly Thr Ala Phe Gly Ser Asp Asp Ala Gly Gly Lys
            180                 185                 190
Leu Thr Tyr Thr Ile Asp Phe Ala Ala Lys Gln Gly His Gly Lys Ile
        195                 200                 205
Glu His Leu Lys Ser Pro Glu Leu Asn Val Asp Leu Ala Ala Ala Asp
    210                 215                 220
Ile Lys Pro Asp Glu Lys His His Ala Val Ile Ser Gly Ser Val Leu
225                 230                 235                 240
Tyr Asn Gln Ala Glu Lys Gly Ser Tyr Ser Leu Gly Ile Phe Gly Gly
                245                 250                 255
Gln Ala Gln Glu Val Ala Gly Ser Ala Glu Val Glu Thr Ala Asn Gly
            260                 265                 270
Ile Arg His Ile Gly Leu Ala Ala Lys Gln
        275                 280

<210> SEQ ID NO 33
<211> LENGTH: 254
<212> TYPE: PRT
<213> ORGANISM: Neisseria meningitidis

<400> SEQUENCE: 33
```

```
Cys Ser Ser Gly Gly Gly Val Ala Ala Asp Ile Gly Ala Gly Leu
1               5                   10                  15

Ala Asp Ala Leu Thr Ala Pro Leu Asp His Lys Asp Lys Gly Leu Gln
            20              25              30

Ser Leu Thr Leu Asp Gln Ser Val Arg Lys Asn Glu Lys Leu Lys Leu
            35              40              45

Ala Ala Gln Gly Ala Glu Lys Thr Tyr Gly Asn Gly Asp Ser Leu Asn
    50              55              60

Thr Gly Lys Leu Lys Asn Asp Lys Val Ser Arg Phe Asp Phe Ile Gln
65              70              75              80

Ile Glu Val Asp Gly Gln Leu Ile Thr Leu Glu Ser Gly Glu Phe Gln
                85              90              95

Val Tyr Lys Gln Ser His Ser Ala Leu Thr Ala Phe Gln Thr Glu Gln
            100             105             110

Ile Gln Asp Ser Glu His Ser Gly Lys Met Val Ala Lys Arg Gln Phe
            115             120             125

Arg Ile Gly Asp Ile Ala Gly Glu His Thr Ser Phe Asp Lys Leu Pro
            130             135             140

Glu Gly Gly Arg Ala Thr Tyr Arg Gly Thr Ala Phe Gly Ser Asp Asp
145             150             155             160

Ala Gly Gly Lys Leu Thr Tyr Thr Ile Asp Phe Ala Ala Lys Gln Gly
            165             170             175

Asn Gly Lys Ile Glu His Leu Lys Ser Pro Glu Leu Asn Val Asp Leu
            180             185             190

Ala Ala Ala Asp Ile Lys Pro Asp Gly Lys Arg His Ala Val Ile Ser
    195             200             205

Gly Ser Val Leu Tyr Asn Gln Ala Glu Lys Gly Ser Tyr Ser Leu Gly
    210             215             220

Ile Phe Gly Gly Lys Ala Gln Glu Val Ala Gly Ser Ala Glu Val Lys
225             230             235             240

Thr Val Asn Gly Ile Arg His Ile Gly Leu Ala Ala Lys Gln
            245             250

<210> SEQ ID NO 34
<211> LENGTH: 12
<212> TYPE: PRT
<213> ORGANISM: Artificial Sequence
<220> FEATURE:
<223> OTHER INFORMATION: N-terminal sequence

<400> SEQUENCE: 34

Met Gly Pro Asp Ser Asp Arg Leu Gln Gln Arg Arg
1               5                   10
```